(12) United States Patent
Hong et al.

(10) Patent No.: US 9,768,389 B2
(45) Date of Patent: Sep. 19, 2017

(54) COMPOUND FOR OPTOELECTRONIC DEVICE, ORGANIC LIGHT-EMITTING DIODE INCLUDING SAME, AND DISPLAY DEVICE INCLUDING ORGANIC LIGHT-EMITTING DIODE

(71) Applicants: Jin-Seok Hong, Uiwang-si (KR); Young-Kyoung Jo, Uiwang-si (KR); Dong-Wan Ryu, Uiwang-si (KR); Nam-Heon Lee, Uiwang-si (KR); Han-Ill Lee, Uiwang-si (KR); Sung-Hyun Jung, Uiwang-si (KR); Mi-Young Chae, Uiwang-si (KR); Dal-Ho Huh, Uiwang-si (KR)

(72) Inventors: Jin-Seok Hong, Uiwang-si (KR); Young-Kyoung Jo, Uiwang-si (KR); Dong-Wan Ryu, Uiwang-si (KR); Nam-Heon Lee, Uiwang-si (KR); Han-Ill Lee, Uiwang-si (KR); Sung-Hyun Jung, Uiwang-si (KR); Mi-Young Chae, Uiwang-si (KR); Dal-Ho Huh, Uiwang-si (KR)

(73) Assignee: CHEIL INDUSTRIES, INC., Gumi-si, Gyeongsangbuk-Do (KR)

(*) Notice: Subject to any disclaimer, the term of this patent is extended or adjusted under 35 U.S.C. 154(b) by 686 days.

(21) Appl. No.: 14/360,697

(22) PCT Filed: Dec. 18, 2012

(86) PCT No.: PCT/KR2012/011040
§ 371 (c)(1),
(2) Date: May 27, 2014

(87) PCT Pub. No.: WO2013/100467
PCT Pub. Date: Jul. 4, 2013

(65) Prior Publication Data
US 2014/0332787 A1    Nov. 13, 2014

(30) Foreign Application Priority Data
Dec. 30, 2011 (KR) .......................... 10-2011-0147392

(51) Int. Cl.
*H01L 51/54* (2006.01)
*C09K 11/06* (2006.01)
(Continued)

(52) U.S. Cl.
CPC ........ *H01L 51/0058* (2013.01); *C07D 307/91* (2013.01); *C09K 11/06* (2013.01); *H01L 51/006* (2013.01); *H01L 51/0059* (2013.01); *H01L 51/0061* (2013.01); *H01L 51/0073* (2013.01); *H01L 51/0074* (2013.01); *H05B 33/14* (2013.01); *C09K 2211/1011* (2013.01); *C09K 2211/1014* (2013.01); *C09K 2211/1022* (2013.01); *C09K 2211/1088* (2013.01);
(Continued)

(58) Field of Classification Search
CPC ..... Y02E 10/549; Y02P 70/521; H05B 33/14; C07D 307/91; C09K 2211/00; C09K 2211/10; C09K 2211/1011; C09K 2211/1014; C09K 2211/1022; C09K 2211/1088; C09K 2211/1092; H01L 51/0032; H01L 51/005; H01L 51/0051; H01L 51/0052; H01L 51/0055; H01L 51/0058; H01L 51/0059; H01L 51/006; H01L 51/0062; H01L 51/0071; H01L 51/0072; H01L 51/0073; H01L 51/0074; H01L 51/50; H01L 51/5012; H01L 51/5016; H01L 51/5048; H01L 51/5056; H01L 51/5088; H01L 51/5092; H01L 51/5096; H01L 51/5072
USPC ....... 428/690, 691, 917, 411.4, 336; 427/58, 427/66; 313/500–512; 257/40, 88–103, 257/E51.001–E51.052; 252/301.16–301.35; 549/41, 330
See application file for complete search history.

(56) References Cited

U.S. PATENT DOCUMENTS

2007/0160870 A1* 7/2007 Yu .......................... H01L 51/006
                                                            428/690
2007/0222376 A1* 9/2007 Ohsawa .............. H01L 51/5016
                                                            313/506
(Continued)

FOREIGN PATENT DOCUMENTS

CN    101679855 A    3/2010
CN    101809117 A    8/2010
(Continued)

OTHER PUBLICATIONS

Jeon, et al., "Fluorenobenzofuran As the Core Structure of High Triplet Energy Host Materials for Green Phosphorescent Organic Light-Emitting Diodes", Journal of Materials Chemistry, vol. 22, No. 21, (2012), pp. 10537-10541.
(Continued)

*Primary Examiner* — Andrew K Bohaty
(74) *Attorney, Agent, or Firm* — Lee & Morse, P.C.

(57) ABSTRACT

Disclosed are a compound for an organic optoelectronic device, an organic light emitting diode including the same, and a display device including the organic light emitting diode. The compound for an organic optoelectronic device represented by a combination of the following Chemical Formula 1 and Chemical Formula 2 provides an organic light emitting diode having life-span characteristics due to excellent electrochemical and thermal stability, and high luminous efficiency at a low driving voltage.

15 Claims, 3 Drawing Sheets

(51) Int. Cl.
    *H01L 51/00*     (2006.01)
    *C07D 307/91*     (2006.01)
    *H05B 33/14*     (2006.01)
    *H01L 51/50*     (2006.01)

(52) U.S. Cl.
    CPC .. *C09K 2211/1092* (2013.01); *H01L 51/0055* (2013.01); *H01L 51/5012* (2013.01); *H01L 51/5048* (2013.01); *H01L 51/5056* (2013.01); *H01L 51/5072* (2013.01); *H01L 51/5088* (2013.01); *H01L 51/5092* (2013.01); *H01L 51/5096* (2013.01); *Y02E 10/549* (2013.01); *Y02P 70/521* (2015.11)

(56) References Cited

U.S. PATENT DOCUMENTS

| | | |
|---|---|---|
| 2008/0102312 A1 | 5/2008 | Parham et al. |
| 2009/0159874 A1 | 6/2009 | Vestweber et al. |
| 2011/0121274 A1 | 5/2011 | Parham et al. |

FOREIGN PATENT DOCUMENTS

| | | |
|---|---|---|
| CN | 1018091174 A | 8/2010 |
| DE | 10 2009 031 021 A1 | 1/2011 |
| KR | 10-2006-0080726 A | 7/2006 |
| KR | 10-2008-0015865 A | 2/2008 |
| KR | 10-2010-0028471 A | 3/2010 |
| KR | 10-2012-0060611 A | 6/2012 |
| WO | WO-2009/057978 A2 | 5/2009 |
| WO | WO-2009/124627 A1 | 10/2009 |
| WO | WO-2011/000455 A1 | 1/2011 |
| WO | WO 2013/017189 A1 | 2/2013 |

OTHER PUBLICATIONS

Extended European Search Report dated Jul. 14, 2015 in Corresponding European Patent Application No. 12863091.0.
Sang Eok Jang, et al., "Stable efficiency roll-off in red phosphorescent organic light-emitting diodes using a spirofluorene-benzofluorene based carbazole type host material", Journal of Luminescence 130 (2010) 2184-2187.
Search Report mailed Feb. 9, 2015 in corresponding Chinese Patent Application No. 2012800650009.

\* cited by examiner

COMPOUND FOR OPTOELECTRONIC DEVICE, ORGANIC LIGHT-EMITTING DIODE INCLUDING SAME, AND DISPLAY DEVICE INCLUDING ORGANIC LIGHT-EMITTING DIODE

TECHNICAL FIELD

A compound for an organic optoelectronic device being capable of providing an organic optoelectronic device having excellent life-span, efficiency, electrochemical stability, and thermal stability, an organic light emitting diode including the compound, and a display device including the organic light emitting diode are disclosed.

BACKGROUND ART

An organic optoelectronic device is a device requiring a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectronic device include an organic photoelectric device, an organic light emitting diode, an organic solar cell, an organic photo conductor drum, an organic transistor, and the like, which require a hole injecting or transport material, an electron injecting or transport material, or a light emitting material.

Particularly, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer includes a multi-layer including different materials, for example a hole injection layer, a hole transport layer, an emission layer, an electron transport layer, and an electron injection layer, in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used for a light emitting material of an organic light emitting diode in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectronic devices.

The low molecular organic light emitting diode is manufactured as a thin film in a vacuum deposition method and can have good efficiency and life-span performance. A polymer organic light emitting diode is manufactured in an inkjet or spin coating method has an advantage of low initial cost and being large-sized.

Both low molecular organic light emitting and polymer organic light emitting diodes have an advantage of self-light emitting, high speed response, wide viewing angle, ultrathin, high image quality, durability, large driving temperature range, and the like. In particular, they have good visibility due to self-light emitting characteristics compared with a conventional LCD (liquid crystal display) and have an advantage of decreasing thickness and weight of LCD up to a third, because they do not need a backlight.

In addition, since they have a response speed 1000 time faster microsecond unit than LCD, they can realize a perfect motion picture without after-image. Based on these advantages, they have been remarkably developed to have 80 times efficiency and more than 100 times life-span since they come out for the first time in the late 1980s. Recently, they keep being rapidly larger such as a 40-inch organic light emitting diode panel.

They are simultaneously required to have improved luminous efficiency and life-span in order to be larger. Herein, their luminous efficiency need smooth combination between holes and electrons in an emission layer. However, since an organic material in general has slower electron mobility than hole mobility, it has a drawback of inefficient combination between holes and electrons. Accordingly, while increasing electron injection and mobility from a cathode and simultaneously preventing movement of holes is required.

In order to improve life-span, a material crystallization caused by Joule heats generated during device operating is required to be prevented. Accordingly, there has been a strong need for an organic compound having excellent electron injection and mobility, and high electrochemical stability.

DISCLOSURE

Technical Problem

A compound for an organic optoelectronic device that may act as a hole injection and transport material or an electron injection and transport material, and also act as a light emitting host along with an appropriate dopant is provided.

An organic light emitting diode having excellent lifespan, efficiency, driving voltage, electrochemical stability, and thermal stability and a display device including the same are provided.

Technical Solution

In one embodiment of the present invention, a compound for an organic optoelectronic device represented by a combination of the following Chemical Formula 1 and Chemical Formula 2 is provided.

[Chemical Formula 1]

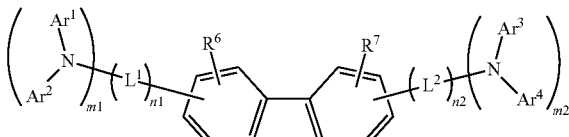

[Chemical Formula 2]

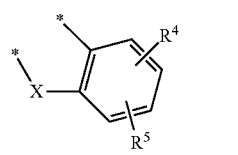

In the above Chemical Formulae 1 and 2, X is —O—, —S—, —S(O)— or —S(O)$_2$—, Ar$^1$ to Ar$^4$ are independently a substituted or unsubstituted C6 to C30 aryl group, or a substituted or unsubstituted C2 to C30 heteroaryl group, L$^1$ and L$^2$ are independently a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m1 and m2 are independently integers of 0 or 1, one of m1 and m2 is 1, n1 and n2 are independently integers ranging from 0 to 3, R$^1$ to R$^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group, and two *s of the above Chemical Formula 2 are bonded with the adjacent two *s of the above Chemical Formula 1 to form a fused ring.

The above Chemical Formula 1 may be represented by the following Chemical Formula 3.

[Chemical Formula 3]

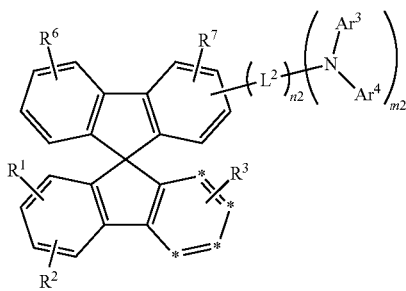

In the above Chemical Formula 3, Ar$^3$ and Ar$^4$ are independently a substituted or unsubstituted C6 to C30 aryl group, or a substituted or unsubstituted C2 to C30 heteroaryl group, L$^2$ is a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m2 is 1, n2 is an integer ranging from 0 to 3, R$^1$ to R$^3$, R$^6$ or R$^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group, and two *s of the above Chemical Formula 2 are bonded with the adjacent two *s of the above Chemical Formula 3 to form a fused ring.

The compound for an organic optoelectronic device may be represented by the following Chemical Formula 4.

[Chemical Formula 4]

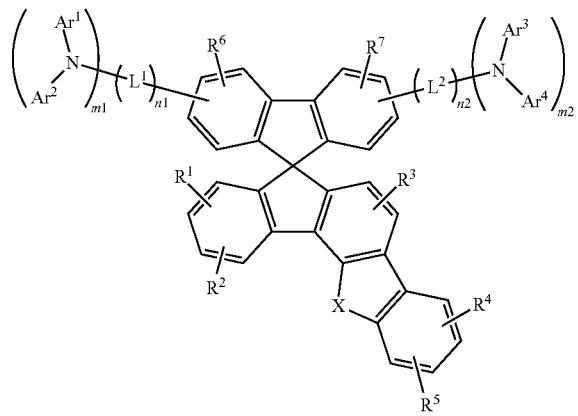

In the above Chemical Formula 4, X is —O—, —S—, —S(O)— or —S(O)$_2$—, Ar$^1$ to Ar$^4$ are independently a substituted or unsubstituted C6 to C30 aryl group, or a substituted or unsubstituted C2 to C30 heteroaryl group, L$^1$ and L$^2$ are independently a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m1 and m2 are independently integers of 0 or 1, one of m1 and m2 is 1, n1 and n2 are independently integers ranging from 0 to 3, and R$^1$ to R$^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

The compound for an organic optoelectronic device may be represented by the following Chemical Formula 5.

[Chemical Formula 5]

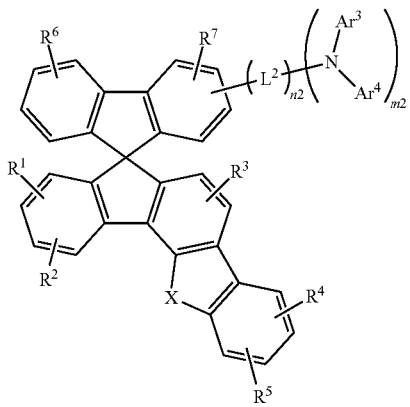

In the above Chemical Formula 5, $Ar^3$ and $Ar^4$ are independently a substituted or unsubstituted C6 to C30 aryl group, or a substituted or unsubstituted C2 to C30 heteroaryl group, $L^2$ is a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m2 is 1, n2 is an integer ranging from 0 to 3, and $R^1$ to $R^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

The $Ar^1$ to $Ar^4$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiopheneyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiopheneyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

The compound for an organic optoelectronic device may be represented by one of the following Chemical Formulae A-1 to A-72.

[Chemical Formula A-1]

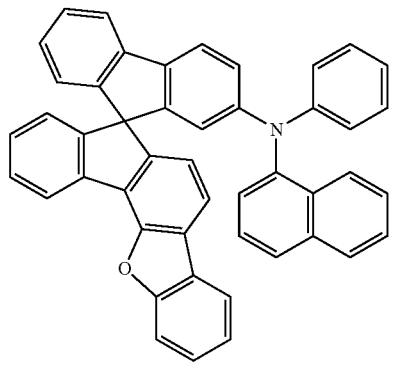

[Chemical Formula A-2]

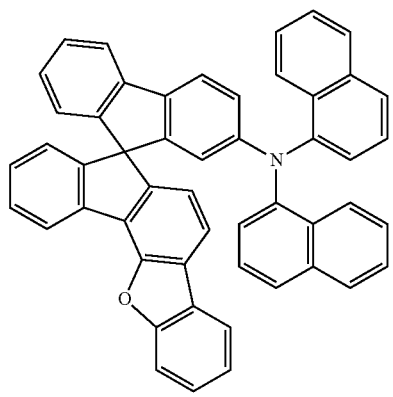

[Chemical Formula A-3]

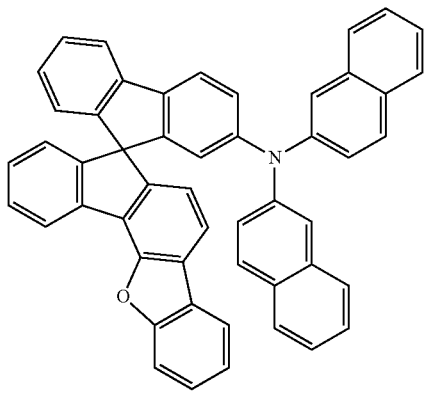

[Chemical Formula A-4]
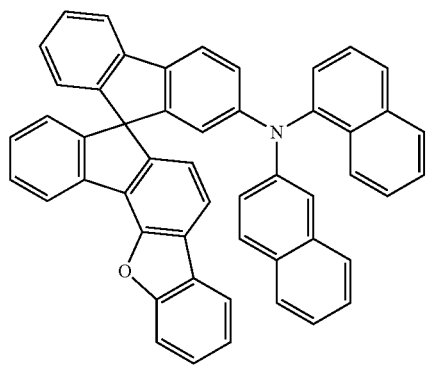
[Chemical Formula A-5]
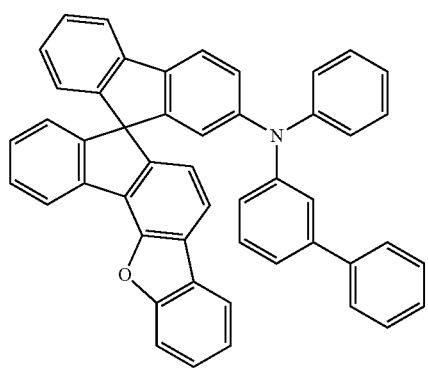
[Chemical Formula A-6]
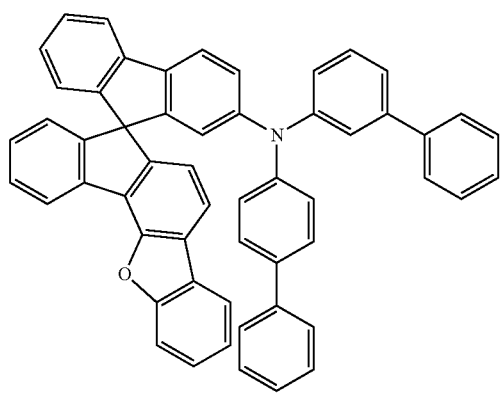
[Chemical Formula A-7]
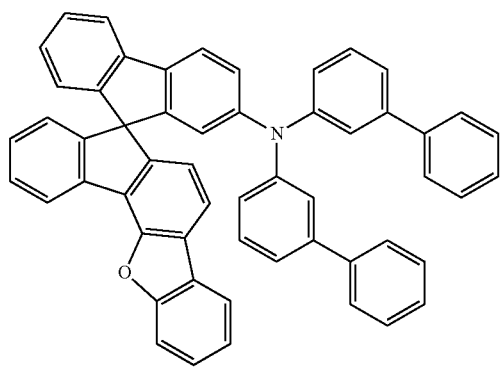
[Chemical Formula A-8]
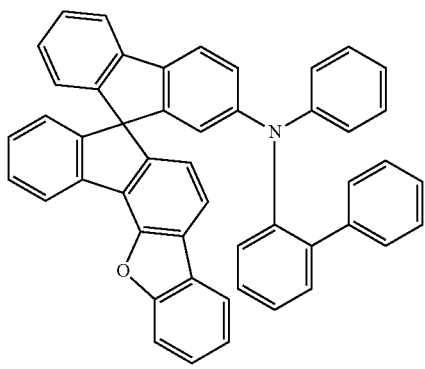
[Chemical Formula A-9]
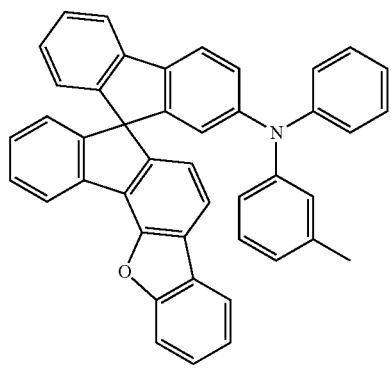
[Chemical Formula A-10]
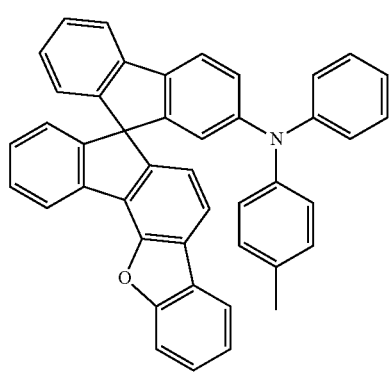
[Chemical Formula A-11]
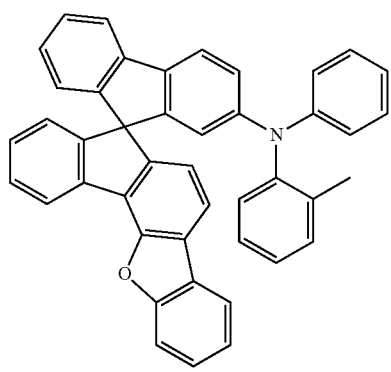

[Chemical Formula A-12]
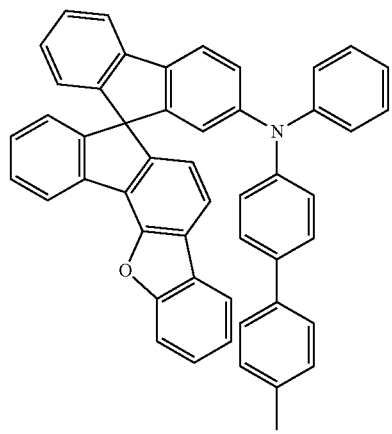
[Chemical Formula A-13]
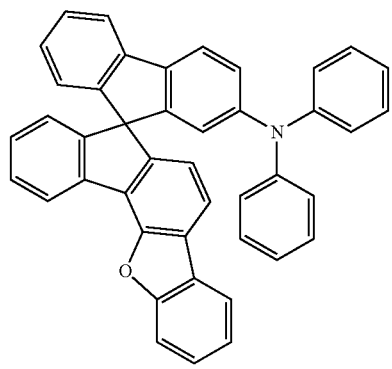
[Chemical Formula A-14]
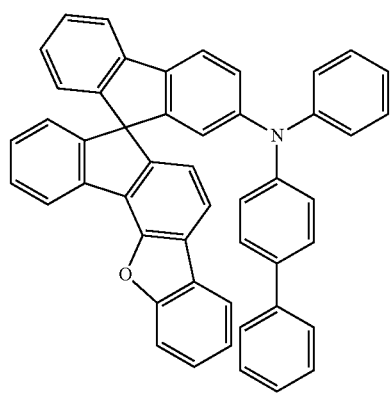
[Chemical Formula A-15]
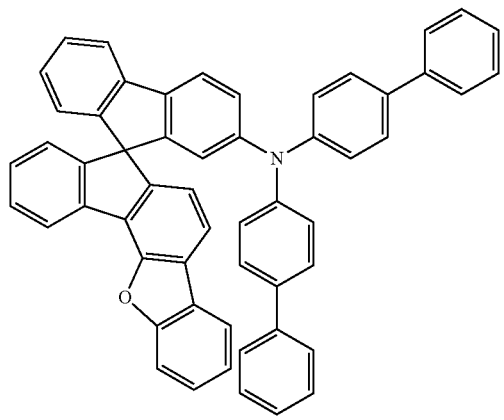
[Chemical Formula A-16]
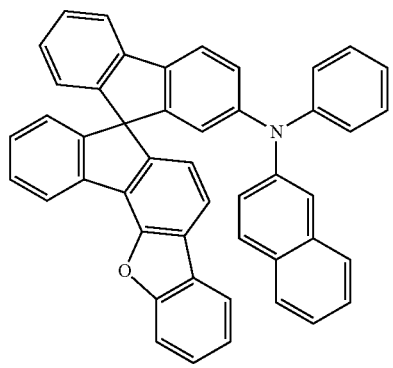
[Chemical Formula A-17]
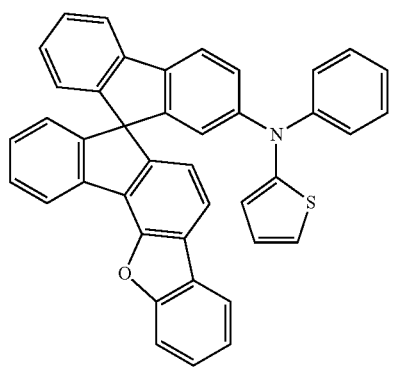
[Chemical Formula A-18]
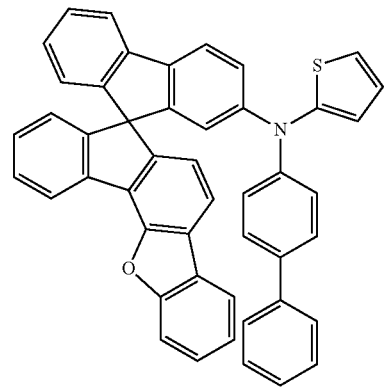

[Chemical Formula A-19]
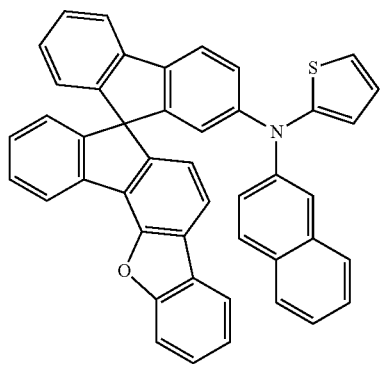
[Chemical Formula A-20]
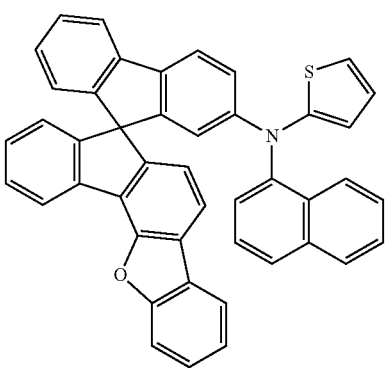
[Chemical Formula A-21]
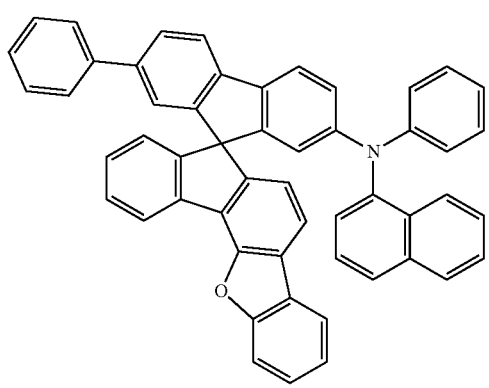
[Chemical Formula A-22]
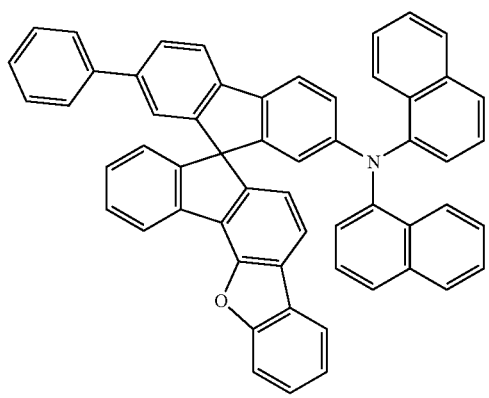
[Chemical Formula A-23]
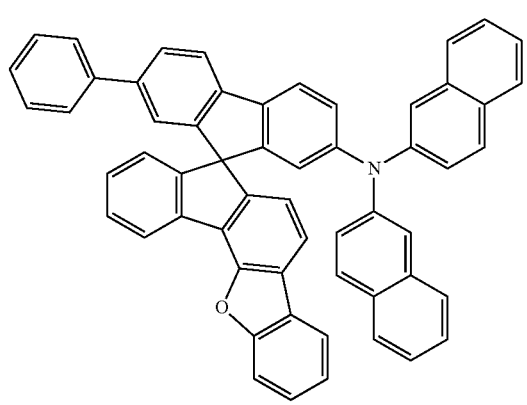
[Chemical Formula A-24]
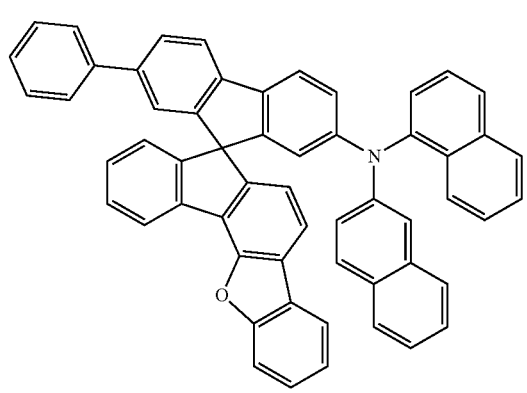
[Chemical Formula A-25]
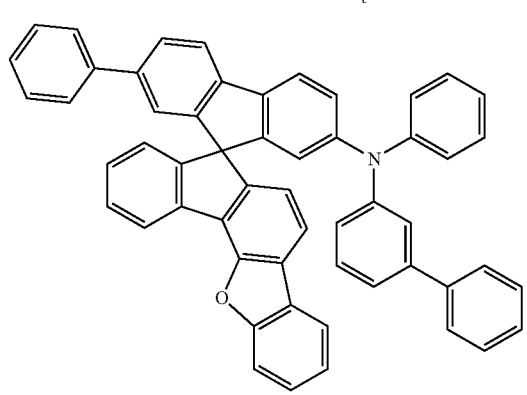
[Chemical Formula A-26]

[Chemical Formula A-27]
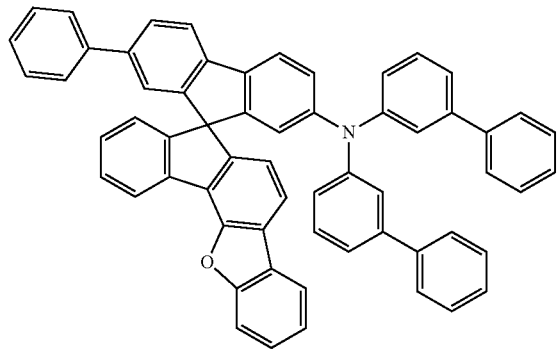
[Chemical Formula A-28]
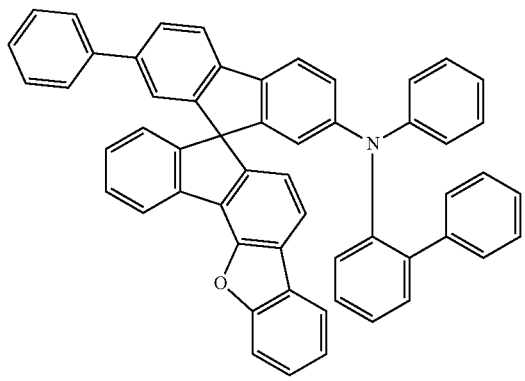
[Chemical Formula A-29]
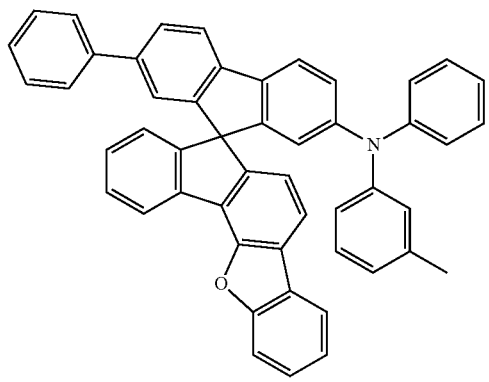
[Chemical Formula A-30]
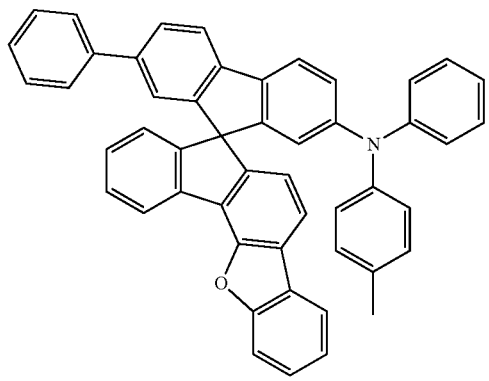
[Chemical Formula A-31]
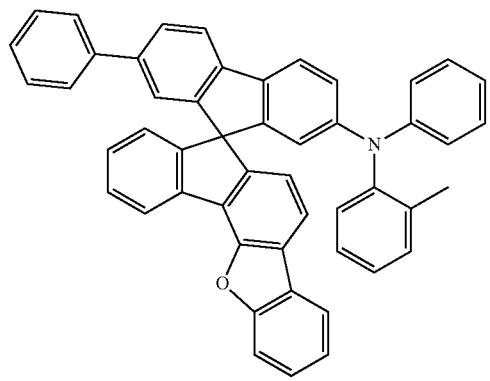
[Chemical Formula A-32]
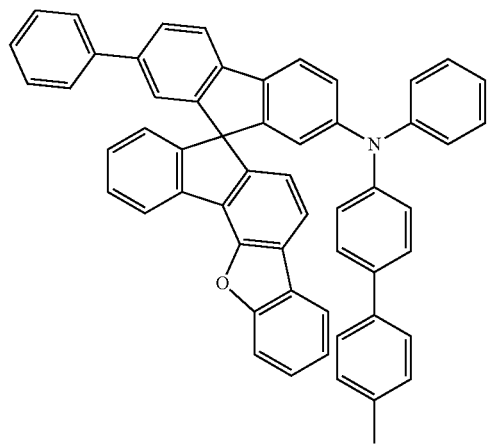
[Chemical Formula A-33]

[Chemical Formula A-34]
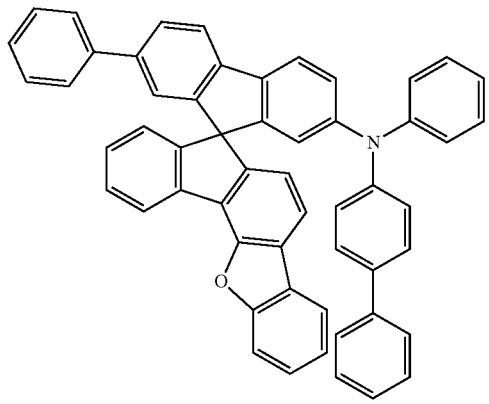
[Chemical Formula A-35]
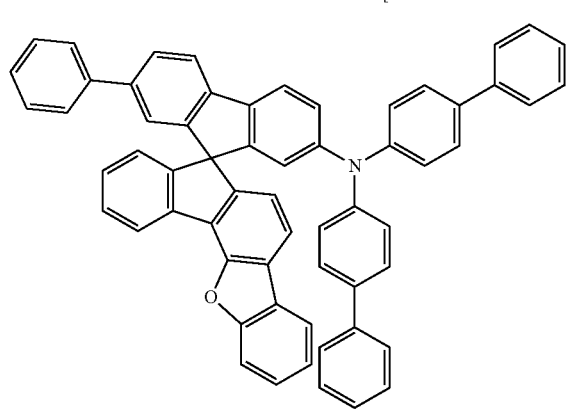
[Chemical Formula A-36]
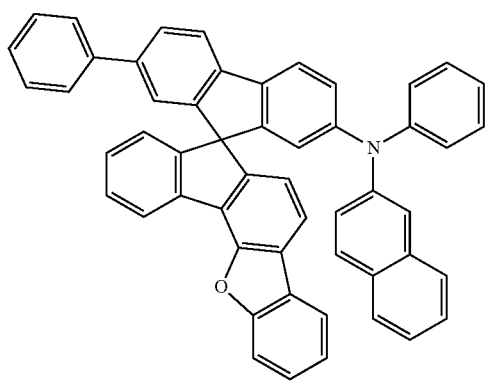
[Chemical Formula A-37]
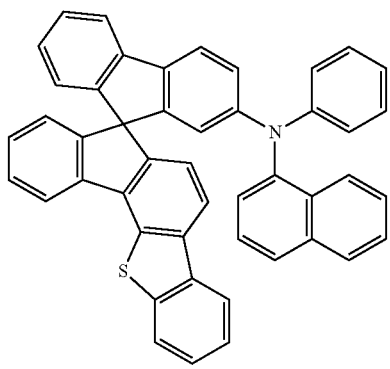
[Chemical Formula A-38]
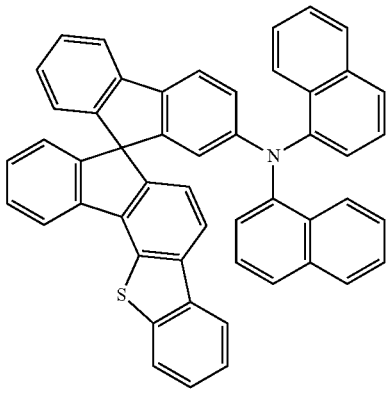
[Chemical Formula A-39]
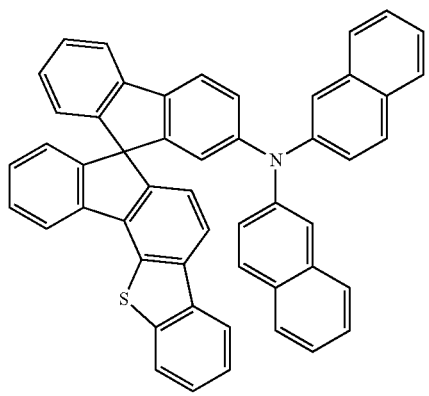
[Chemical Formula A-40]
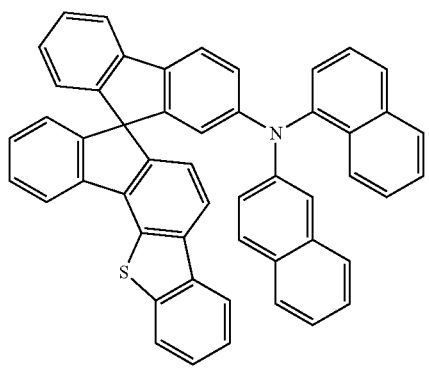
[Chemical Formula A-41]
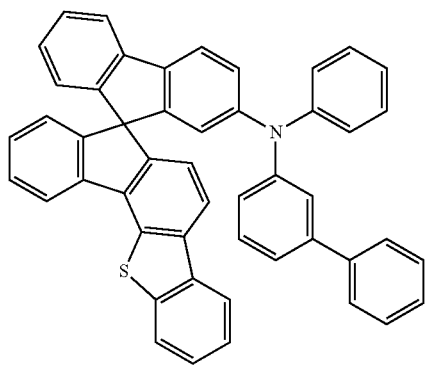

[Chemical Formula A-42]
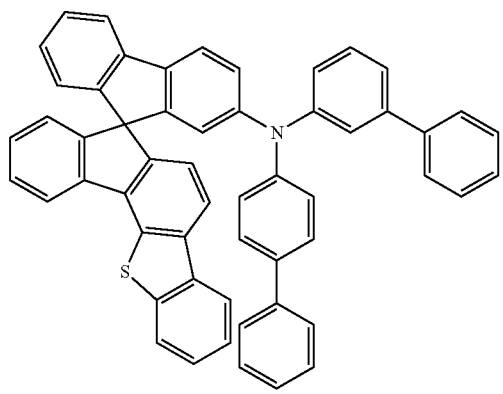
[Chemical Formula A-43]
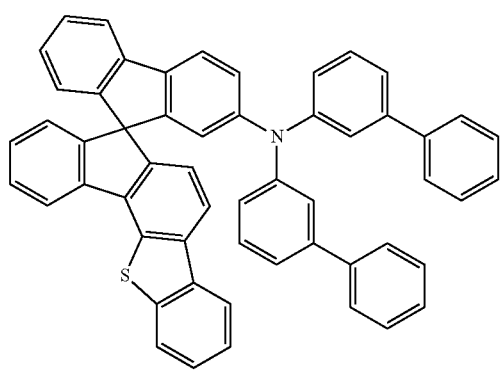
[Chemical Formula A-44]
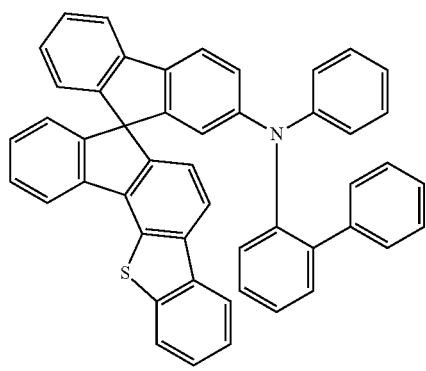
[Chemical Formula A-45]
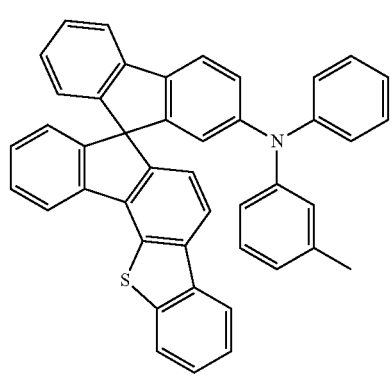
[Chemical Formula A-46]
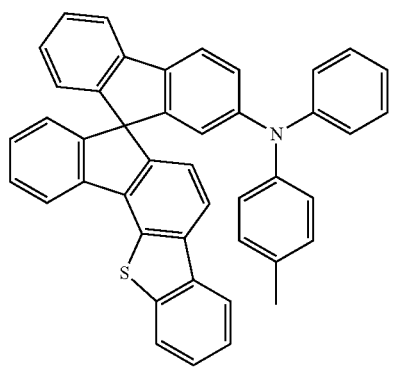
[Chemical Formula A-47]
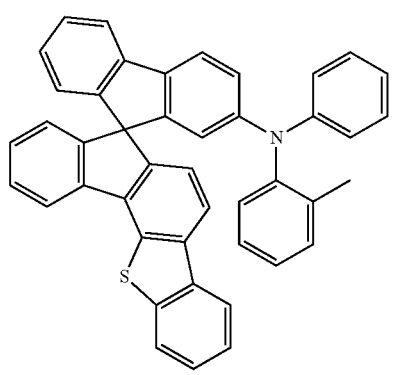
[Chemical Formula A-48]
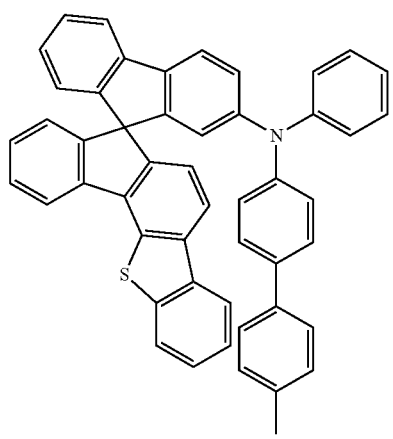
[Chemical Formula A-49]
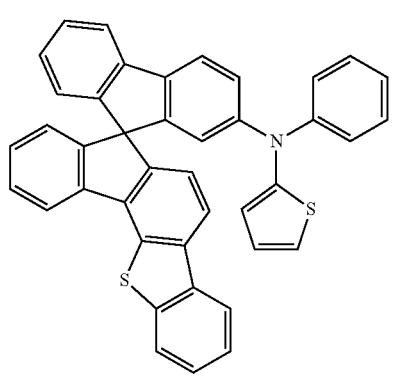

[Chemical Formula A-50]
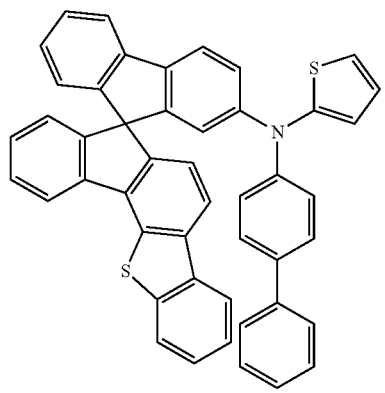
[Chemical Formula A-51]
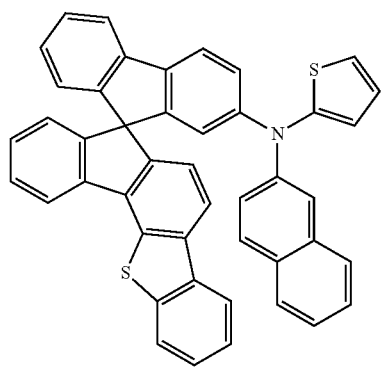
[Chemical Formula A-52]
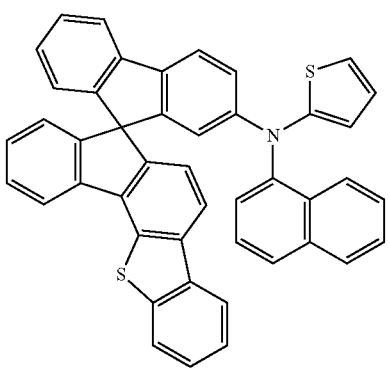
[Chemical Formula A-53]
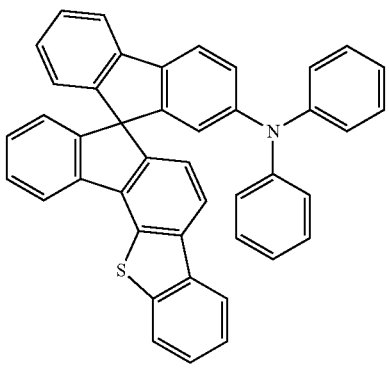
[Chemical Formula A-54]
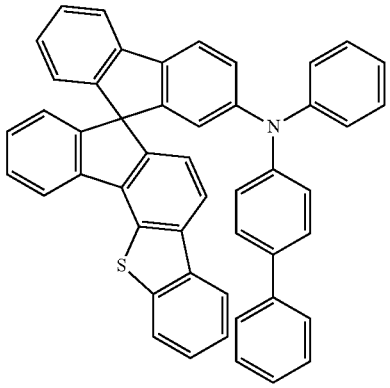
[Chemical Formula A-55]
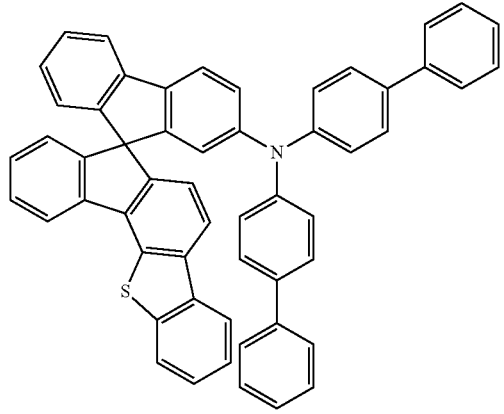
[Chemical Formula A-56]
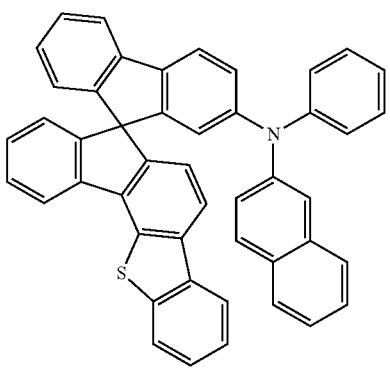
[Chemical Formula A-57]
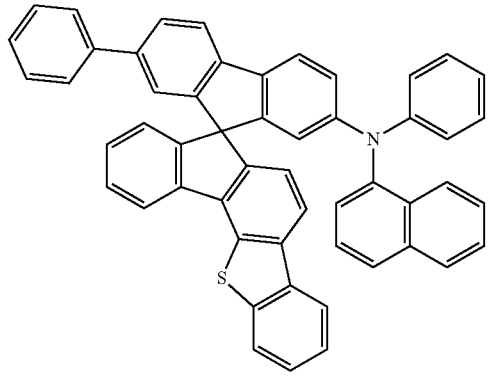

[Chemical Formula A-58]
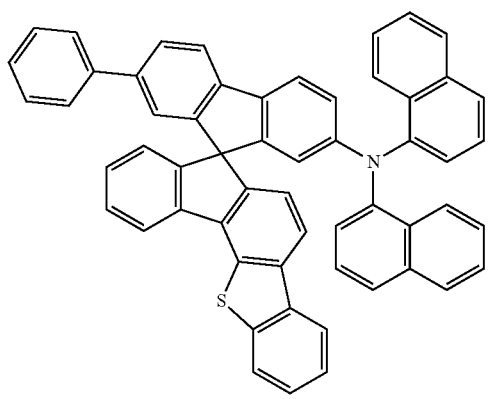
[Chemical Formula A-59]
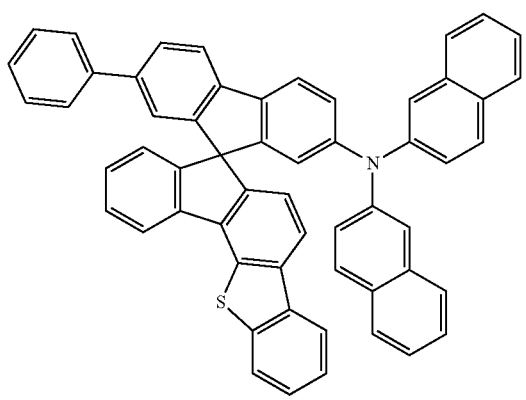
[Chemical Formula A-60]
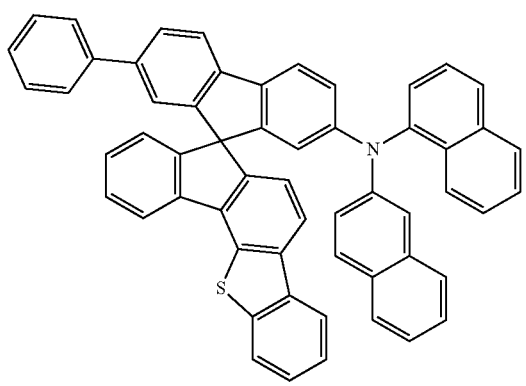
[Chemical Formula A-61]
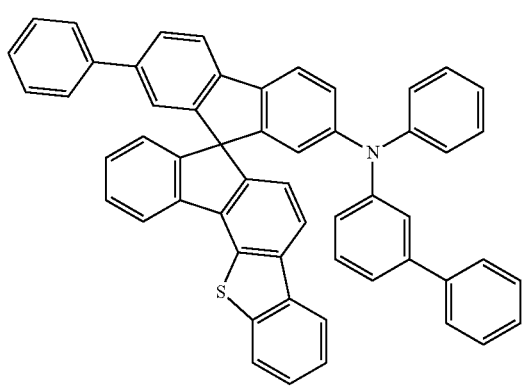
[Chemical Formula A-62]
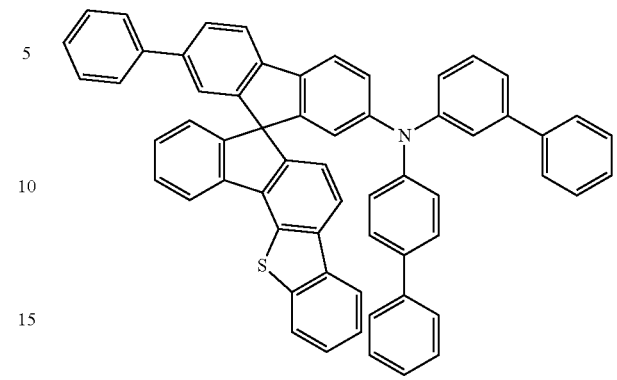
[Chemical Formula A-63]
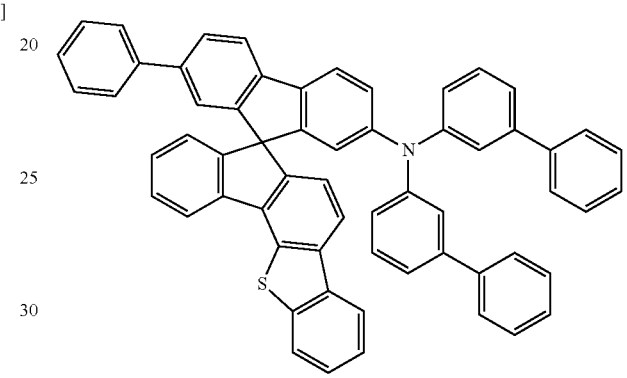
[Chemical Formula A-64]
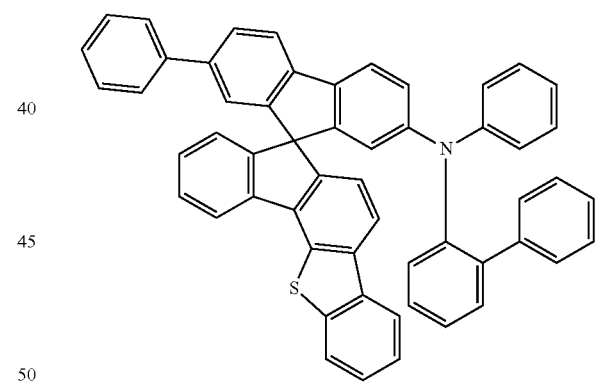
[Chemical Formula A-65]
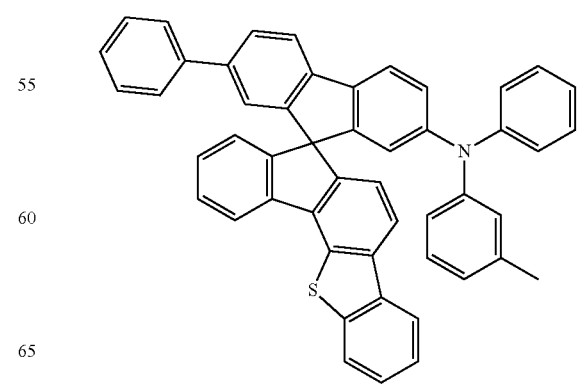

[Chemical Formula A-66]
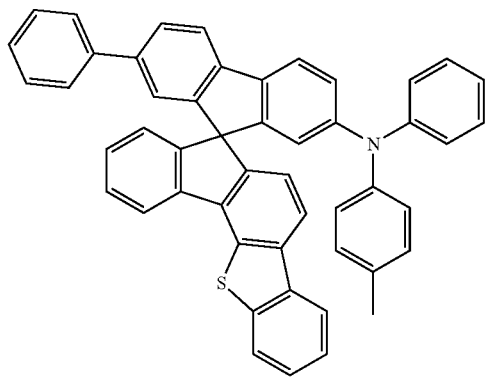
[Chemical Formula A-67]
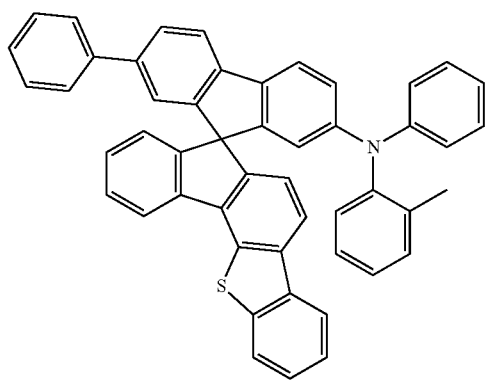
[Chemical Formula A-68]
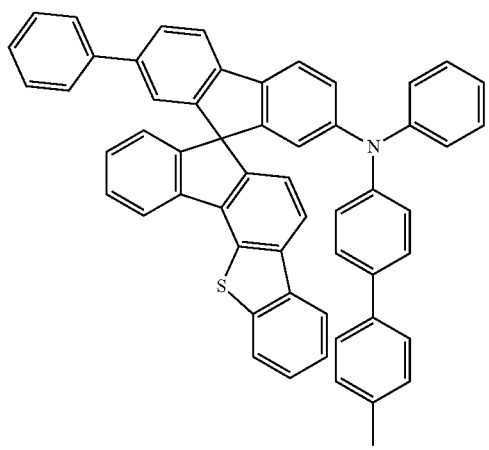
[Chemical Formula A-69]
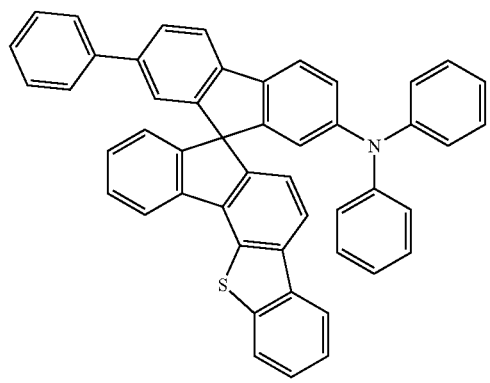
[Chemical Formula A-70]
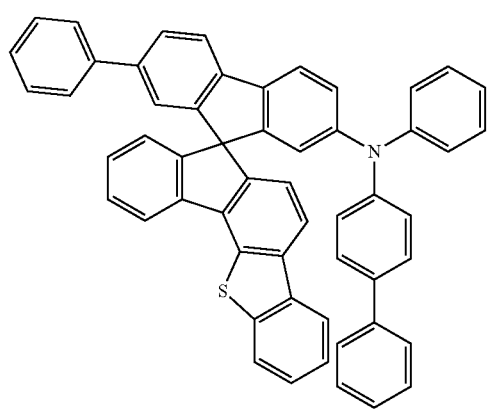
[Chemical Formula A-71]
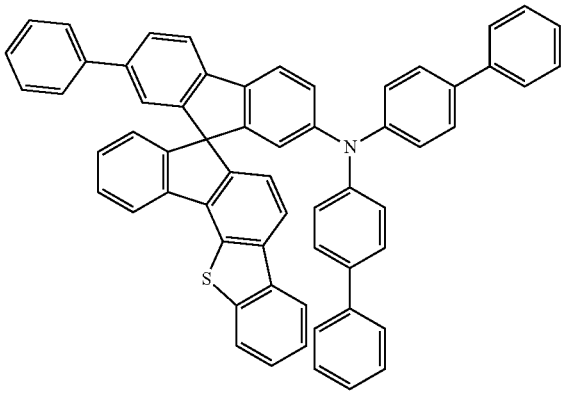

[Chemical Formula A-72]
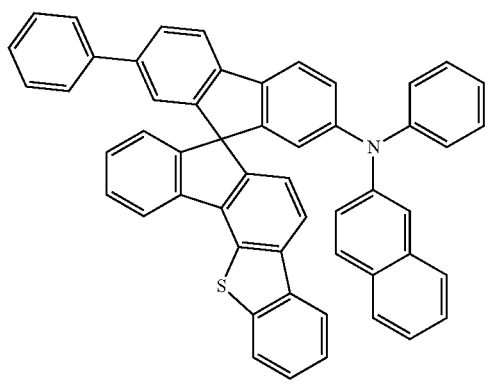
The compound for an organic optoelectronic device may be represented by one of the following Chemical Formulae B-1 to B-40.
[Chemical Formula B-1]
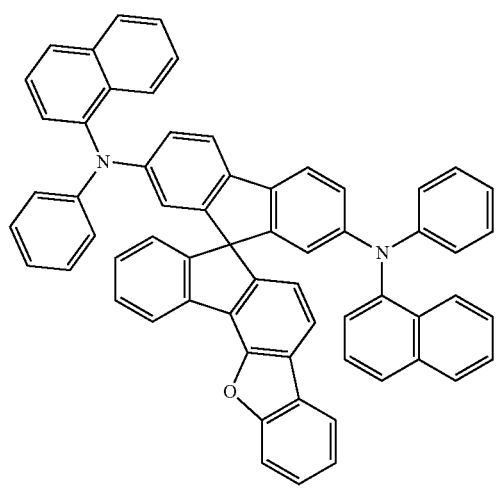
[Chemical Formula B-2]
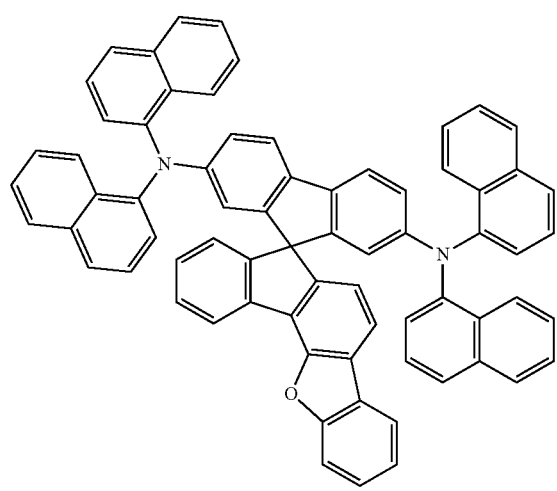
[Chemical Formula B-3]
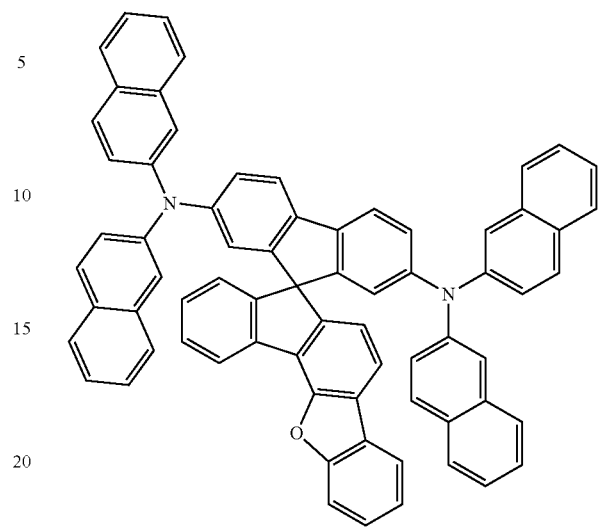
[Chemical Formula B-4]
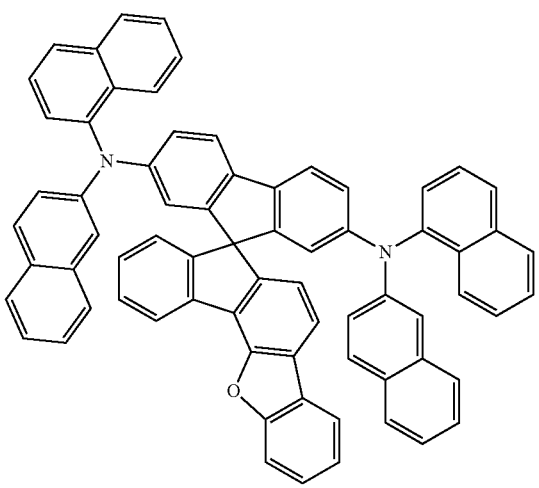
[Chemical Formula B-5]
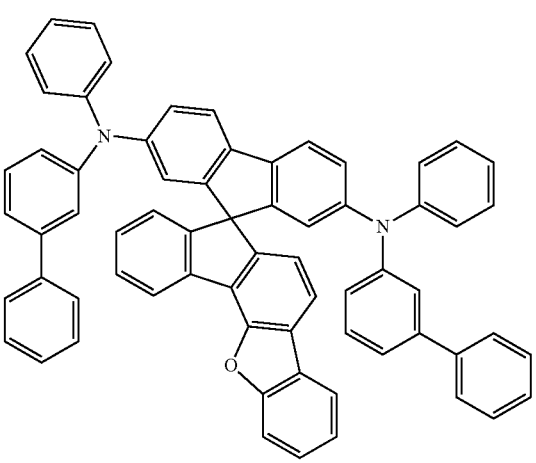

[Chemical Formula B-6]
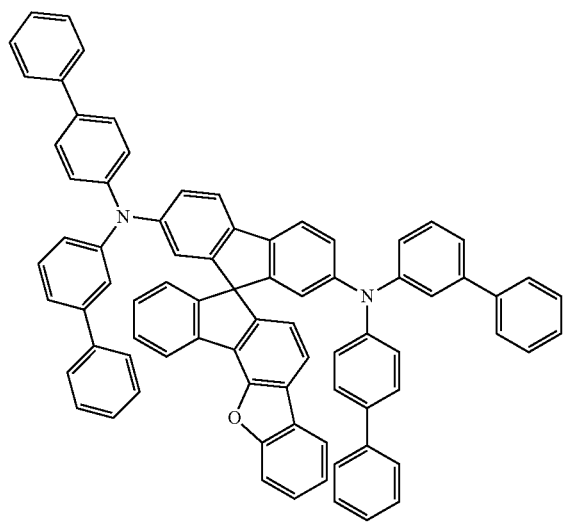
[Chemical Formula B-7]
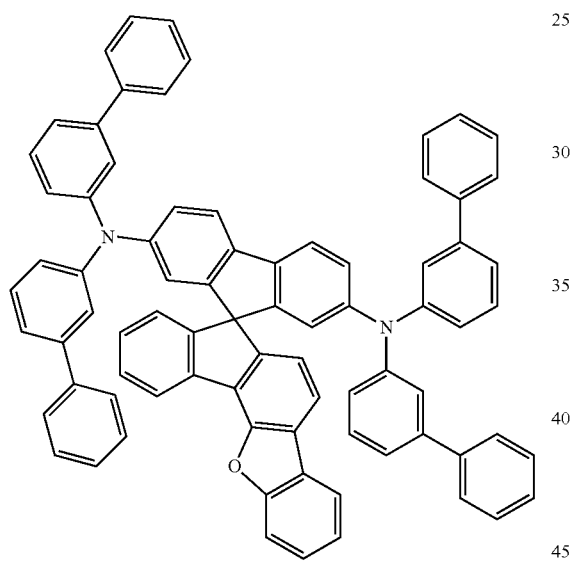
[Chemical Formula B-8]
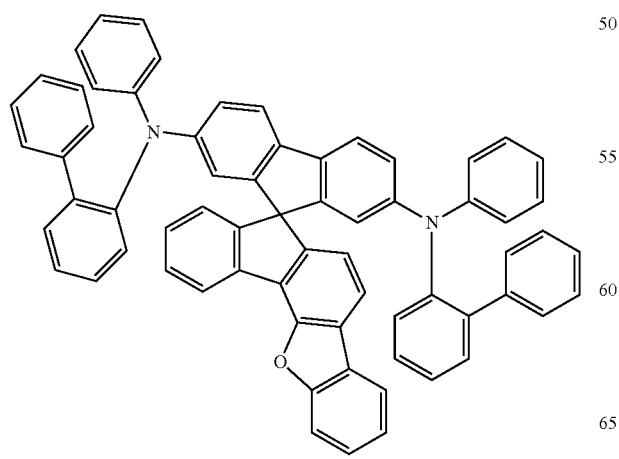
[Chemical Formula B-9]
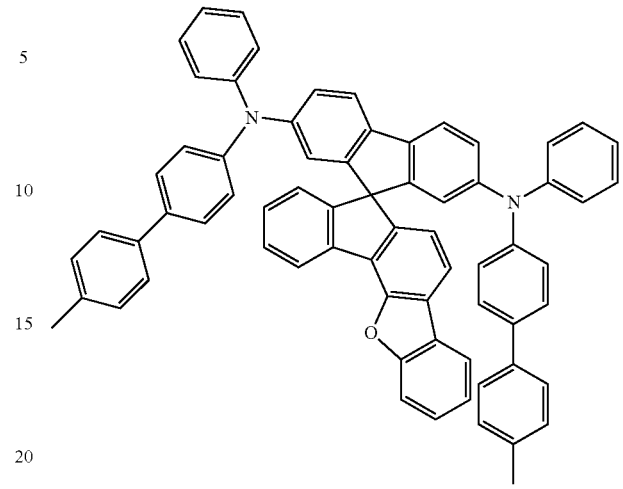
[Chemical Formula B-10]
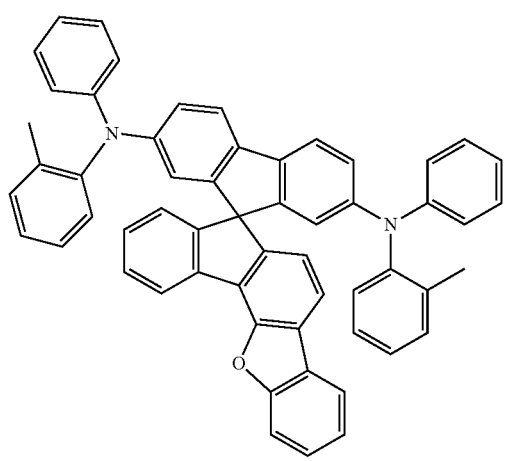
[Chemical Formula B-11]
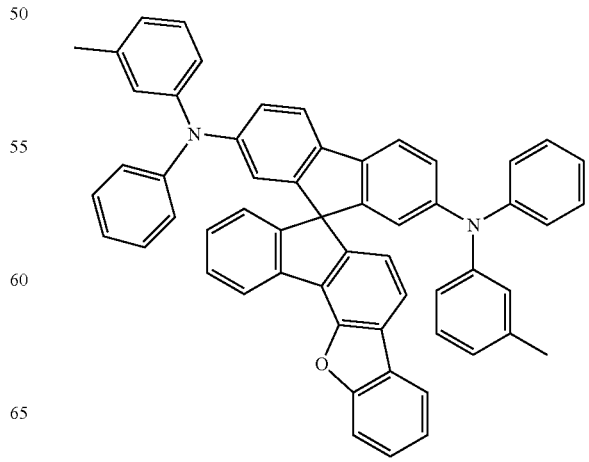

[Chemical Formula B-12]
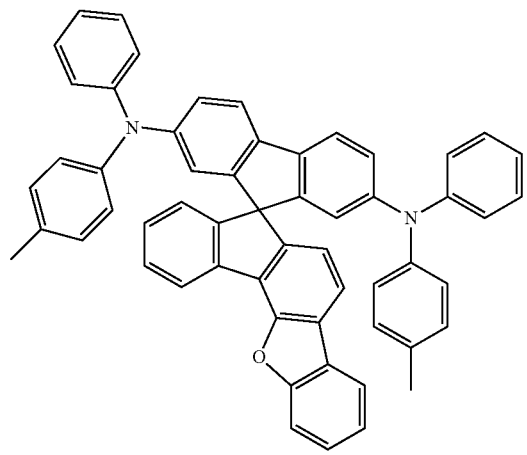
[Chemical Formula B-13]
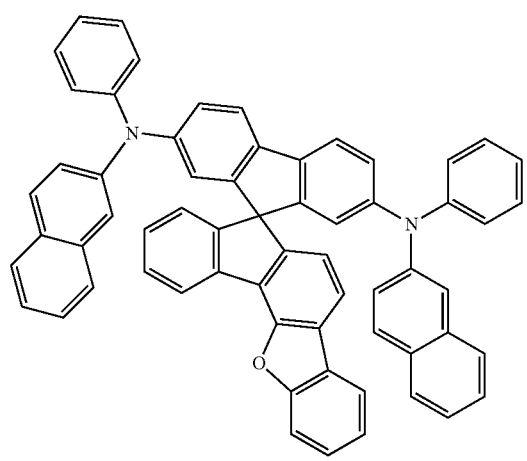
[Chemical Formula B-14]
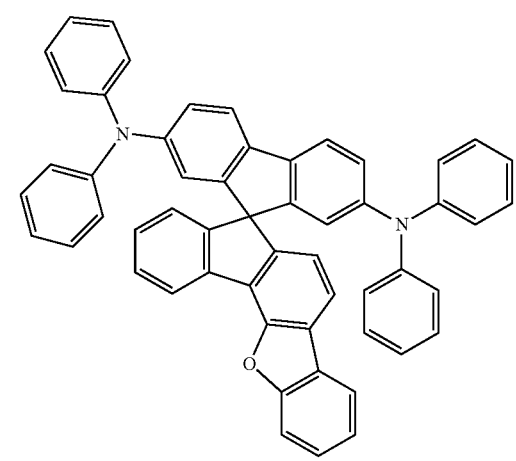
[Chemical Formula B-15]
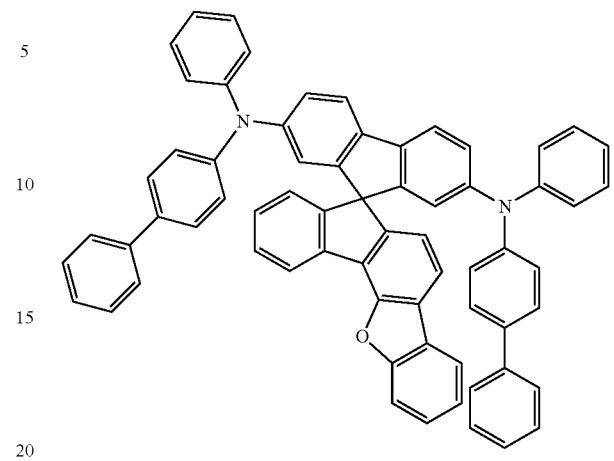
[Chemical Formula B-16]
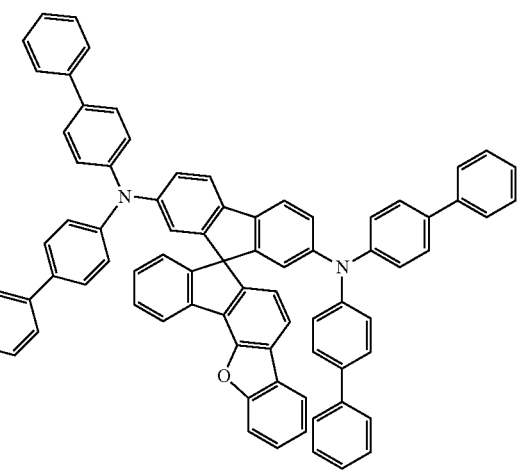
[Chemical Formula B-17]
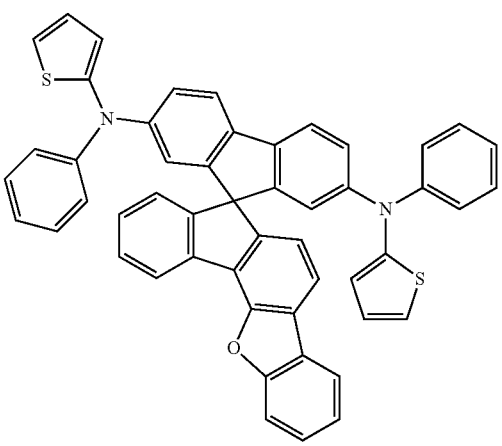

[Chemical Formula B-18]
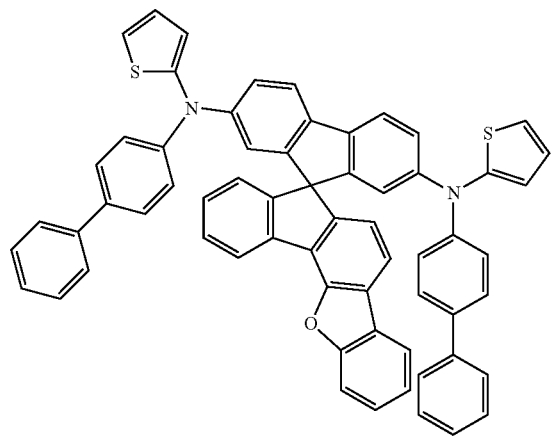
[Chemical Formula B-19]
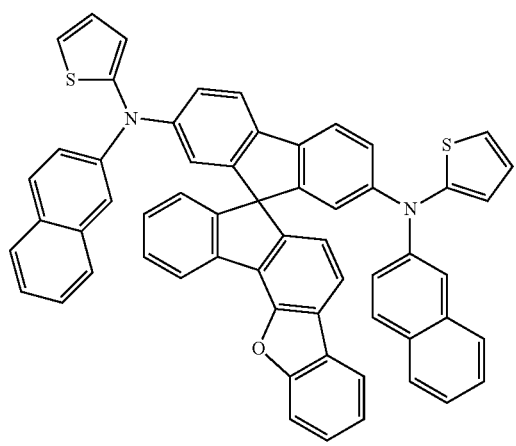
[Chemical Formula B-20]
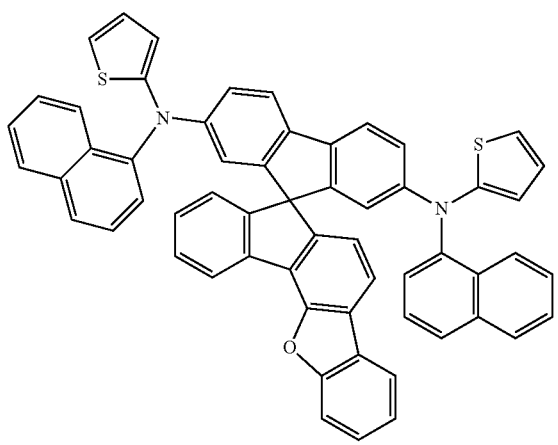
[Chemical Formula B-21]
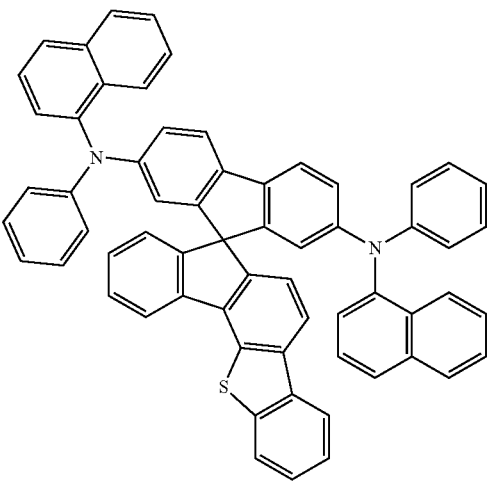
[Chemical Formula B-22]
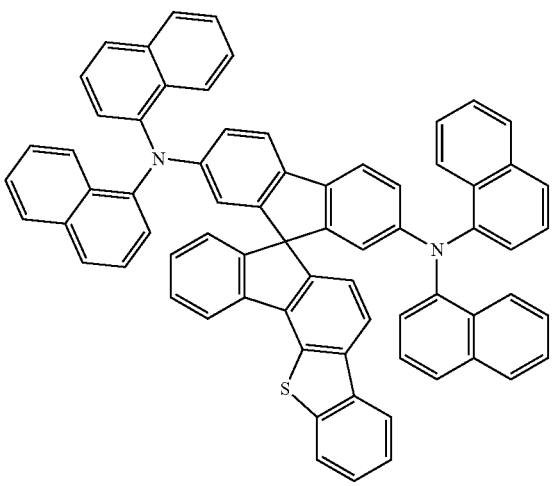
[Chemical Formula B-23]
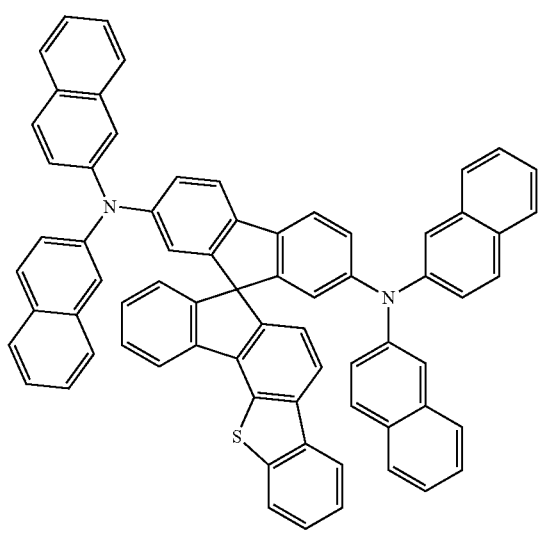

[Chemical Formula B-24]
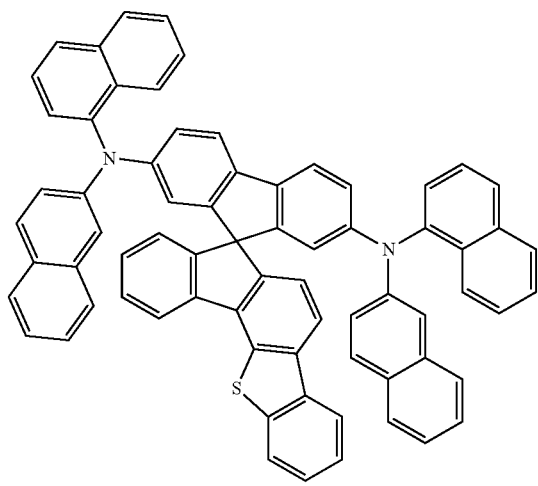
[Chemical Formula B-25]
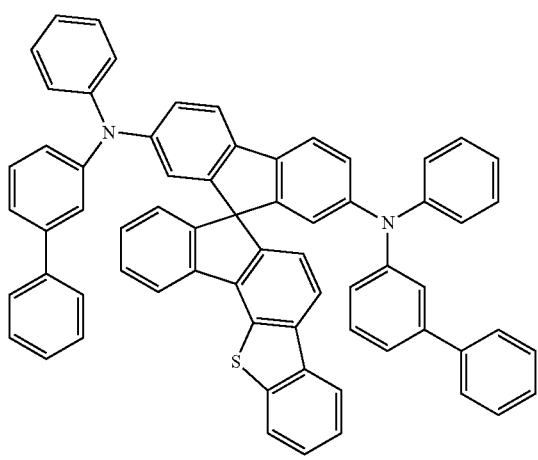
[Chemical Formula B-26]
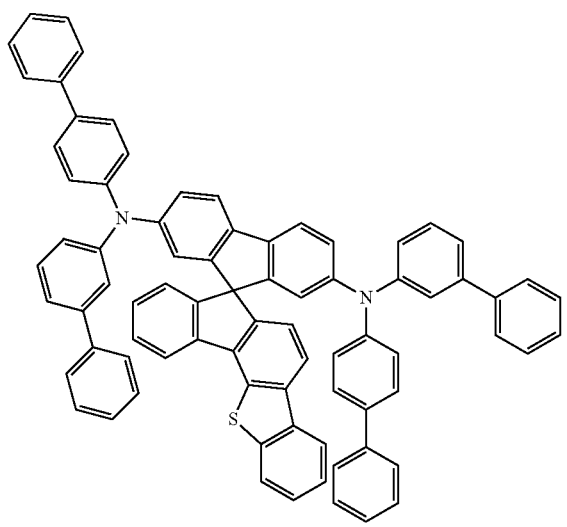
[Chemical Formula B-27]
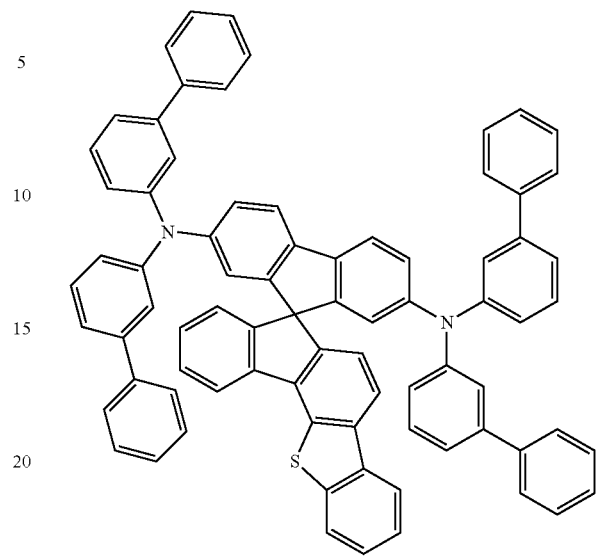
[Chemical Formula B-28]
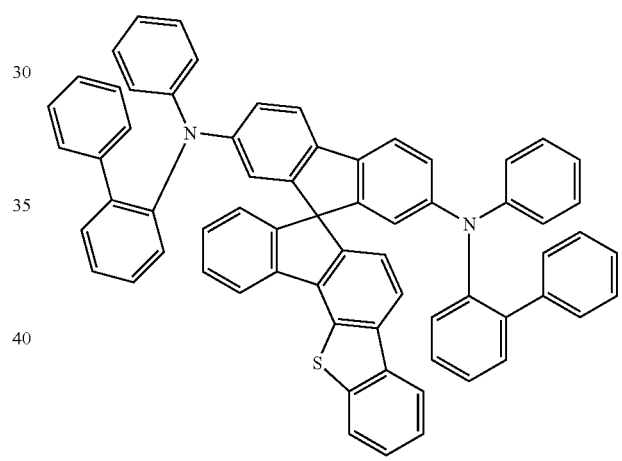
[Chemical Formula B-29]
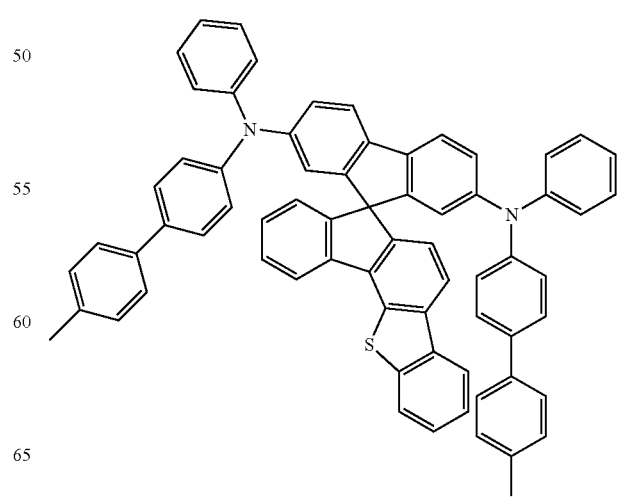

[Chemical Formula B-30]
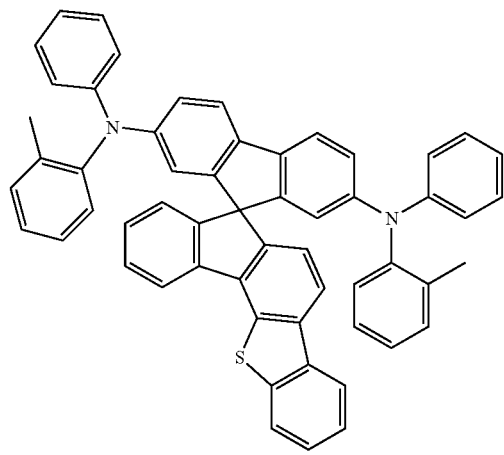
[Chemical Formula B-33]
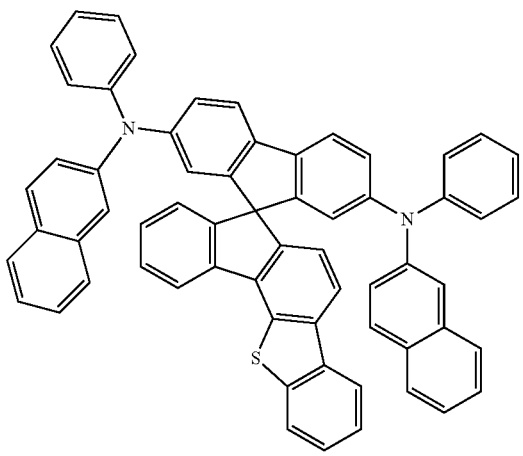
[Chemical Formula B-31]
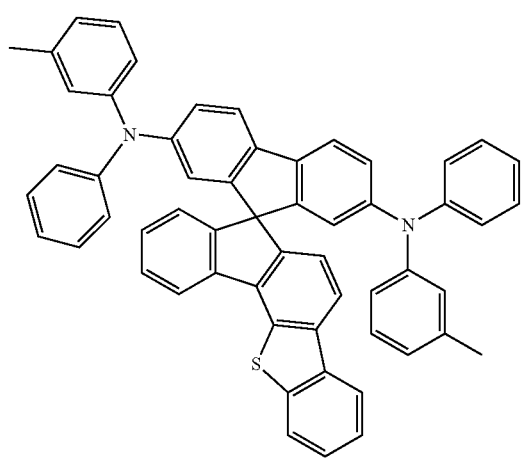
[Chemical Formula B-34]
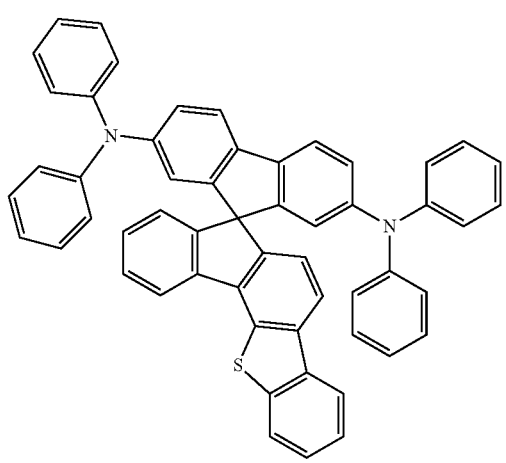
[Chemical Formula B-32]
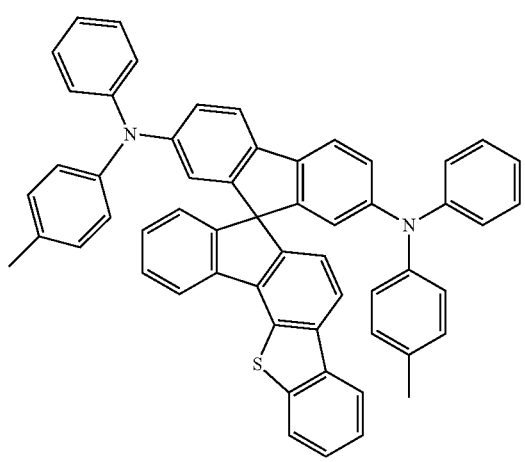
[Chemical Formula B-35]
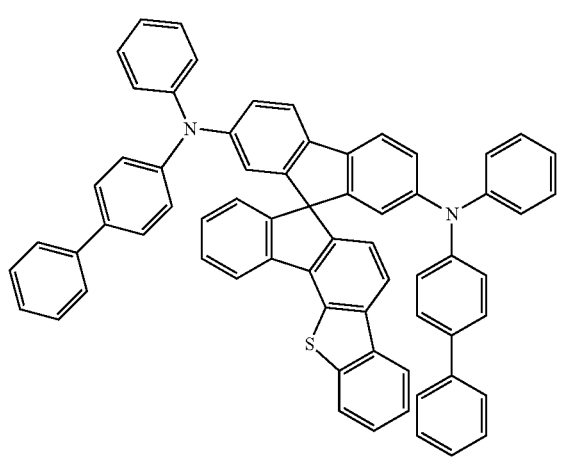

[Chemical Formula B-36]

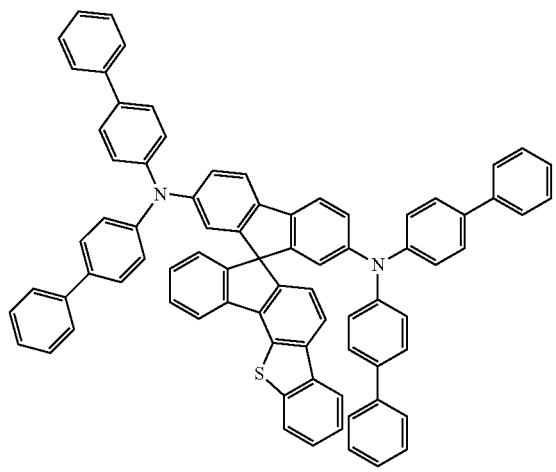

[Chemical Formula B-37]

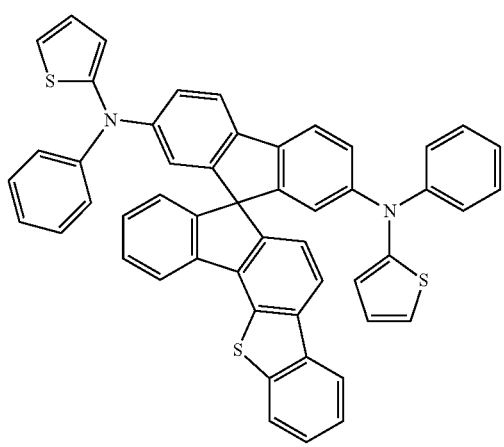

[Chemical Formula B-38]

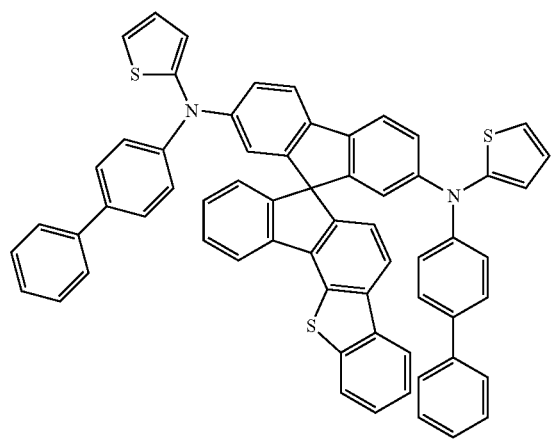

[Chemical Formula B-39]

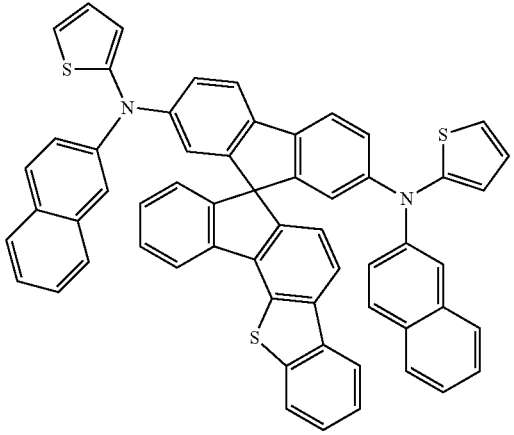

[Chemical Formula B-40]

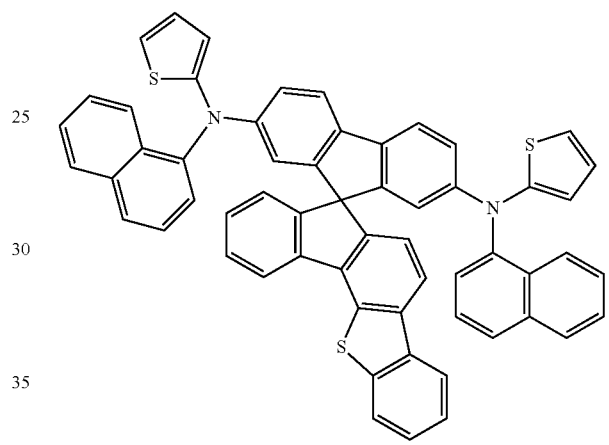

The compound for an organic optoelectronic device may have triplet exciton energy (T1) of greater than or equal to about 2.0 eV.

The organic optoelectronic device may be selected from an organic photoelectric device, an organic light emitting diode, an organic solar cell, an organic transistor, an organic photo-conductor drum, and an organic memory device.

In another embodiment of the present invention, provided is an organic light emitting diode including an anode, a cathode, and at least one organic thin layer interposed between the anode and cathode, wherein at least one of the organic thin layers includes the above compound for an organic optoelectronic device.

The organic thin layer may be selected from an emission layer, a hole transport layer, a hole injection layer, an electron transport layer, an electron injection layer, a hole blocking layer, and a combination thereof.

The compound for an organic optoelectronic device may be included in a hole transport layer (HTL) or a hole injection layer (HIL).

The compound for an organic optoelectronic device may be included in an emission layer.

The compound for an organic optoelectronic device may be used as a phosphorescent or fluorescent host material in an emission layer.

In yet another embodiment of the present invention, a display device including the above organic light emitting diode is provided.

Advantageous Effects

A compound having high hole or electron transport properties, film stability, thermal stability, and high triplet exciton energy may be provided.

Such a compound may be used as a hole injection/transport material, host material, or electron injection/transport material of an emission layer. An organic optoelectronic device using the same has improved life-span characteristic high luminous efficiency at a low driving voltage due to excellent electrochemical and thermal stability.

Figure 1:
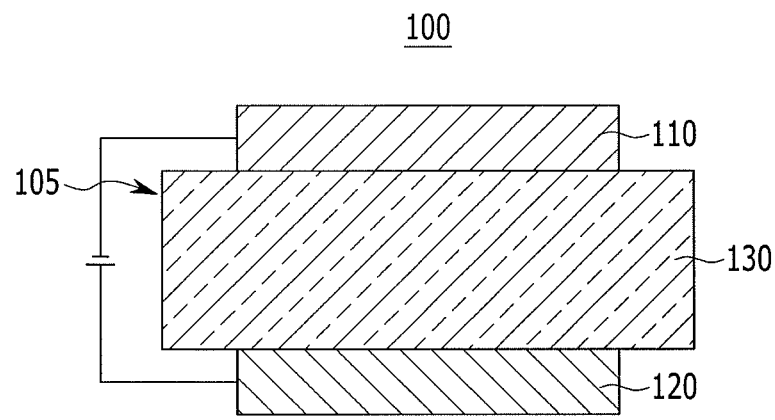
FIGS. 1 to 5 are cross-sectional views showing organic light emitting diodes according to various embodiments of the present invention including the compound for an organic optoelectronic device according to one embodiment of the present invention.

| 100 | organic light emitting diode | 110 | cathode |
|---|---|---|---|
| 120 | anode | 105 | organic thin film |
| 130 | emission layer | 140 | hole transport layer (HTL) |
| 150 | electron transport layer (ETL) | 160 | electron injection layer (EIL) |
| 170 | hole injection layer (HIL) | 230 | emission layer + electron transport layer (ETL) |

MODE FOR INVENTION

Hereinafter, embodiments of the present invention are described in detail. However, these embodiments are exemplary, and this disclosure is not limited thereto.

As used herein, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, instead of at least one hydrogen of a substituent or a compound.

The two adjacent substituent selected from the substituted a halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused to form a ring.

In the present specification, when specific definition is not otherwise provided, "hetero" refers to one including 1 to 3 hetero atoms selected from N, O, S, and P, and remaining carbons in one compound or substituent.

In the present specification, when a definition is not otherwise provided, the term "combination thereof" refers to at least two substituents bound to each other by a linker, or at least two substituents condensed to each other.

In the present specification, when a definition is not otherwise provided, "alkyl group" refers to an aliphatic hydrocarbon group. The alkyl group may be "a saturated alkyl group" without any double bond or triple bond. The alkyl group may be branched, linear or cyclic.

The "alkenylene group" refers to a functional group of at least one carbon-carbon double bond of at least two carbons, and the "alkynylene group" refers to a functional group of at least one carbon-carbon triple bond of at least two carbons.

The alkyl group may be a C1 to C20 alkyl group. More specifically, the alkyl group may be a C1 to C10 alkyl group or a C1 to C6 alkyl group.

For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

"Aromatic group" refers to a cyclic functional group where all elements have p-orbitals, and these p-orbitals forms conjugation. Specific examples are aryl group and a heteroaryl group.

"Aryl group" includes monocyclic or fused ring polycyclic (i.e., rings sharing adjacent pairs of carbon atoms) groups.

"Heteroaryl group" refers to aryl group including 1 to 3 hetero atoms selected from N, O, S, and P, and remaining carbons. When the heteroaryl group is a fused ring, each ring may include 1 to 3 hetero atoms.

As used herein, the carbazole-based derivative may refer to a substituted structure where a nitrogen atom of a substituted or unsubstituted carbazolyl group is substituted with a hetero atom except nitrogen, or carbon. Specific examples may be dibenzofuran (dibenzofuranyl group), dibenzothiophene (dibenzothiopheneyl group), fluorene (fluorenyl group), and the like.

In the present specification, hole characteristics refer to characteristics that holes formed in the anode is easily injected into the emission layer and transported in the emission layer due to conductive characteristics according to HOMO level.

Electron characteristics refer to characteristics that electron formed in the cathode is easily injected into the emission layer and transported in the emission layer due to conductive characteristics according to LUMO level.

A compound for an organic optoelectronic device according to one embodiment of the present invention may have a structure that at least one amine group is combined with a bifluorene core having a spiro structure.

In addition, a part of the core having a spiro structure may be a fused ring.

The core structure may be used as a light emitting material, a hole injection material, or a hole transport material for an organic optoelectronic device. Particularly, the core structure may be more appropriate for a hole injection material or a hole transport material.

The compound for an organic optoelectronic device includes a core part and various substituents for a substituent for substituting the core part and thus may have various energy bandgaps.

When the compound having an appropriate energy level depending on a substituent is used to manufacture an organic optoelectronic device, the compound reinforces hole transport capability or electron transport capability and thus, brings about excellent effects in terms of efficiency and a driving voltage, and also, has excellent electrochemical and thermal stability and thus, may improve life-span characteristics of the organic optoelectronic device.

In one embodiment of the present invention, a compound for an organic optoelectronic device represented by a combination of the following Chemical Formula 1 and Chemical Formula 2 is provided.

[Chemical Formula 1]

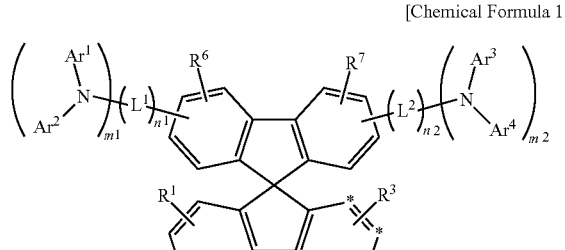

[Chemical Formula 2]

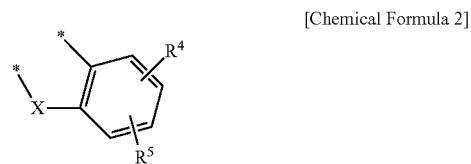

In the above Chemical Formulae 1 and 2, X is —O—, —S—, —S(O)— or —S(O)$_2$—, $Ar^1$ to $Ar^4$ are independently a substituted or unsubstituted C6 to C30 aryl group, or a substituted or unsubstituted C2 to C30 heteroaryl group, $L^1$ and $L^2$ are independently a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m1 and m2 are independently integers of 0 or 1, one of m1 and m2 is 1, n1 and n2 are independently integers ranging from 0 to 3, $R^1$ to $R^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group, and two *s of the above Chemical Formula 2 are bonded with the adjacent two *s of the above Chemical Formula 1 to form a fused ring.

The X may be —O—, —S—, —S(O)— or —S(O)$_2$—. Since the —O—, —S—, —S(O)— or —S(O)$_2$— has a polar group and thus, is able to interact with an electrode, charges may be easily injected.

When the arylamine group (or a heteroarylamine group) is combined with a bifluorene group of the core having a spiro structure, charge mobility may be increased, and thus, a driving voltage of a device may be deteriorated.

In addition, the compound has steric hindrance and thus, may be suppressed from crystallization due to low interaction among molecules. Accordingly, a yield of manufacturing a device may be improved. In addition, life-span characteristics of the device may be improved.

Furthermore, the compound has a relatively large molecular weight and thus, may be suppressed from decomposition during the deposition.

More specifically, the above Chemical Formula 1 may be represented by the following Chemical Formula 3.

[Chemical Formula 3]

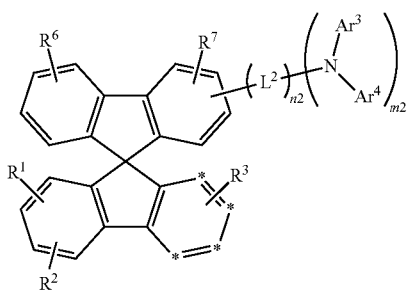

In the above Chemical Formula 3, $Ar^3$ and $Ar^4$ are independently a substituted or unsubstituted C6 to C30 aryl group, or a substituted or unsubstituted C2 to C30 heteroaryl group, $L^2$ is a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m2 is 1, n2 is an integer ranging from 0 to 3, $R^1$ to $R^3$, $R^6$ or $R^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group, and two *s of the above Chemical Formula 2 are bonded with the adjacent two *s of the above Chemical Formula 3 to form a fused ring.

More specifically, the compound for an organic optoelectronic device may be represented by the following Chemical Formula 4. When a fused ring is positioned as shown in the following Chemical Formula 4, high Tg may be obtained like spiro fluorene, and introduction of a dibenzofuran group may increase mobility of the compound and hole mobility.

[Chemical Formula 4]

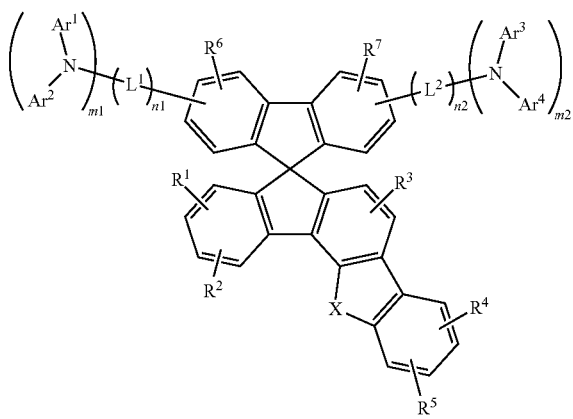

In the above Chemical Formula 4, X is —O—, —S—, —S(O)— or —S(O)$_2$—, $Ar^1$ to $Ar^4$ are independently a substituted or unsubstituted C6 to C30 aryl group, or a substituted or unsubstituted C2 to C30 heteroaryl group, $L^1$ and $L^2$ are independently a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m1 and m2 are independently integers of 0 or 1, one of m1 and m2 is 1, n1 and n2 are independently integers ranging from 0 to 3, and $R^1$ to $R^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

More specifically, the compound for an organic optoelectronic device may be represented by the following Chemical Formula 5.

[Chemical Formula 5]

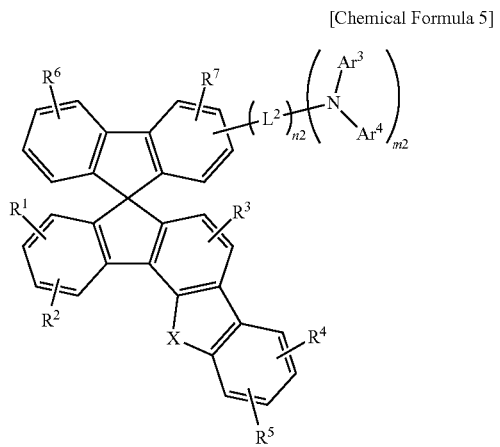

In the above Chemical Formula 5, $Ar^3$ and $Ar^4$ are independently a substituted or unsubstituted C6 to C30 aryl group, or a substituted or unsubstituted C2 to C30 heteroaryl group, $L^2$ is a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m2 is 1, n2 is an integer ranging from 0 to 3, and $R^1$ to $R^7$ are independently hydrogen, deuterium, a substituted or unsubstituted C1 to C10 alkyl group, a substituted or unsubstituted C6 to C30 aryl group, or a substituted or unsubstituted C2 to C30 to heteroaryl group.

The $L^1$ and $L^2$ may be selectively adjusted to determine the entire conjugation length of the compound, and thereby energy level may be adjusted and Tg may be increased.

Specific examples of the $L^1$ and $L^2$ may be a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a thiopheneylene group, a furan group, a vinyl group, and the like.

The $Ar^1$ to $Ar^4$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiopheneyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiopheneyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but is not limited thereto.

The compound for an organic optoelectronic device may have light emission, hole or electron characteristics; film stability; thermal stability, and high triplet exciton energy (T1) due to the substituent.

More specifically, the compound for an organic optoelectronic device may be represented by one of the following Chemical Formulae A-1 to A-72, but is not limited thereto.

[Chemical Formula A-1]

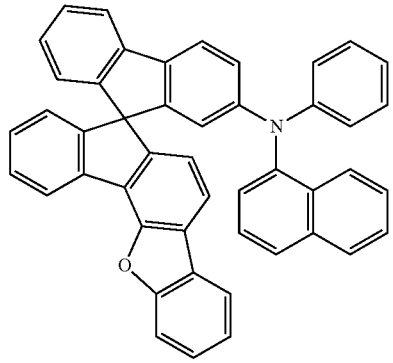

[Chemical Formula A-2]

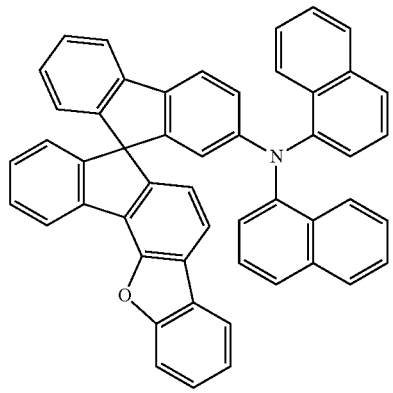

[Chemical Formula A-3]
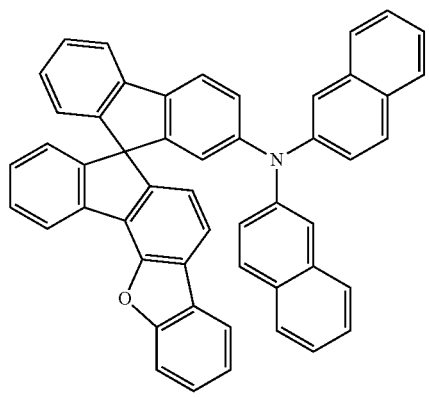
[Chemical Formula A-4]
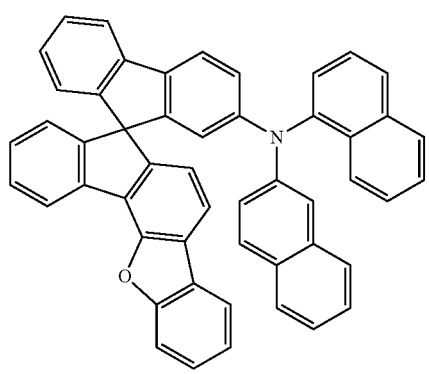
[Chemical Formula A-5]
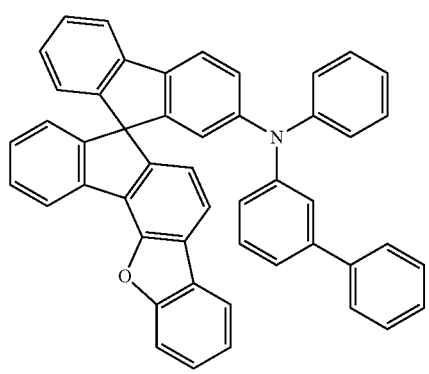
[Chemical Formula A-6]
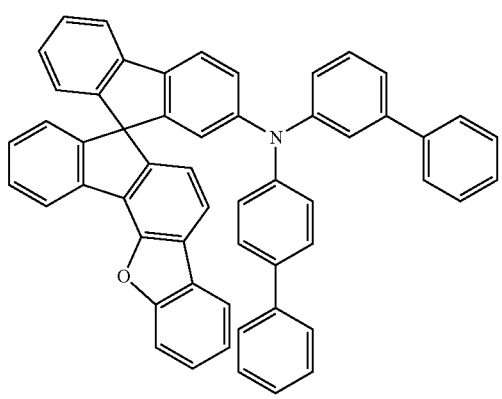
[Chemical Formula A-7]
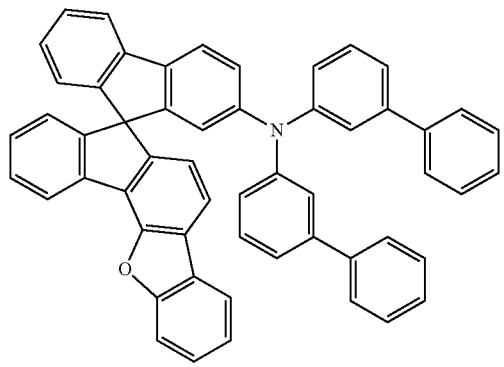
[Chemical Formula A-8]
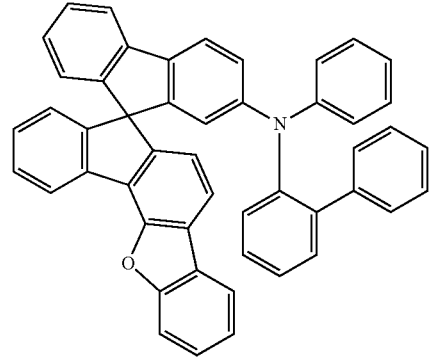
[Chemical Formula A-9]
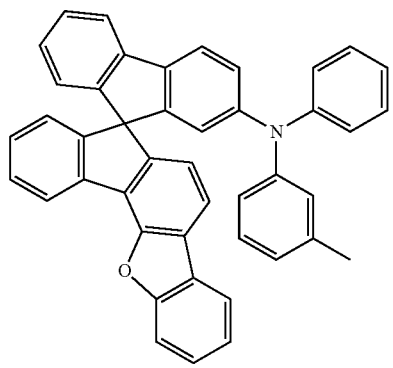
[Chemical Formula A-10]
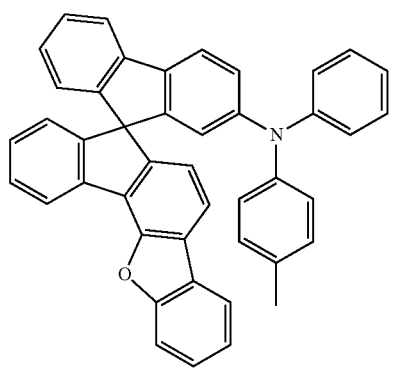

[Chemical Formula A-11]
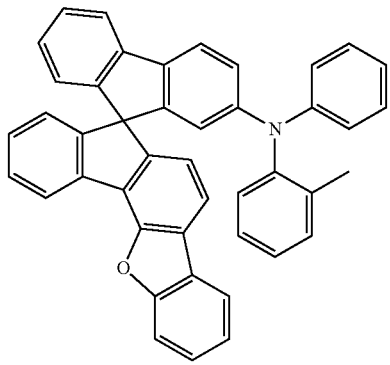
[Chemical Formula A-12]
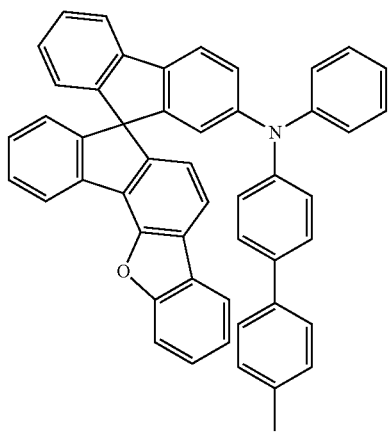
[Chemical Formula A-13]
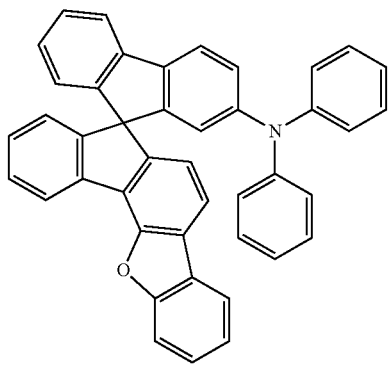
[Chemical Formula A-14]
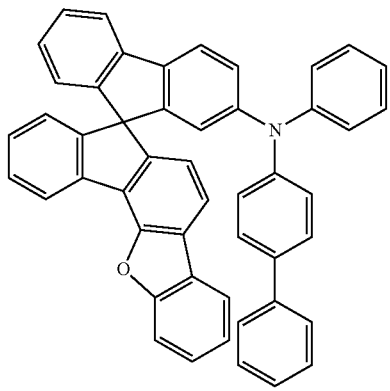
[Chemical Formula A-15]
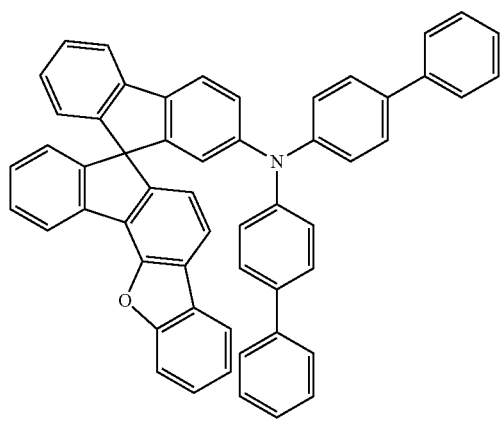
[Chemical Formula A-16]
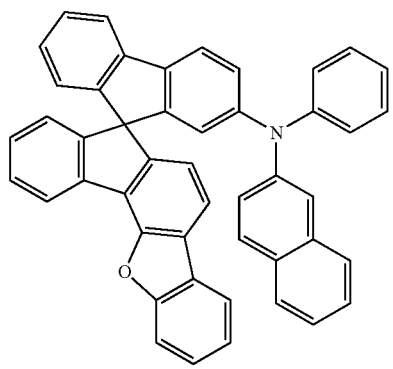
[Chemical Formula A-17]
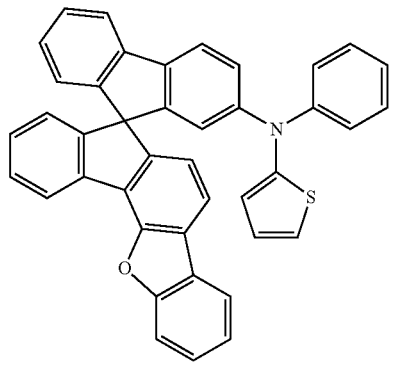
[Chemical Formula A-18]
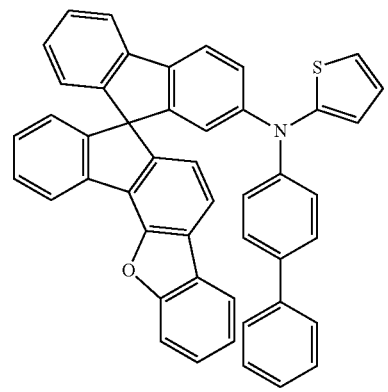

[Chemical Formula A-19]
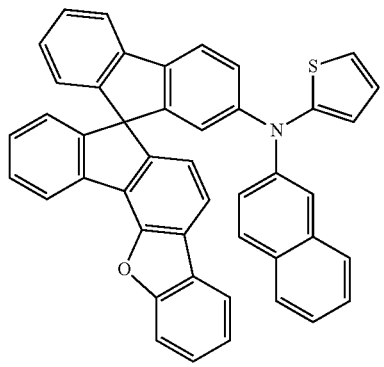
[Chemical Formula A-20]
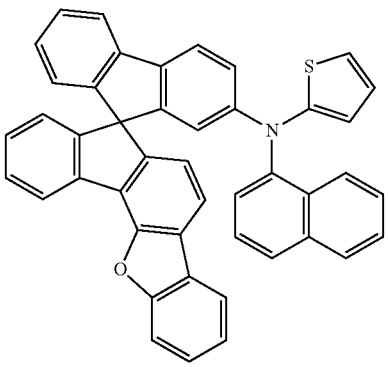
[Chemical Formula A-21]
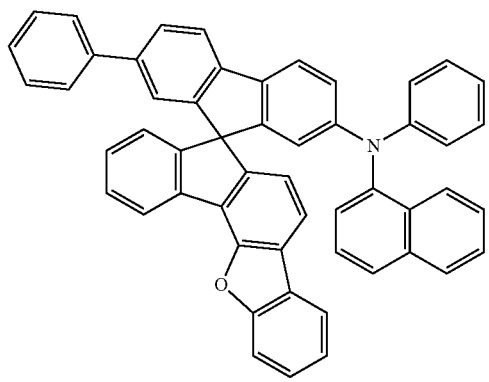
[Chemical Formula A-22]
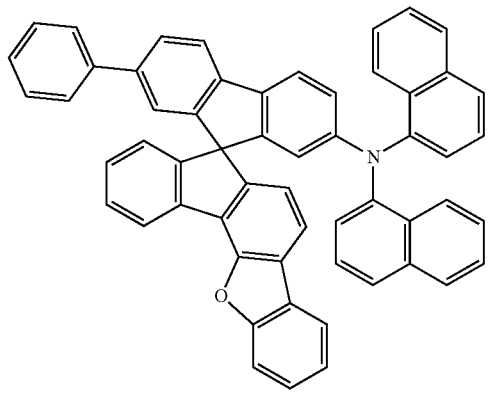
[Chemical Formula A-23]
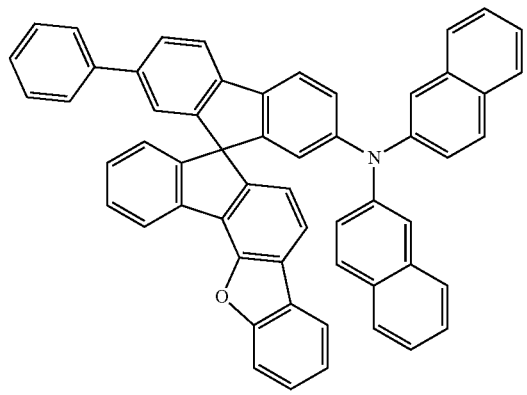
[Chemical Formula A-24]
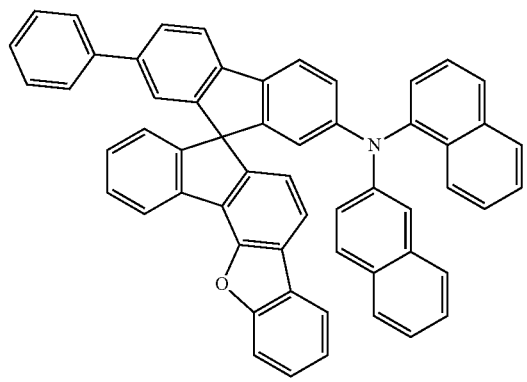
[Chemical Formula A-25]
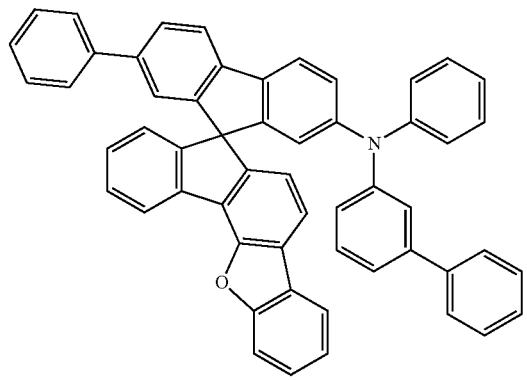
[Chemical Formula A-26]
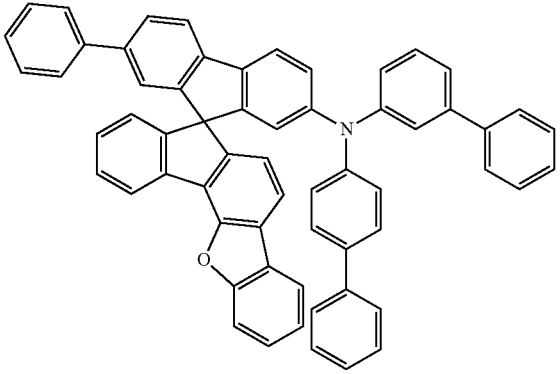

[Chemical Formula A-27]
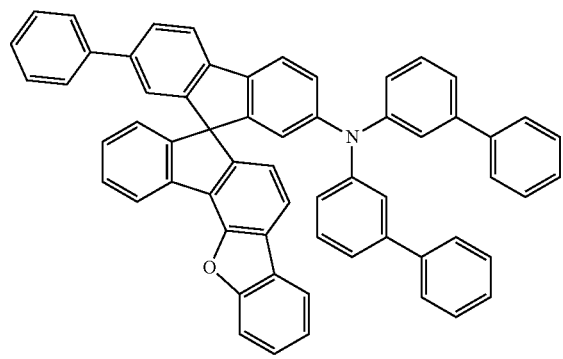
[Chemical Formula A-28]
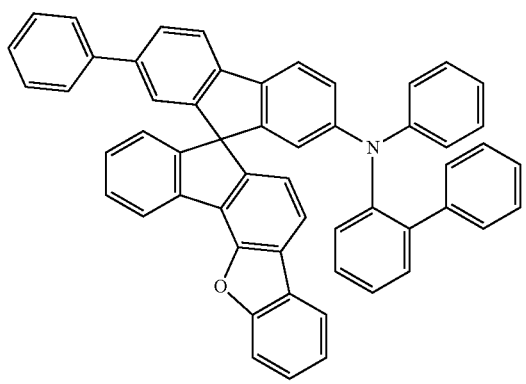
[Chemical Formula A-29]
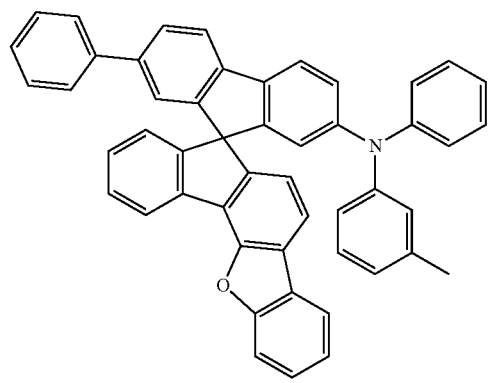
[Chemical Formula A-30]
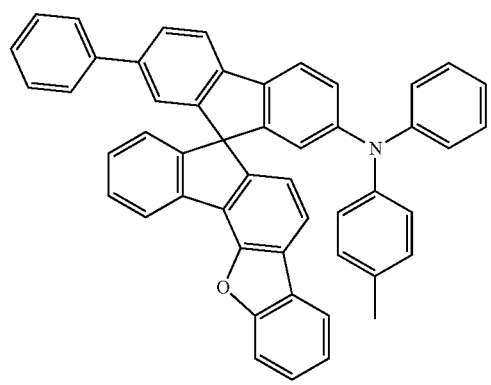
[Chemical Formula A-31]
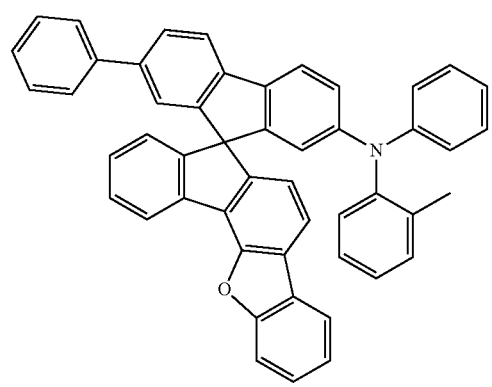
[Chemical Formula A-32]
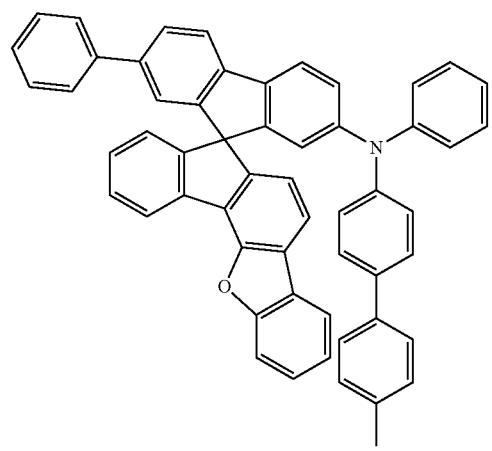
[Chemical Formula A-33]
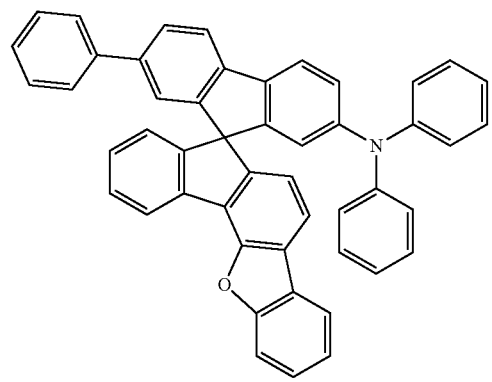

[Chemical Formula A-34]
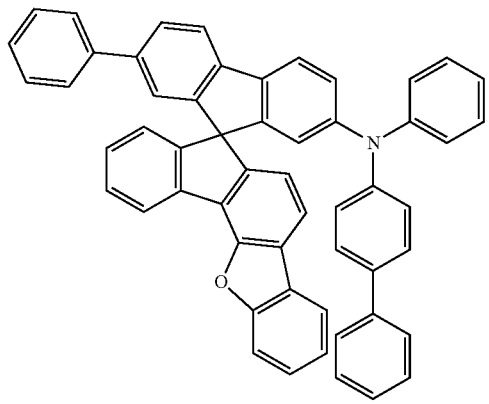
[Chemical Formula A-35]
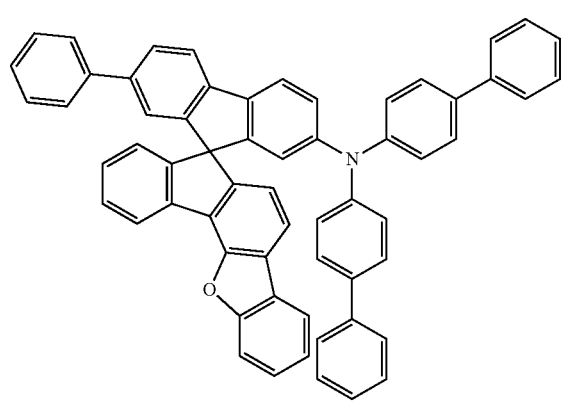
[Chemical Formula A-36]
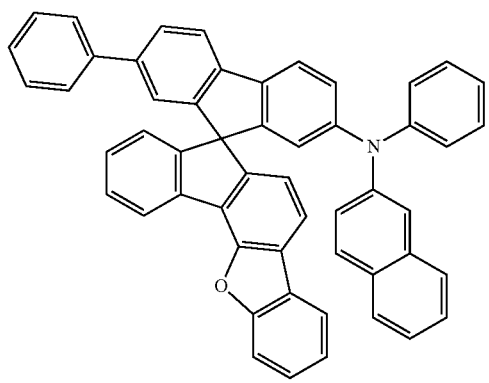
[Chemical Formula A-37]
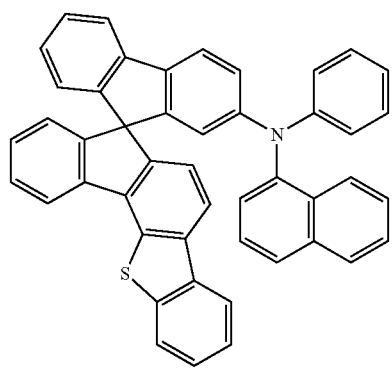
[Chemical Formula A-38]
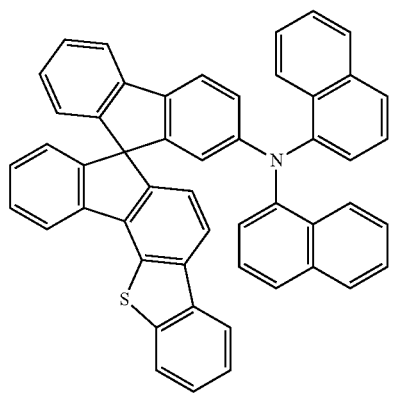
[Chemical Formula A-39]
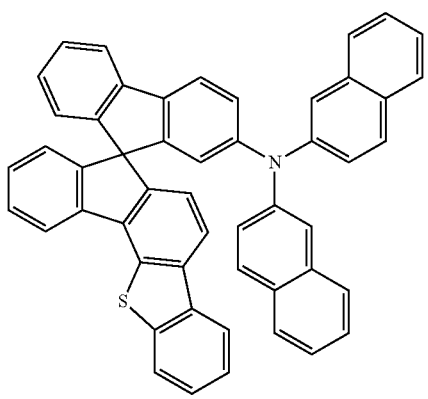
[Chemical Formula A-40]
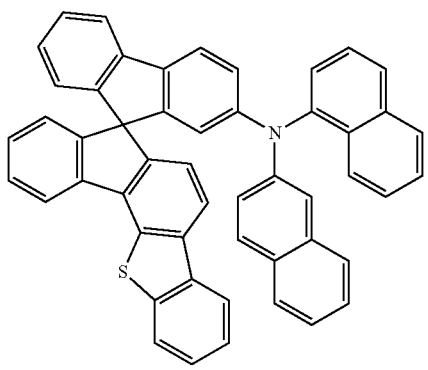
[Chemical Formula A-41]
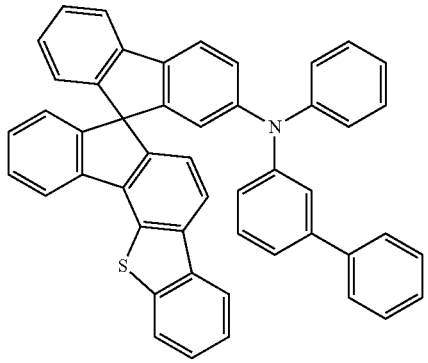

[Chemical Formula A-42]
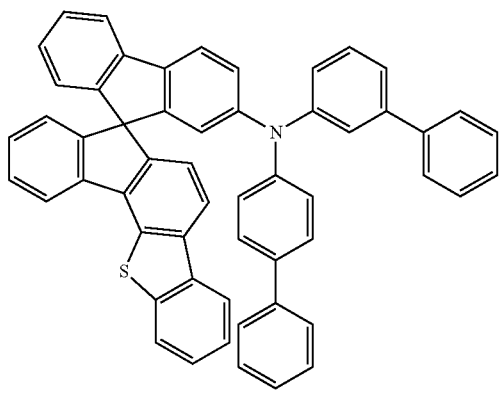
[Chemical Formula A-43]
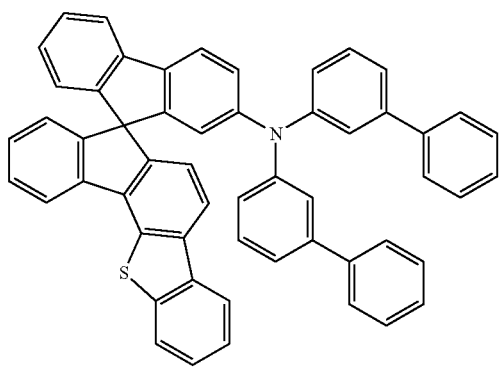
[Chemical Formula A-44]
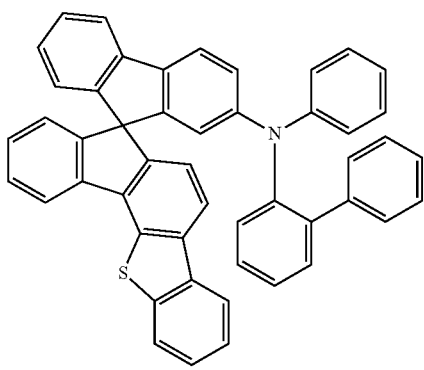
[Chemical Formula A-45]
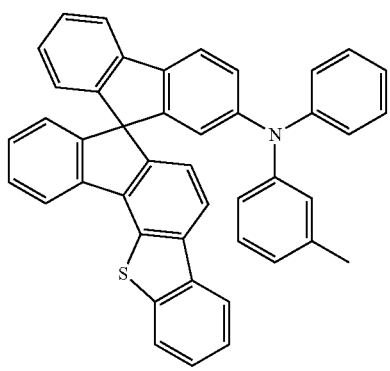
[Chemical Formula A-46]
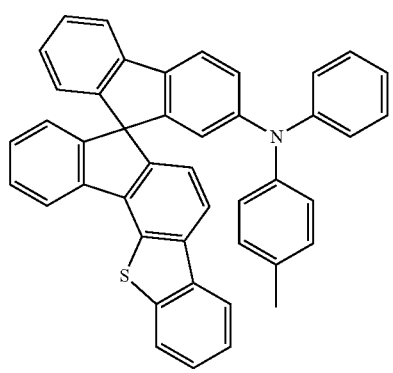
[Chemical Formula A-47]
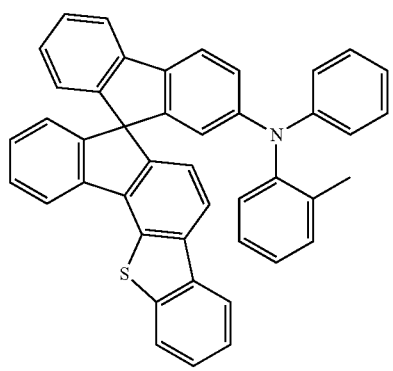
[Chemical Formula A-48]
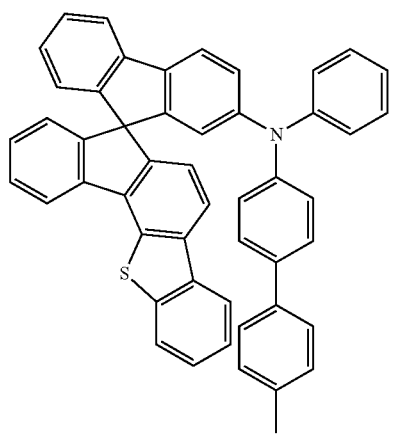
[Chemical Formula A-49]
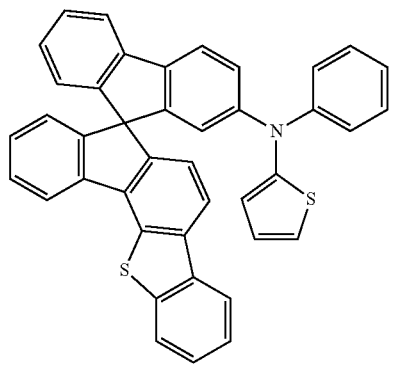

[Chemical Formula A-50]
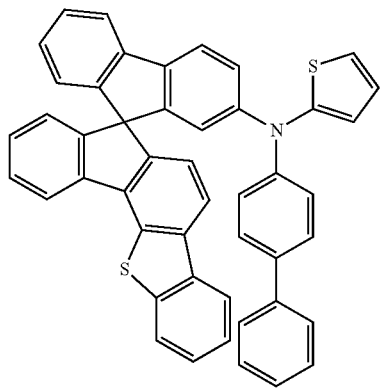
[Chemical Formula A-51]
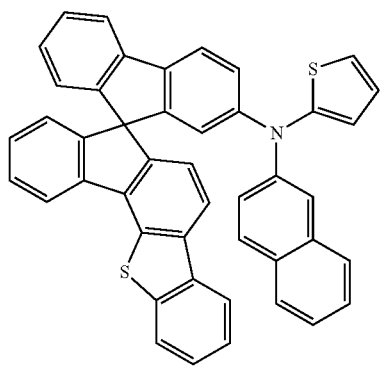
[Chemical Formula A-52]
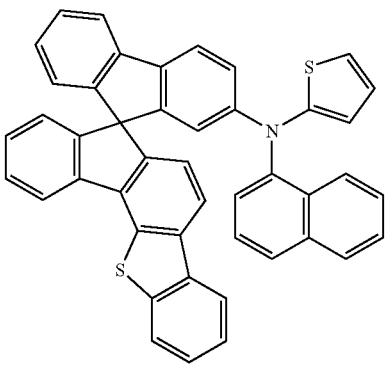
[Chemical Formula A-53]
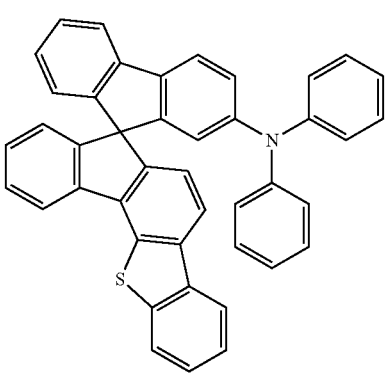
[Chemical Formula A-54]
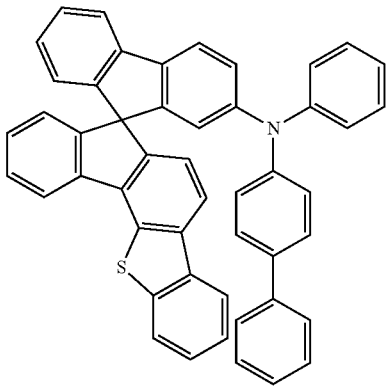
[Chemical Formula A-55]
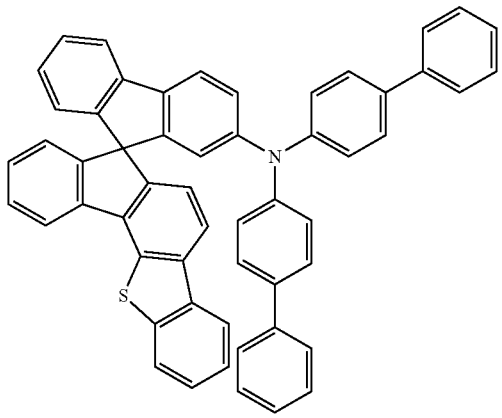
[Chemical Formula A-56]
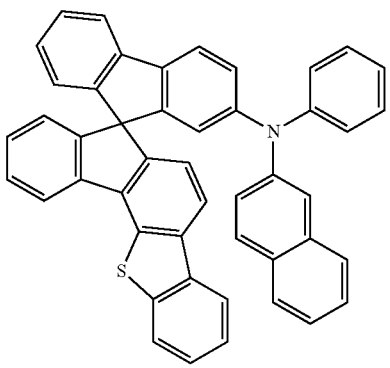
[Chemical Formula A-57]
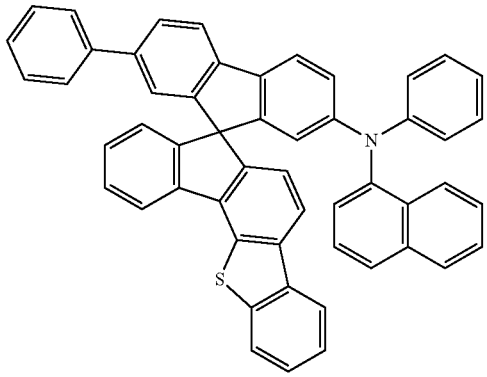

[Chemical Formula A-58]
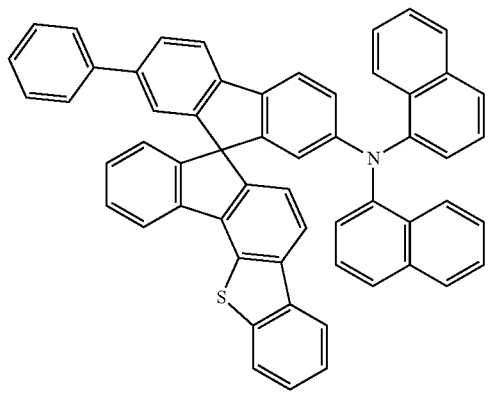
[Chemical Formula A-59]
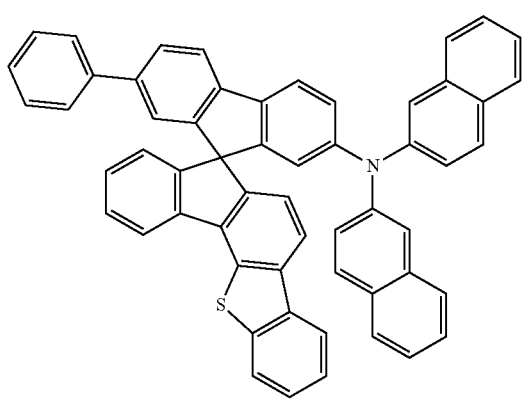
[Chemical Formula A-60]
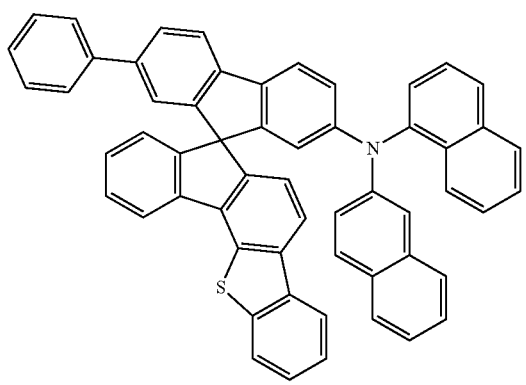
[Chemical Formula A-61]
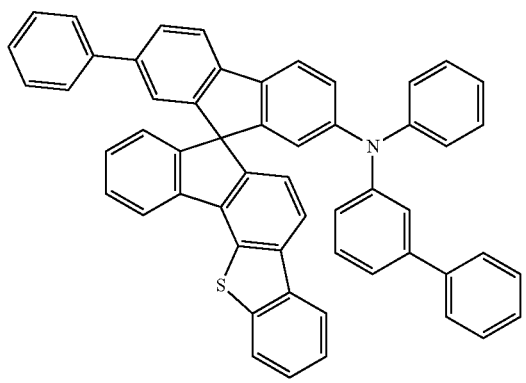
[Chemical Formula A-62]
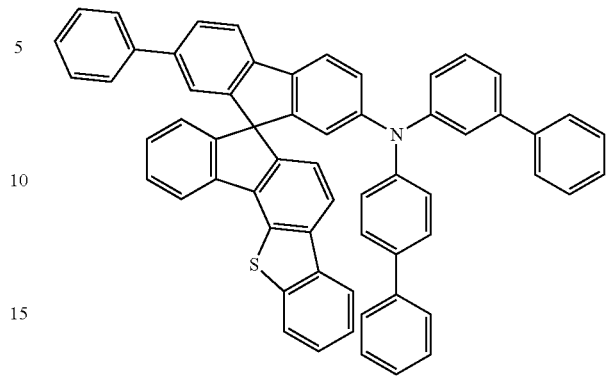
[Chemical Formula A-63]
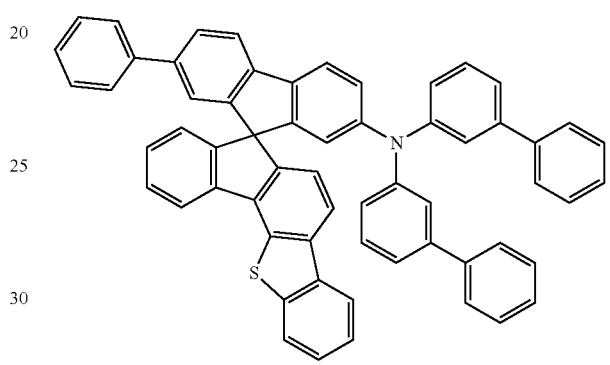
[Chemical Formula A-64]
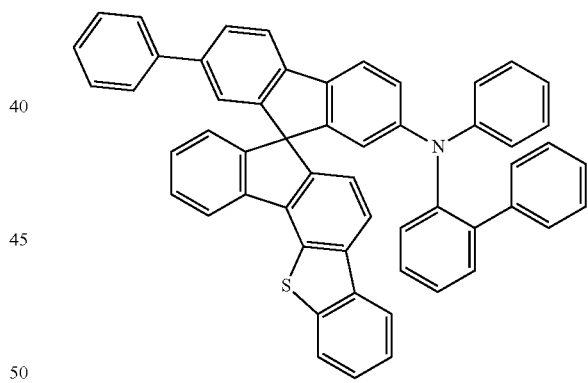
[Chemical Formula A-65]
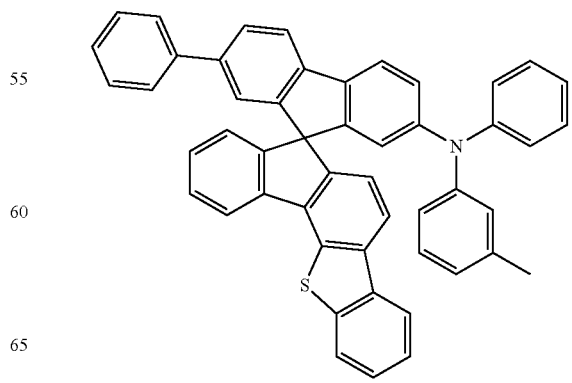

[Chemical Formula A-66]
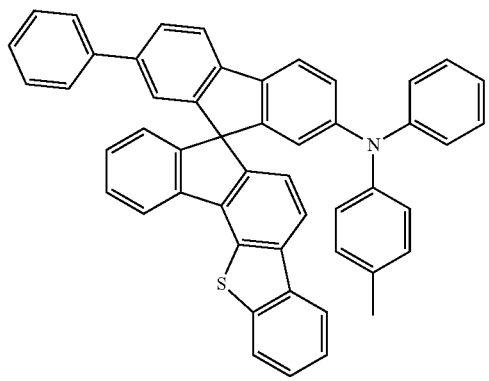
[Chemical Formula A-67]
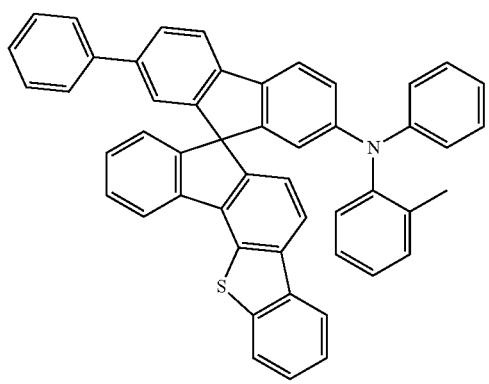
[Chemical Formula A-68]
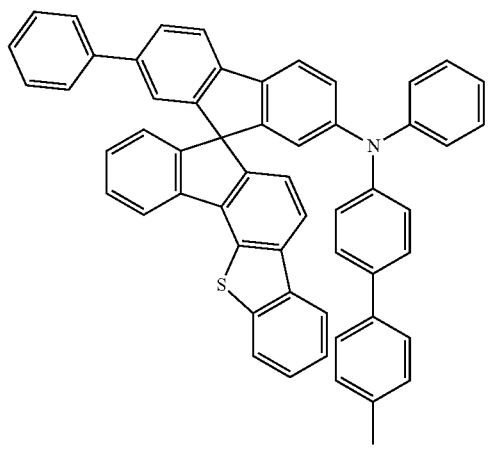
[Chemical Formula A-69]
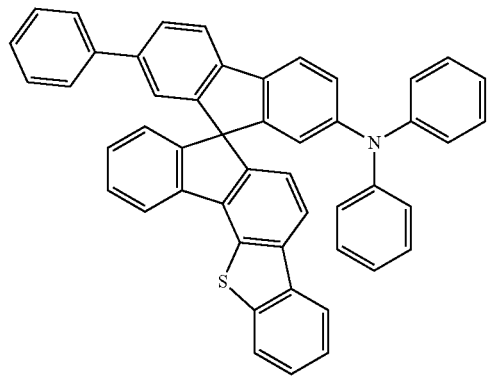
[Chemical Formula A-70]
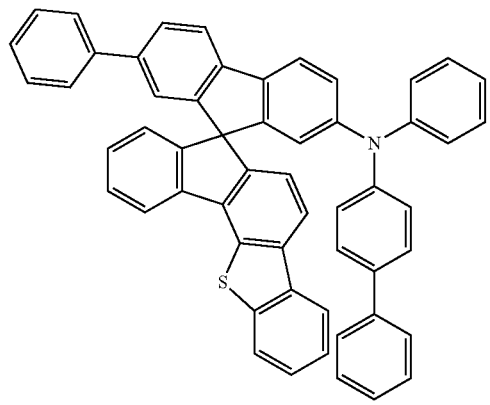
[Chemical Formula A-71]
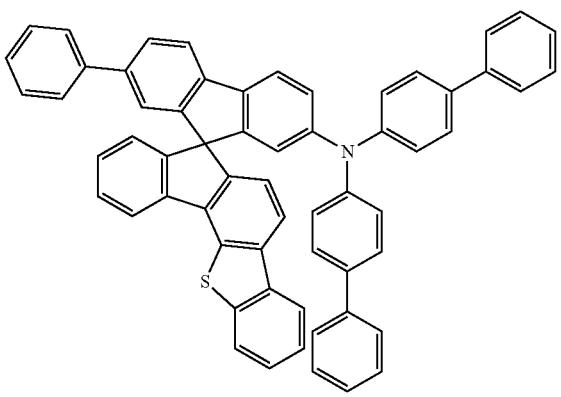
[Chemical Formula A-72]
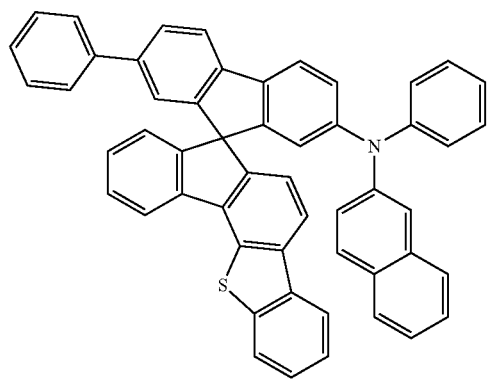

More specifically, the compound for an organic optoelectronic device may be represented by one of the following Chemical Formulae B-1 to B-40, but is not limited thereto.
[Chemical Formula B-1]
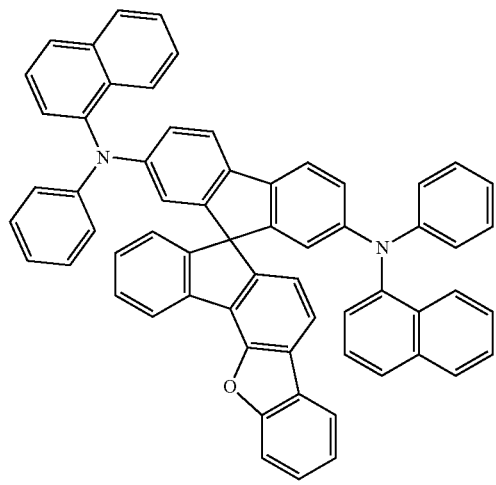
[Chemical Formula B-2]
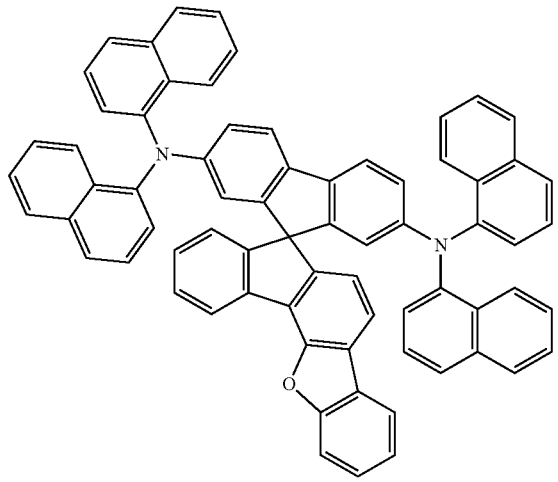
[Chemical Formula B-3]
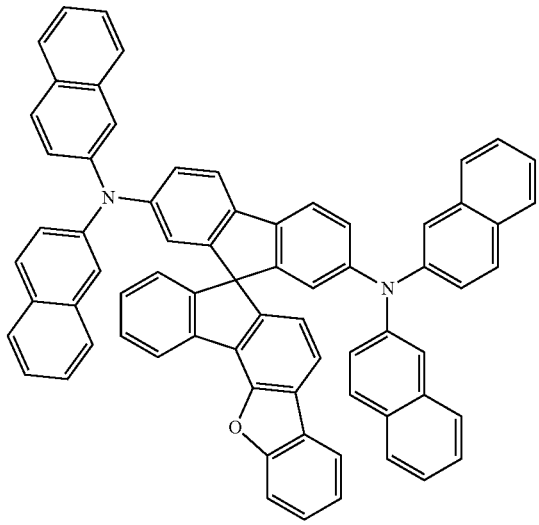
[Chemical Formula B-4]
[Chemical Formula B-5]
[Chemical Formula B-6]
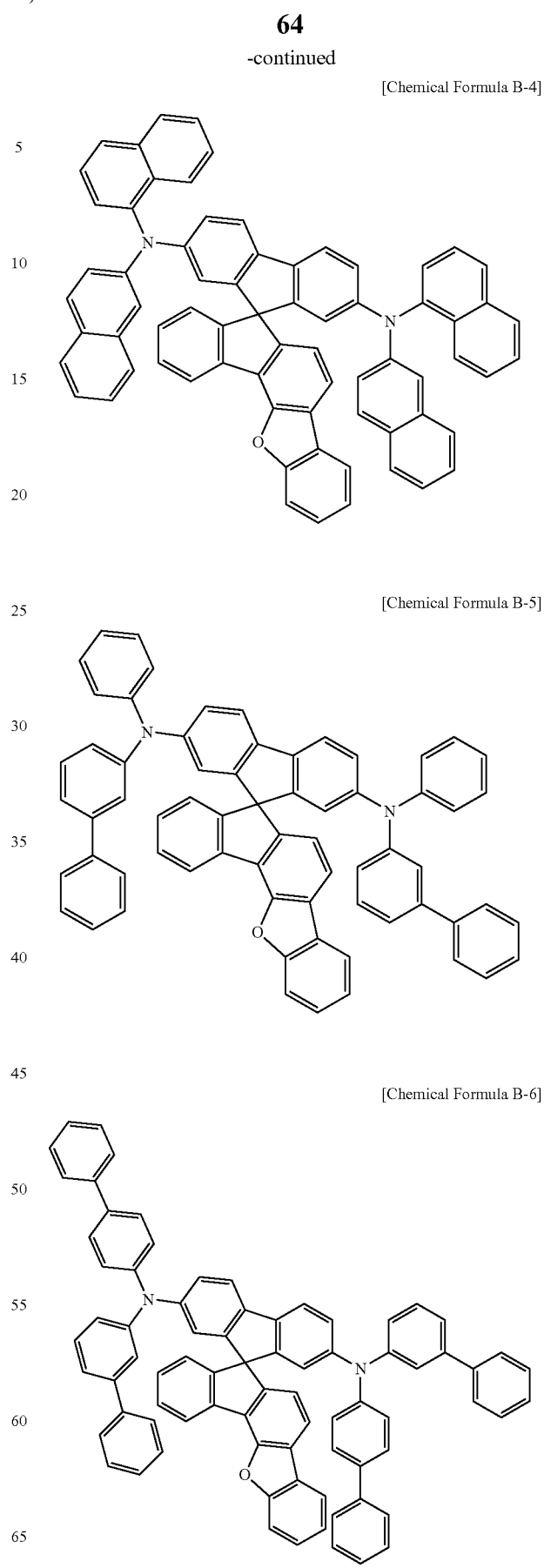

-continued
[Chemical Formula B-7]
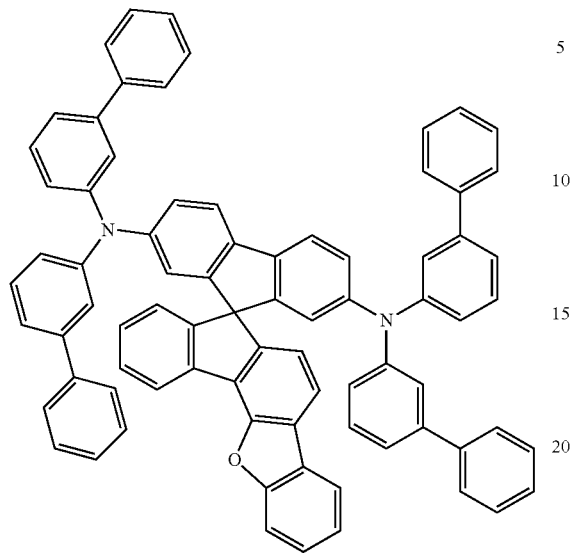
[Chemical Formula B-8]
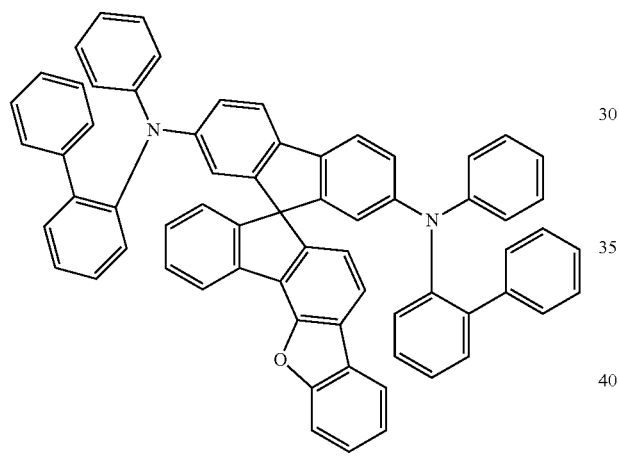
[Chemical Formula B-9]
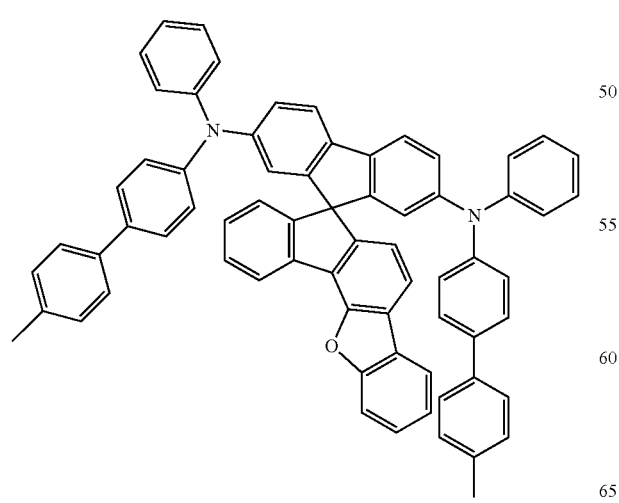
-continued
[Chemical Formula B-10]
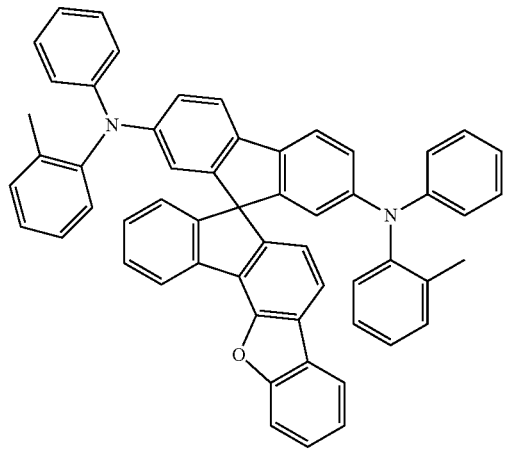
[Chemical Formula B-11]
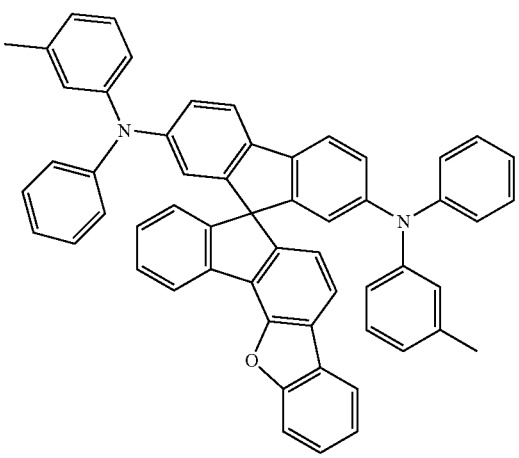
[Chemical Formula B-12]
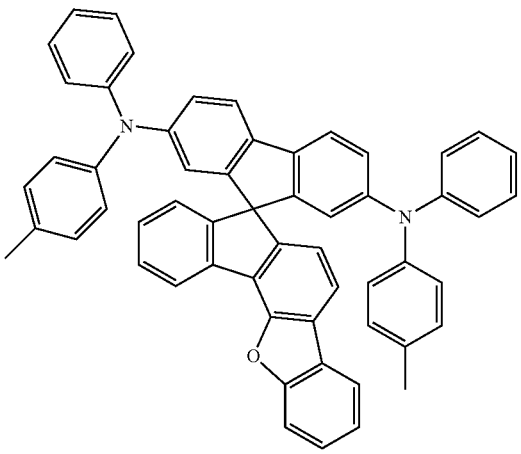

[Chemical Formula B-13]
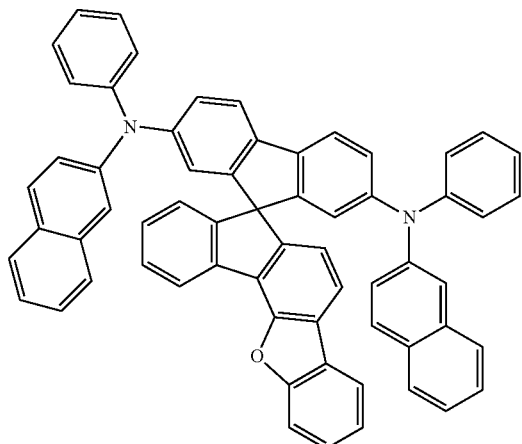
[Chemical Formula B-14]
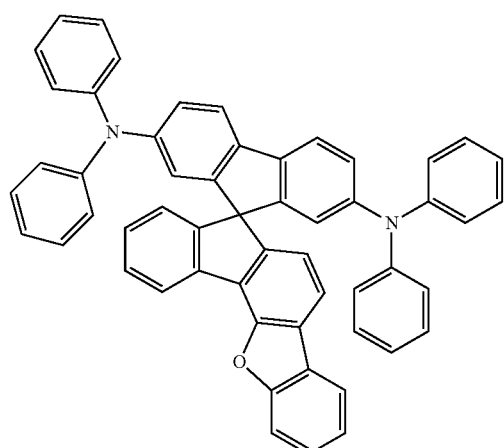
[Chemical Formula B-15]
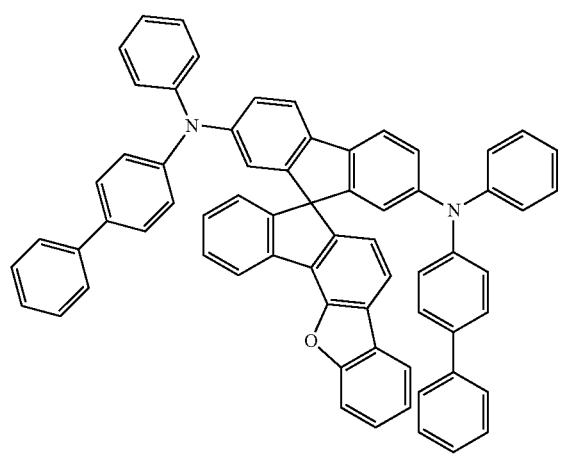
[Chemical Formula B-16]
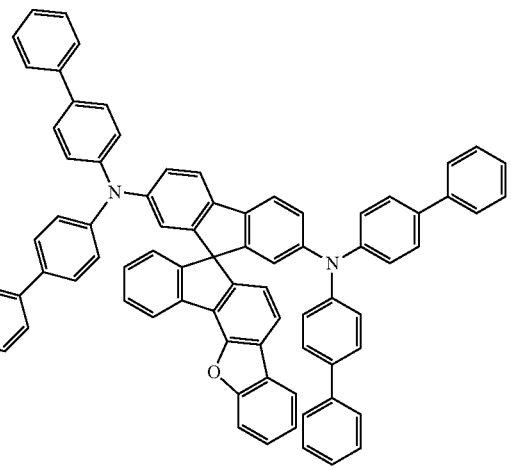
[Chemical Formula B-17]
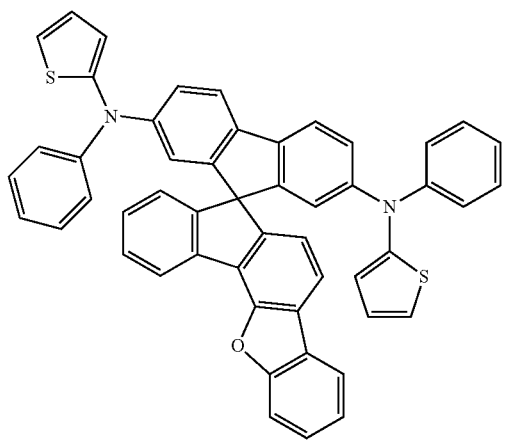
[Chemical Formula B-18]
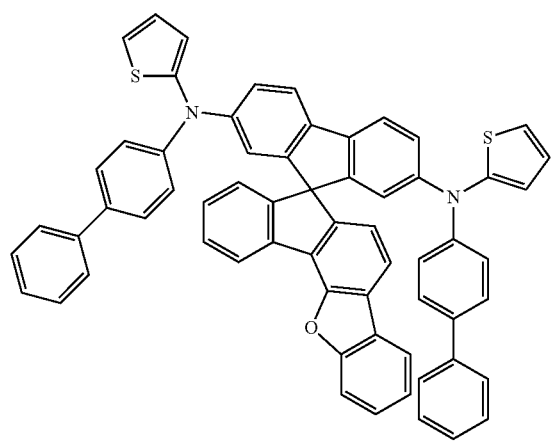

[Chemical Formula B-19]
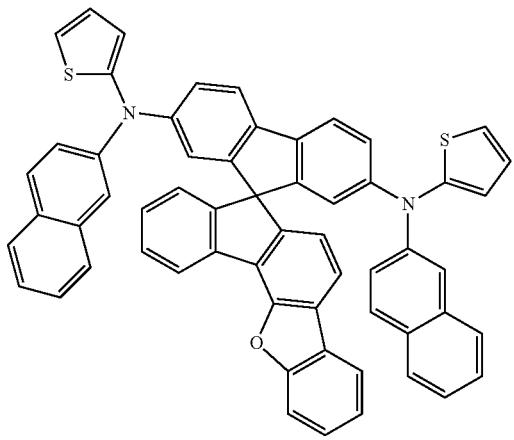
[Chemical Formula B-20]
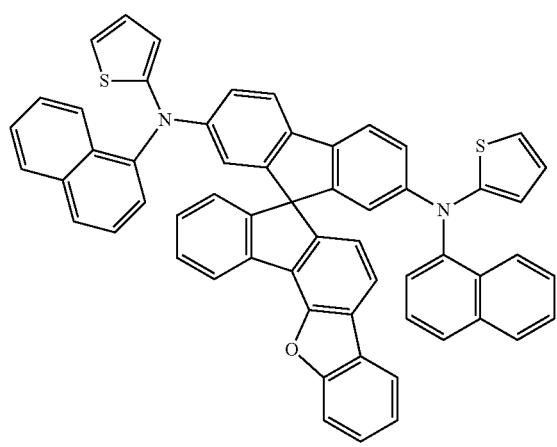
[Chemical Formula B-21]
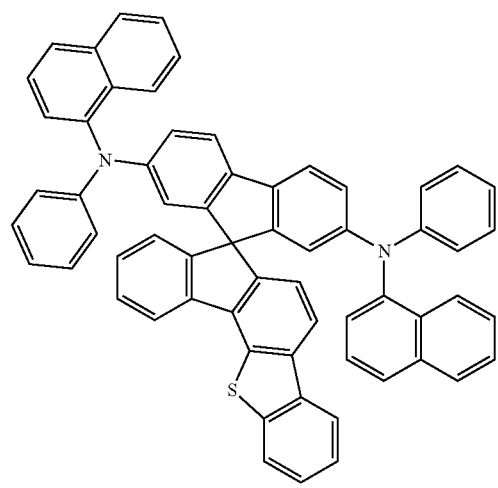
[Chemical Formula B-22]
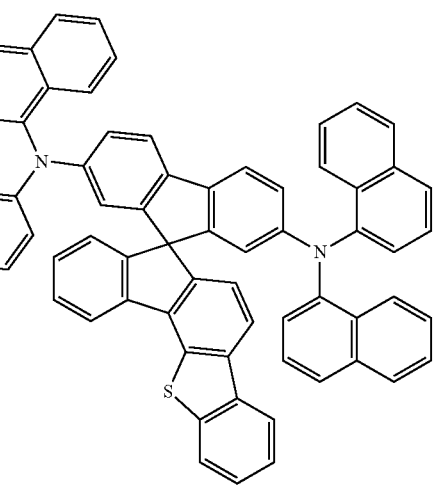
[Chemical Formula B-23]
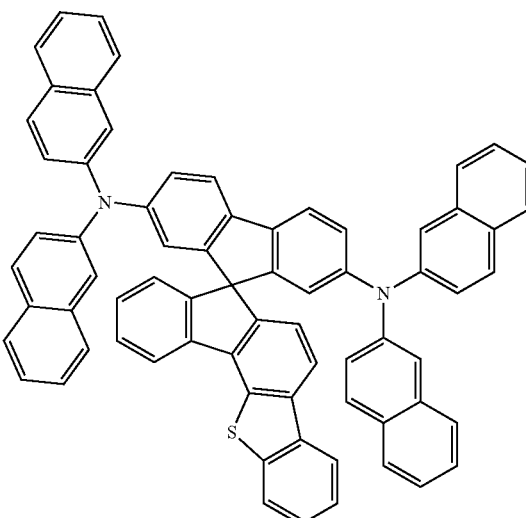
[Chemical Formula B-24]
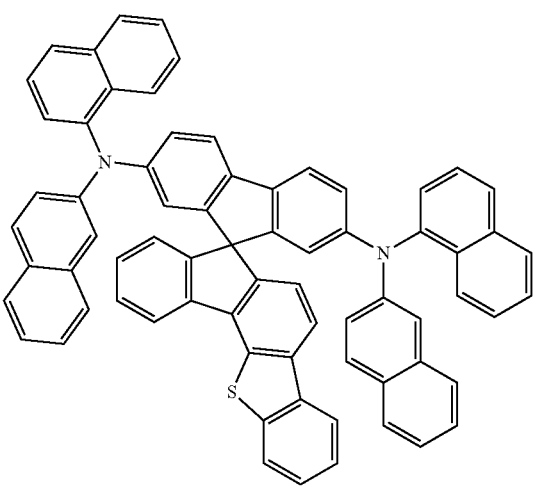

[Chemical Formula B-25]
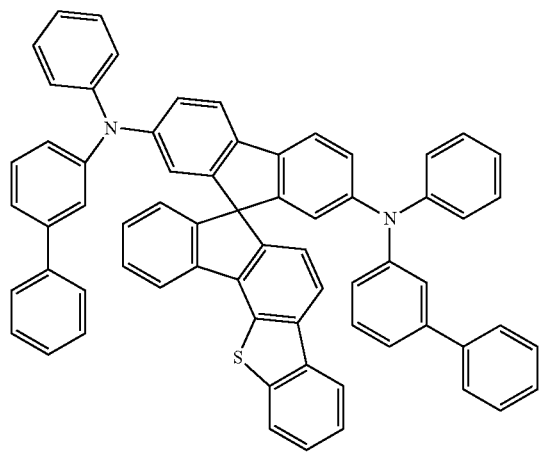
[Chemical Formula B-26]
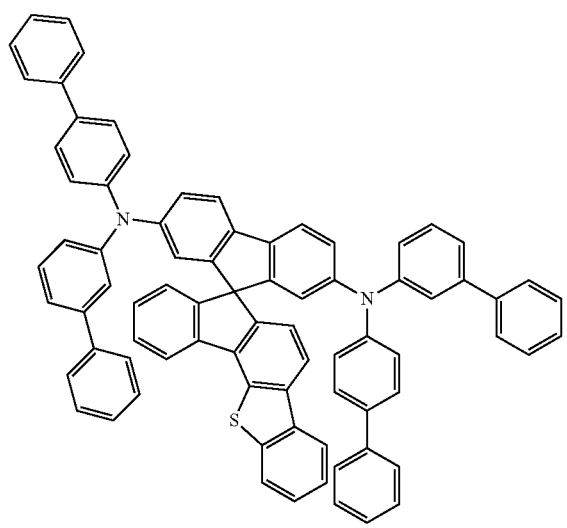
[Chemical Formula B-27]
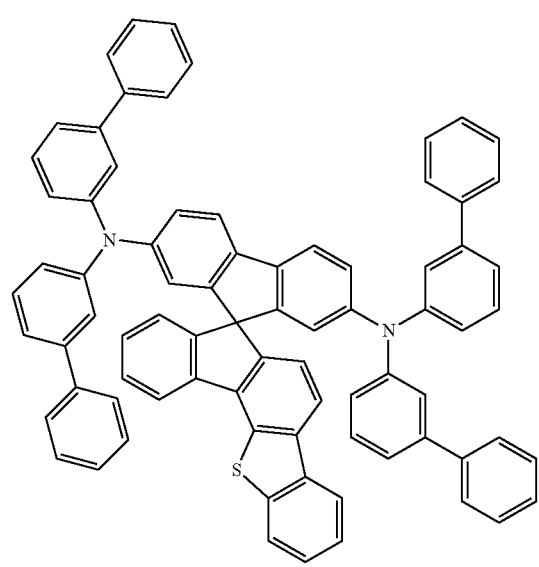
[Chemical Formula B-28]
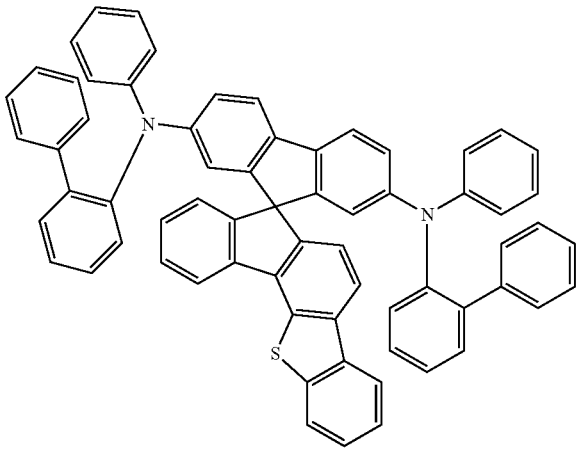
[Chemical Formula B-29]
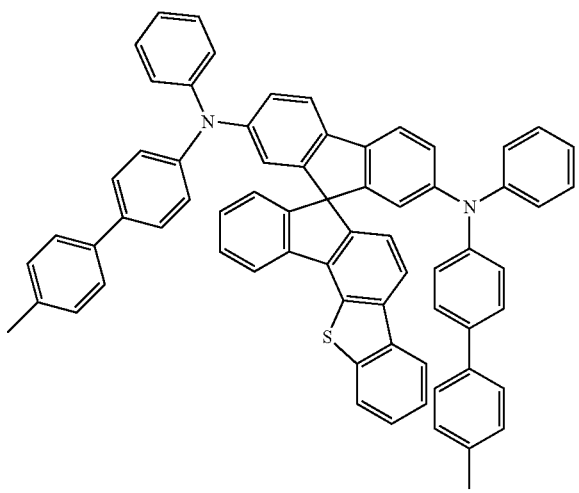
[Chemical Formula B-30]
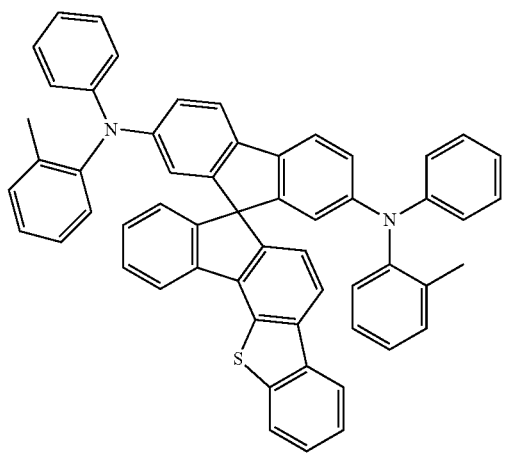

[Chemical Formula B-31]
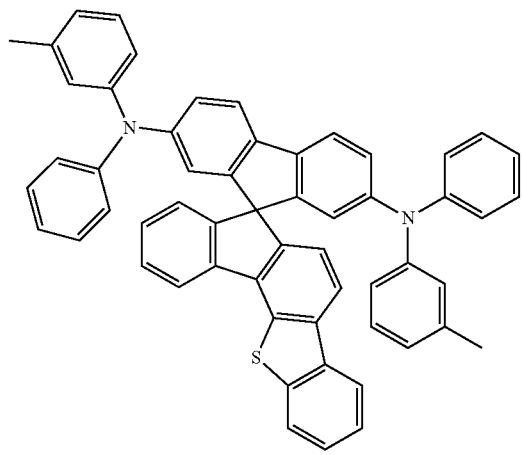
[Chemical Formula B-32]
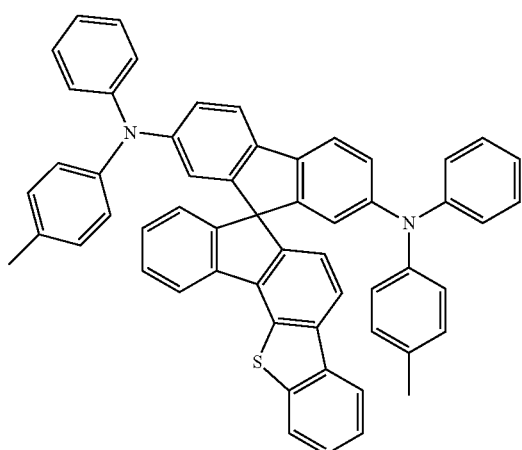
[Chemical Formula B-33]
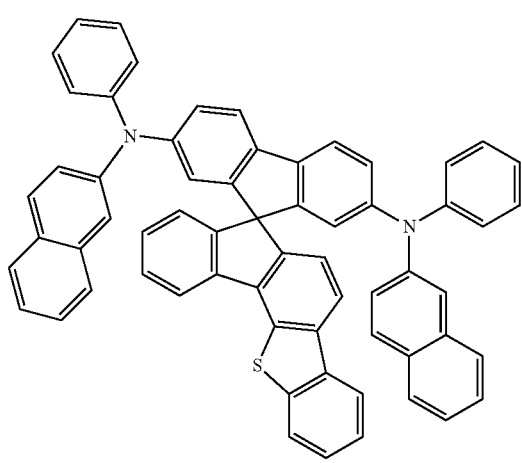
[Chemical Formula B-34]
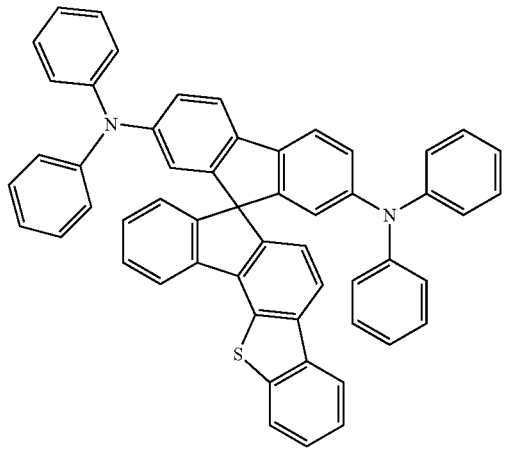
[Chemical Formula B-35]
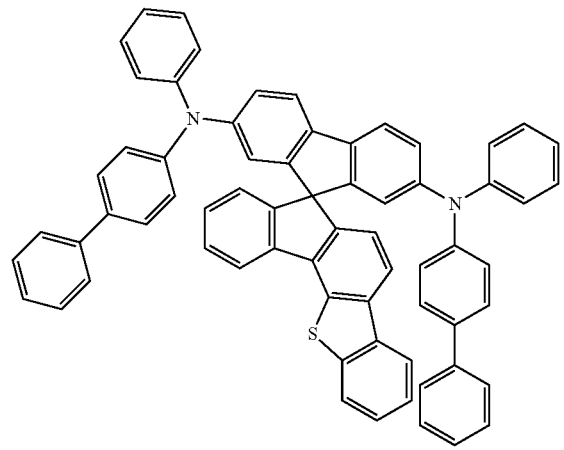
[Chemical Formula B-36]
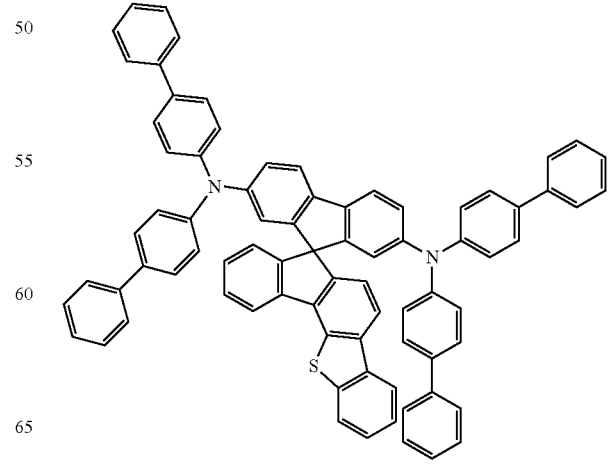

[Chemical Formula B-37]

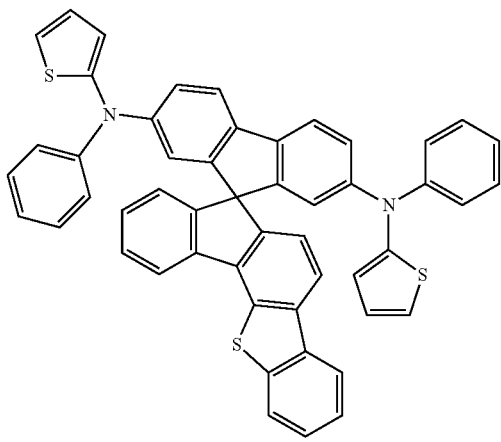

[Chemical Formula B-38]

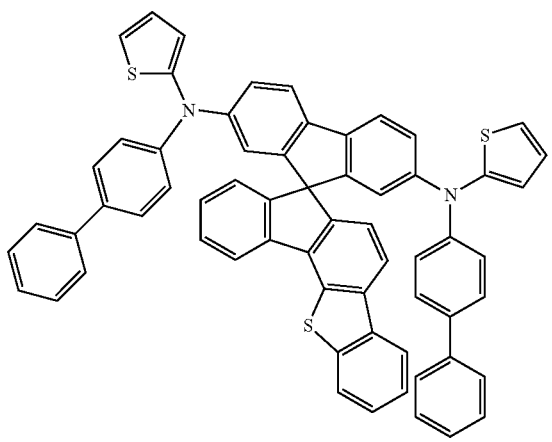

[Chemical Formula B-39]

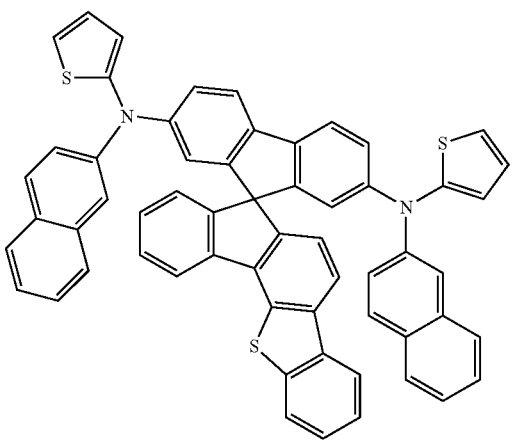

[Chemical Formula B-40]

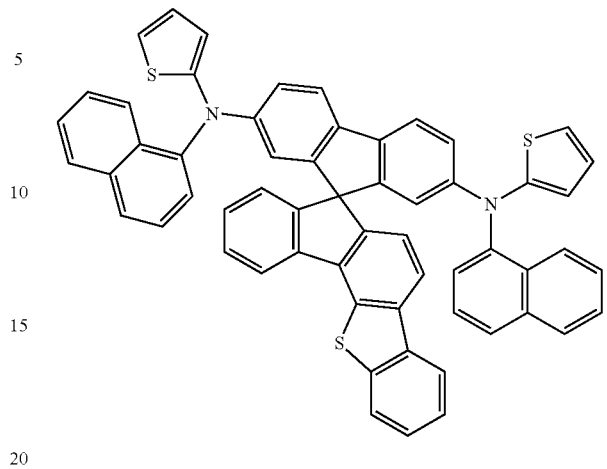

When the above compound according to one embodiment of the present invention requires both electron and hole characteristics, the functional group having electron characteristics may be introduced to effectively improve life-span of an organic light emitting diode and decreasing its driving voltage.

The above compound for an organic optoelectronic device according to one embodiment of the present invention shows a maximum light emitting wavelength in a range of about 320 to about 500 nm, high triplet exciton energy (T1) of greater than equal to about 2.0 eV and specifically, about 2.0 to about 4.0 eV and thus, has an advantage of increasing luminous efficiency of a dopant by well transporting charges of a host having high triplet exciton energy to the dopant and decreasing a driving voltage by freely adjusting HOMO and LUMO energy levels and accordingly, may be used as a host material or a charge transport material.

In addition, the compound for an organic optoelectronic device has optical and electrical activity and thus, may be used as a non-linear optical material, an electrode material, an electrochromic material, an optical switch, a sensor, a module, a wave guide, an organic transistor, a laser, an optical absorbing material, a dielectric material, and a material for a separation membrane and the like.

The compound for an organic optoelectronic device including the above compounds has a glass transition temperature of greater than or equal to about 90° C. and a thermal decomposition temperature of greater than or equal to about 400° C., indicating improved thermal stability. Thereby, it is possible to produce an organic optoelectronic device having a high efficiency.

The compound for an organic optoelectronic device including the above compounds may play a role for emitting light or injecting and/or transporting electrons, and also act as a light emitting host with an appropriate dopant. In other words, the compound for an organic optoelectronic device may be used as a phosphorescent or fluorescent host material, a blue light emitting dopant material, or an electron transport material.

The compound for an organic optoelectronic device according to one embodiment of the present invention is used for an organic thin layer, and it may improve the life-span characteristics, efficiency characteristics, electrochemical stability, and thermal stability of an organic optoelectronic device and decrease the driving voltage.

Therefore, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photo-conductor drum, an organic memory device, and the like. For example, the compound for an organic optoelectronic device according to one embodiment may be included in an electrode or an electrode buffer layer in the organic solar cell to improve the quantum efficiency, and it may be used as an electrode material for a gate, a source-drain electrode, or the like in the organic transistor.

Hereinafter, an organic light emitting diode is specifically described.

An organic light emitting diode according to another embodiment of the present invention includes an anode, a cathode, and at least one or more organic thin layer between the anode and the cathode, and at least one of the organic thin layers may include the compound for an organic optoelectronic device according to one embodiment of the present invention.

The organic thin layer including the compound for an organic optoelectronic device may include a layer selected from an emission layer, a hole transport layer, a hole injection layer, an electron transport layer, an electron injection layer, a hole blocking layer, and a combination thereof. The at least one layer includes the compound for an organic optoelectronic device according to one embodiment. Particularly, the compound for an organic optoelectronic device according to one embodiment may be included in an electron transport layer or electron injection layer. In addition, when the compound for an organic optoelectronic device is included in the emission layer, the compound for an organic optoelectronic device may be included as a phosphorescent or fluorescent host, and particularly, as a fluorescent blue dopant material.

FIGS. 1 to 5 are cross-sectional views showing organic light emitting diodes including the compound for an organic optoelectronic device according to one embodiment of the present invention.

Referring to FIGS. 1 to 5, organic light emitting diodes 100, 200, 300, 400, and 500 according to one embodiment include at least one organic thin layer 105 interposed between an anode 120 and a cathode 110.

The anode 120 includes an anode material having a large work function to help hole injection into an organic thin layer. Specific examples of the anode material include: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or SnO$_2$:Sb; or a conductive polymer such as poly(3-methylthiophene), poly[3,4-(ethylene-1,2-dioxy)thiophene] (PEDT), polypyrrole, and polyaniline, but is not limited thereto. It is preferable to include a transparent electrode including indium tin oxide (ITO) as an anode.

The cathode 110 includes a cathode material having a small work function to help electron injection into an organic thin layer. Specific examples of the cathode material include: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, LiO$_2$/Al, LiF/Ca, LiF/Al, and BaF$_2$/Ca, but is not limited thereto. It is preferable to include a metal electrode including aluminum as a cathode.

First, referring to FIG. 1, the organic light emitting diode 100 includes an organic thin layer 105 including only an emission layer 130.

Figure 2:
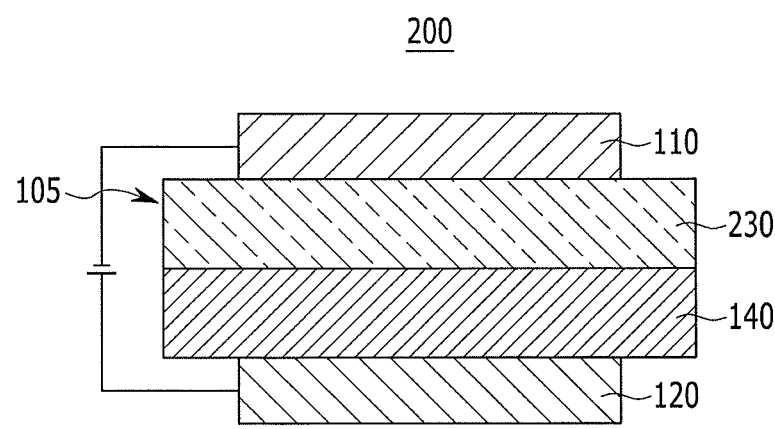

Referring to FIG. 2, a double-layered organic light emitting diode 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and hole transport layer (HTL) 140. The emission layer 130 also functions as an electron transport layer (ETL), and the hole transport layer (HTL) 140 layer has an excellent binding property with a transparent electrode such as ITO or an excellent hole transport capability.

Figure 3:
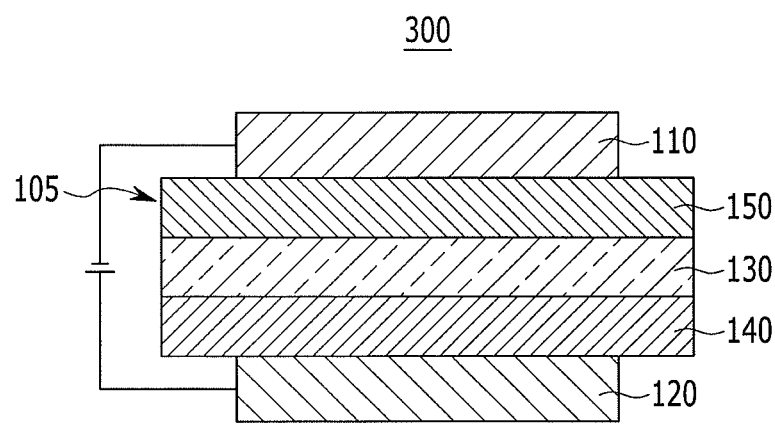

Referring to FIG. 3, a three-layered organic light emitting diode 300 includes an organic thin layer 105 including an electron transport layer (ETL) 150, an emission layer 130, and a hole transport layer (HTL) 140. The emission layer 130 is independently installed, and layers having an excellent electron transport capability or an excellent hole transport capability are separately stacked.

Figure 4:
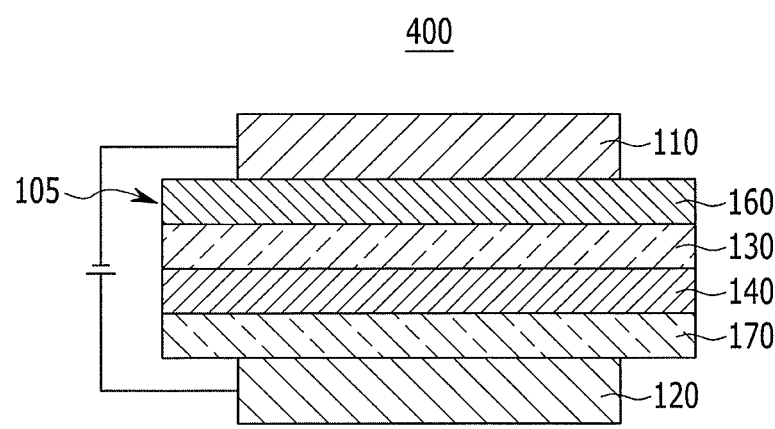

As shown in FIG. 4, a four-layered organic light emitting diode 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
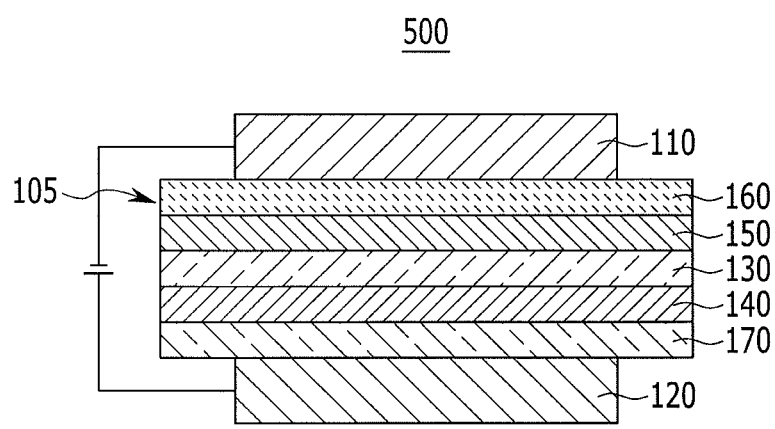

As shown in FIG. 5, a five-layered organic light emitting diode 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from the group consisting of an electron transport layer (ETL) 150, an electron injection layer (EIL) 160, emission layers 130 and 230, a hole transport layer (HTL) 140, a hole injection layer (HIL) 170, and combinations thereof includes the compound for an organic optoelectronic device. The compound for an organic optoelectronic device may be used for an electron transport layer (ETL) 150 including the electron transport layer (ETL) 150 or electron injection layer (EIL) 160. When it is used for the electron transport layer (ETL), it is possible to provide an organic light emitting diode having a more simple structure because it does not require an additional hole blocking layer (not shown).

Furthermore, when the compound for an organic optoelectronic device is included in the emission layers 130 and 230, the compound for an organic optoelectronic device may be included as a phosphorescent or fluorescent host or a fluorescent blue dopant.

The organic light emitting diode may be manufactured by: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

Another embodiment of the present invention provides a display device including the light emitting diode according to the above embodiment.

Hereinafter, the embodiments are illustrated in more detail with reference to examples. These examples, however, should not in any sense be interpreted as limiting the scope of the present invention.

Preparation of Compound for Organic Optoelectronic Device

Example 1: Preparation of Compound A-14

A compound represented by the above Chemical Formula A-14 as specific examples of a compound for an organic optoelectronic device according to one embodiment of the present invention was synthesized through the following Reaction Scheme 1.

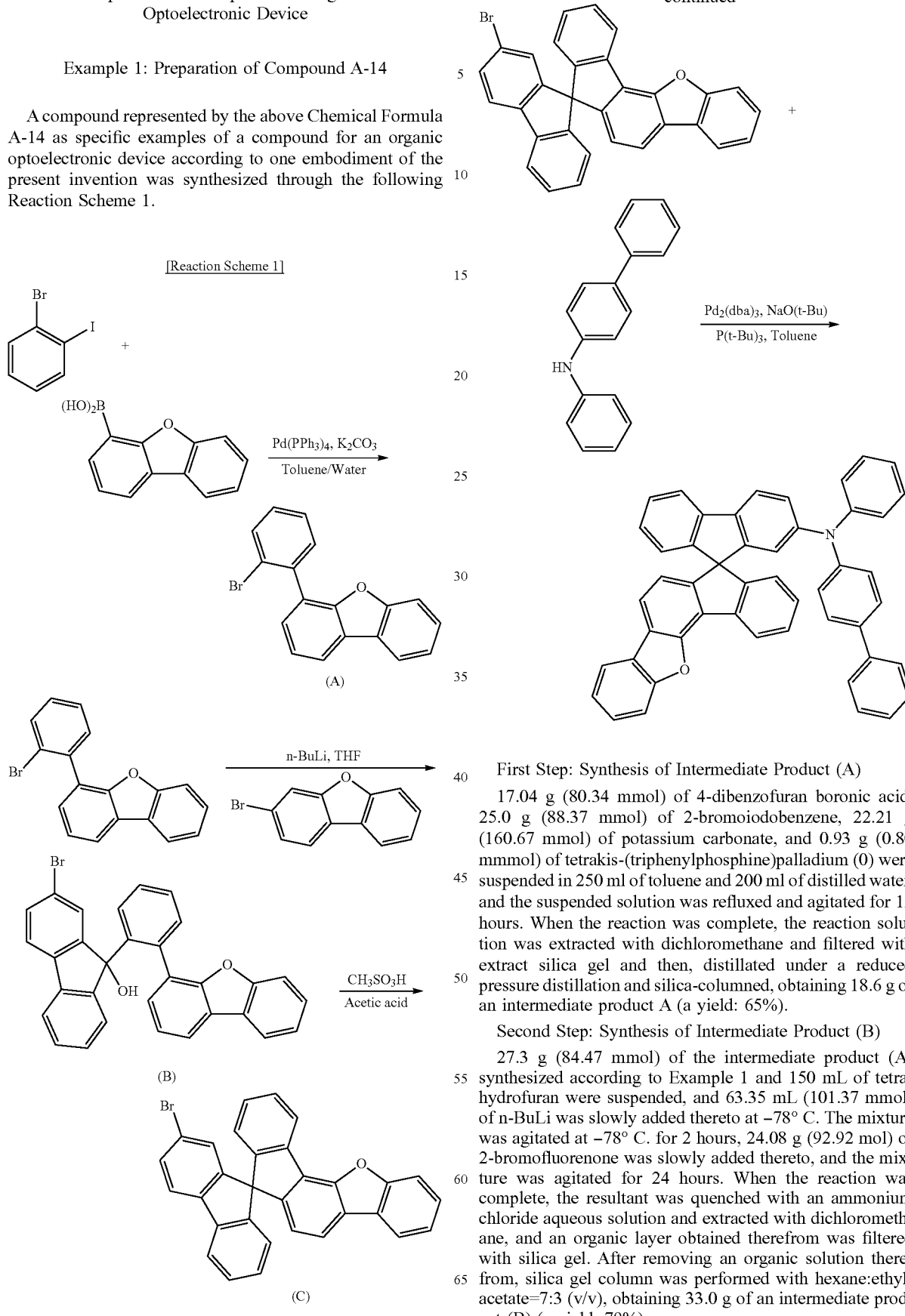

First Step: Synthesis of Intermediate Product (A)

17.04 g (80.34 mmol) of 4-dibenzofuran boronic acid, 25.0 g (88.37 mmol) of 2-bromoiodobenzene, 22.21 g (160.67 mmol) of potassium carbonate, and 0.93 g (0.80 mmmol) of tetrakis-(triphenylphosphine)palladium (0) were suspended in 250 ml of toluene and 200 ml of distilled water, and the suspended solution was refluxed and agitated for 12 hours. When the reaction was complete, the reaction solution was extracted with dichloromethane and filtered with extract silica gel and then, distillated under a reduced pressure distillation and silica-columned, obtaining 18.6 g of an intermediate product A (a yield: 65%).

Second Step: Synthesis of Intermediate Product (B)

27.3 g (84.47 mmol) of the intermediate product (A) synthesized according to Example 1 and 150 mL of tetrahydrofuran were suspended, and 63.35 mL (101.37 mmol) of n-BuLi was slowly added thereto at −78° C. The mixture was agitated at −78° C. for 2 hours, 24.08 g (92.92 mol) of 2-bromofluorenone was slowly added thereto, and the mixture was agitated for 24 hours. When the reaction was complete, the resultant was quenched with an ammonium chloride aqueous solution and extracted with dichloromethane, and an organic layer obtained therefrom was filtered with silica gel. After removing an organic solution therefrom, silica gel column was performed with hexane:ethylacetate=7:3 (v/v), obtaining 33.0 g of an intermediate product (B) (a yield: 79%).

Third Step: Synthesis of Intermediate Product (C)

33.0 g (65.6 mmol) of the intermediate product (B) was suspended in 350 mL of acetic acid, and 12.8 mL (196.8 mmol) of $CH_3SO_3H$ was slowly added thereto at room temperature. The mixture was agitated for 24 hours. When the reaction was complete, the resultant was quenched with 200 mL of a sodium bicarbonate aqueous solution, a solid produced therein was filtered, extraction was performed with dichloromethane and distilled water, and an organic layer was filtered with silica gel. After removing an organic solution therefrom, silica gel column was performed with hexane:dichloromethane=6:4 (v/v), obtaining 29.3 g of an intermediate product (D) (a yield: 92%).

Fourth Step: Synthesis of Compound A-14

15.0 g (30.9 mmol) of the intermediate compound (C), 8.34 g (34.0 mmol) of biphenylphenylamine, 4.45 g (46.36 mmol) of NaO(t-Bu), and 0.28 g (0.31 mmmol) of $Pd_2(dba)_3$ were suspended in 300 ml of toluene, 0.45 mL (1.85 mmol) of $P(t-Bu)_3$ was added thereto, and the mixture was refluxed and agitated for 12 hours. The agitated mixture was extracted with dichloromethane and distilled water, and an organic layer obtained therefrom was filtered with silica gel. After removing an organic solution therefrom, silica gel column was performed with hexane:dichloromethane=7:3 (v/v) to obtain a solid product, the solid product was recrystallized with dichloromethane and n-hexane, obtaining 17.4 g of a compound represented by Chemical Formula 1 (a yield: 87%.

Example 2: Synthesis of Compound A-15

15.0 g (30.9 mmol) of the intermediate compound (C), 10.93 g (34.0 mmol) of bisbiphenylamine, 4.45 g (46.36 mmol) of NaO(t-Bu), and 0.28 g (0.31 mmmol) of $Pd_2(dba)_3$ were suspended in 300 ml of toluene, 0.45 mL (1.85 mmol) of $P(t-Bu)_3$ was added thereto, and the mixture was refluxed and agitated for 12 hours. Dichloromethane and distilled water were used to perform extraction, and an organic layer obtained therefrom was filtered with silica gel. After removing an organic solution therefrom, silica gel column was performed by using hexane:dichloromethane=7:3 (v/v), and a solid product was recrystallized with dichloromethane and acetone, obtaining 18.1 g of a compound represented by Chemical Formula 1 (a yield: 81%).

Example 3: Synthesis of Compound A-16

15.0 g (30.9 mmol) of the intermediate compound (C), 7.45 g (34.0 mmol) of naphthylphenylamine, 4.45 g (46.36 mmol) of NaO(t-Bu), and 0.28 g (0.31 mmmol) of $Pd_2(dba)_3$ were suspended in 300 ml of toluene, 0.45 mL (1.85 mmol) of $P(t-Bu)_3$ was added thereto, and the mixture was refluxed and agitated for 12 hours. Dichloromethane and distilled water was used to perform extraction, and an organic layer obtained therefrom was filtered with silica gel. After removing an organic solution therefrom, silica gel column was performed with hexane:dichloromethane=7:3 (v/v), a solid product was recrystallized with dichloromethane and n-hexane, obtaining 15.2 g of a compound represented by Chemical Formula 1 (a yield: 79%).

Example 4: Synthesis of Compound B-14

A compound represented by the above Chemical Formula B-14 as specific examples of a compound for an organic optoelectronic device according to one embodiment of the present invention was synthesized through three steps in the following Reaction Scheme 2.

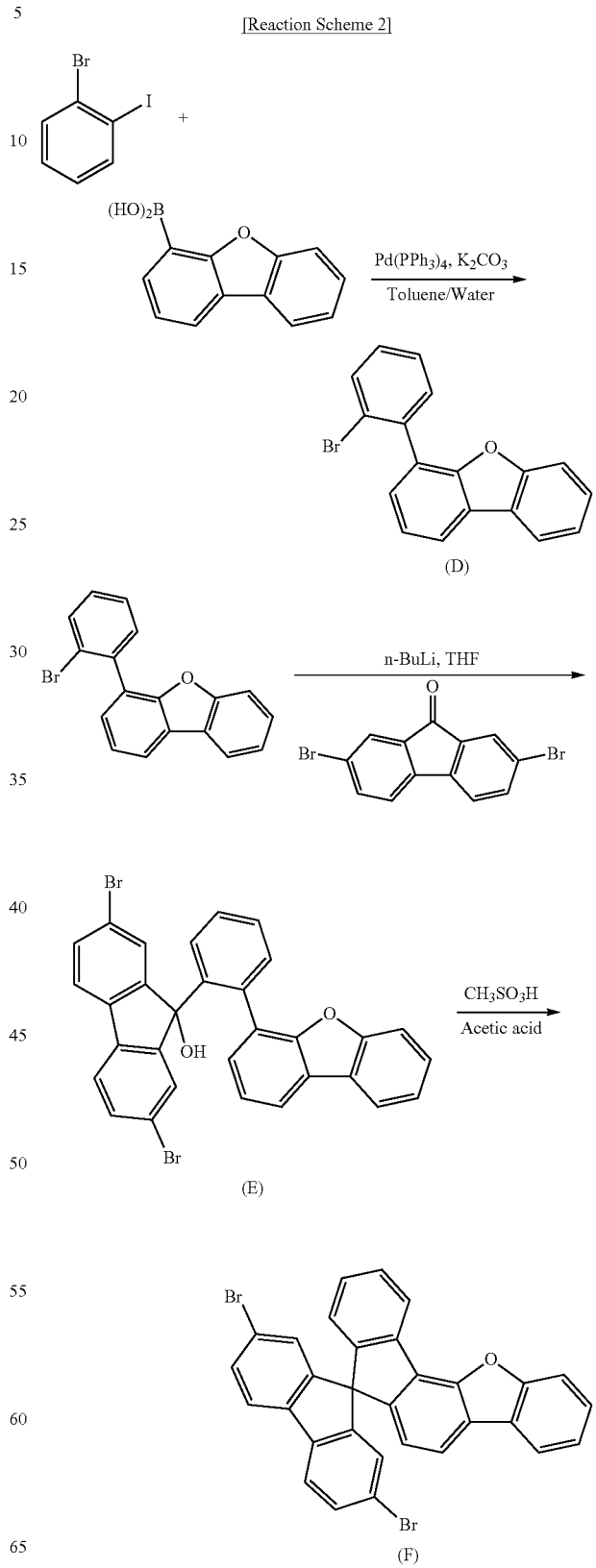

[Reaction Scheme 2]

-continued

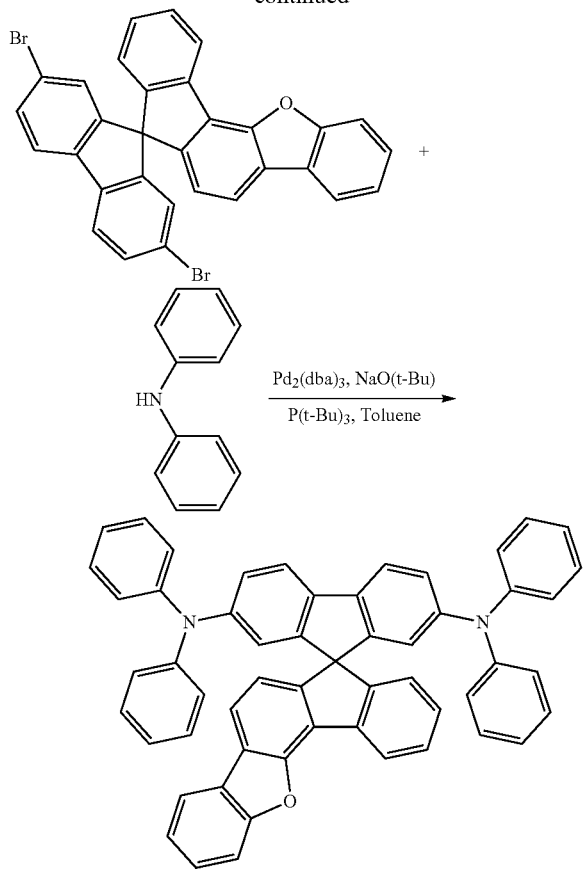

First Step: Synthesis of Intermediate Product (E)

8.2 g (25.37 mmol) of the intermediate product (A) synthesized in Example 1 was suspended in 150 mL of tetrahydrofuran, and 19.04 mL (30.45 mmol) of n-BuLi was slowly added thereto at −78° C. The mixture was agitated at −78° C. for 2 hours, 9.43 g (27.91 mol) of 2,7-dibromofluorenone was slowly added thereto, and the mixture was agitated for 24 hours. When the reaction was complete, the resultant was quenched with an ammonium chloride aqueous solution and extracted with dichloromethane, and an organic layer obtained therefrom was filtered with silica gel. After removing an organic solution therefrom, silica gel column was performed with hexane:ethylacetate=7:3 (v/v), obtaining 11.8 g of an intermediate product (E) (a yield: 80%).

Second Step: Synthesis of Intermediate Product (F)

11.8 g (20.27 mmol) of the intermediate product (E) was suspended in 200 mL of acetic acid, and 27 mL of CH3SO3H was slowly added thereto at room temperature. The mixture was agitated for 24 hours. When the reaction was complete, the resultant was quenched with 200 mL of a sodium bicarbonate aqueous solution, a solid product was filtered and extracted with dichloromethane and distilled water, and then, an organic layer obtained therefrom was filtered with silica gel. After removing an organic solution therefrom, silica gel column was performed with hexane:dichloromethane=6:4 (v/v), obtaining 9.5 g of an intermediate product (F) (a yield: 83%).

Third Step: Synthesis of Chemical Formula 2 Compound 9.43 g (16.71 mmol) of the intermediate compound (F), 6.22 g (36.77 mmol) of diphenylamine, 4.82 g (50.14 mmol) of NaO(t-Bu), and 0.31 g (0.33 mmmol) of $Pd_2(dba)_3$ were suspended in 100 ml of toluene, 0.80 mL (3.34 mmol) of $P(t-Bu)_3$ was added thereto, and the mixture was refluxed and agitated for 12 hours. Dichloromethane and distilled water were used to perform extraction, and an organic layer obtained therefrom was filtered with silica gel. After removing an organic solution, silica gel column was performed by using hexane:dichloromethane=7:3 (v/v), and a solid product obtained therefrom was recrystallized with dichloromethane and ethylacetate, obtaining 10.33 g of a compound represented by Chemical Formula 2 (a yield: 83%).

Example 5: Synthesis of Compound B-15

10.0 g (17.72 mmol) of the intermediate compound (F), 12.53 g (38.99 mmol) of biphenylphenylamine, 5.11 g (53.16 mmol) of NaO(t-Bu), and 0.32 g (0.35 mmmol) of $Pd_2(dba)_3$ were suspended in 100 ml of toluene, 0.86 mL (3.54 mmol) of $P(t-Bu)_3$ was added thereto, and the mixture was refluxed and agitated for 12 hours. Dichloromethane and distilled water were used to perform extraction, and an organic layer obtained therefrom was filtered with silica gel. After removing an organic solution therefrom, the resultant was silica gel columned with hexane:dichloromethane=7:3 (v/v), and a solid product was recrystallized with dichloromethane and ethylacetate, obtaining 10.96 g of a compound represented by Chemical Formula 2 (a yield: 83%).

Example 6: Synthesis of Compound B-21

10.0 g (17.72 mmol) of the intermediate compound (F), 8.55 g (38.99 mmol) of naphthylphenylamine, 5.11 g (53.16 mmol) of NaO(t-Bu), and 0.32 g (0.35 mmmol) of $Pd_2(dba)_3$ were suspended in 100 ml of toluene, 0.86 mL (3.54 mmol) of $P(t-Bu)_3$ was added thereto, and the mixture was refluxed and agitated for 12 hours. Dichloromethane and distilled water were used to perform extraction, and an organic layer obtained therefrom was filtered with silica gel. After removing an organic solution therefrom, silica gel column was performed by using hexane:dichloromethane=7:3 (v/v), and a solid product was recrystallized with dichloromethane and ethylacetate, obtaining 9.95 g of a compound represented by Chemical Formula 2 (a yield: 67%).

Manufacture of Organic Light Emitting Diode

Example 7: Manufacture of Organic Light Emitting Diode

ITO (indium tin oxide) was coated to be 1500 Å thick on a glass substrate, and the coated glass substrate was washed with distilled water and an ultrasonic wave. When the washing with distilled water was complete, the substrate was washed with an ultrasonic wave by using a solvent such as isopropyl alcohol, acetone, methanol, and the like and dried, then, moved to a plasma cleaner, cleaned by using oxygen plasma for 5 minute, and moved to a vacuum depositor. This ITO transparent electrode was used as an anode, and a 600 Å-thick hole injection layer (HIL) was formed thereon by vacuum-depositing 4,4'-bis[N-[4-{N,N-bis(3-methylphenyl)amino}-phenyl]-N-phenylamino]biphenyl (DNTPD). Subsequently, the compound according to Example 1 was vacuum-deposited thereon to form a 300 Å-thick hole transport layer (HTL). On the hole transport layer (HTL), a 250 Å-thick emission layer was formed by using 9,10-di-(2-naphthyl)anthracene (ADN) as a host and doping it with 3 wt % of 2,5,8,11-tetra(tert-butyl)perylene (TBPe) as a dopant.

Subsequently, on the emission layer, Alq3 was vacuum-deposited to form a 250 Å-thick electron transport layer (ETL). On the electron transport layer (ETL), a cathode was formed by sequentially vacuum-depositing LiF to be 10 Å thick and Al to be 1000 Å thick, manufacturing an organic light emitting diode.

Example 8

An organic light emitting diode was manufactured according to the same method as Example 7 except for using the compound according to Example 2 instead of the compound according to Example 1 to form the hole transport layer (HTL).

Example 9

An organic light emitting diode was manufactured according to the same method as Example 7 except for using the compound according to Example 3 instead of the compound according to Example 1 to form the hole transport layer (HTL).

Example 10

An organic light emitting diode was manufactured according to the same method as Example 7 except for using the compound according to Example 4 instead of the compound according to Example 2 to form the hole transport layer (HTL).

Example 11

An organic light emitting diode was manufactured according to the same method as Example 7 except for using the compound according to Example 5 instead of the compound according to Example 2 to form the hole transport layer (HTL).

Example 12

An organic light emitting diode was manufactured according to the same method as Example 7 except for using the compound according to Example 6 instead of the compound according to Example 2 to form the hole transport layer (HTL).

Comparative Example 1

An organic light emitting diode was manufactured according to the same method as Example 7 except for using NPB instead of the compound according to Example 2 to form the hole transport layer (HTL).

(Performance Measurement of Organic Light Emitting Diode)

Current density change, luminance change, and luminous efficiency of each organic light emitting diode according to Examples 7 to 12 and Comparative Example 1 depending on a voltage were measured. Specific measurement methods are as follows, and the results are shown in the following Table 1.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

The luminance, current density, and voltage obtained from the (1) and (2) were used to calculate current efficiency (cd/A) and power efficiency (lm/W) at the same luminance (1,000 cd/m$^2$).

TABLE 1

| Device | Compound used in hole transport layer (HTL) | Voltage (V) | Color (EL color) | Efficiency (cd/A) | Efficiency (lm/W) |
|---|---|---|---|---|---|
| Example 7 | A-14 | 5.8 | Blue | 6.2 | 3.4 |
| Example 8 | A-15 | 5.6 | Blue | 6.4 | 3.6 |
| Example 9 | A-16 | 5.5 | Blue | 6.1 | 3.5 |
| Example 10 | B-14 | 5.2 | Blue | 6.5 | 3.9 |
| Example 11 | B-15 | 5.0 | Blue | 6.0 | 3.8 |
| Example 12 | B-21 | 5.1 | Blue | 6.1 | 3.8 |
| Comparative Example 1 | NPB | 7.1 | Blue | 4.9 | 2.2 |

Current density: 10 mA/cm$^2$

All the organic light emitting diodes according to Examples 7 to 12 decreased a driving voltage and improved luminance and efficiency compared with the organic light emitting diode according to Comparative Example 1.

Accordingly, an organic light emitting diode having a low voltage, high efficiency, high luminance, and long life-span as well as excellent electron injection and transportation capability may be manufactured.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic device represented by a combination of the following Chemical Formula 1 and Chemical Formula 2:

[Chemical Formula 1]

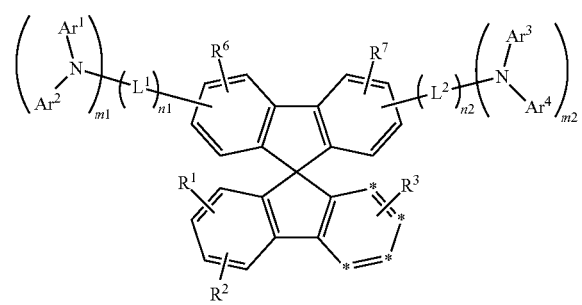

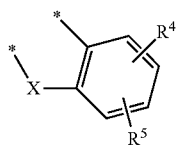

wherein, in the above Chemical Formulae 1 and 2,
X is —O—, —S—, —S(O)—, or —S(O)$_2$—,
$Ar^1$ to $Ar^4$ are independently a substituted or unsubstituted C6 to C30 aryl group, or a substituted or unsubstituted C2 to C30 heteroaryl group,
$L^1$ and $L^2$ are independently a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group,
m1 and m2 are independently integers of 0 or 1, one of m1 and m2 is 1,
n1 and n2 are independently integers ranging from 0 to 3,
$R^1$ to $R^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group, and
the *s of Chemical Formula 2 correspond with two adjacent *s of Chemical Formula 1 to form a fused ring.

2. The compound for an organic optoelectronic device of claim 1, wherein the above Chemical Formula 1 is represented by the following Chemical Formula 3:

[Chemical Formula 3]

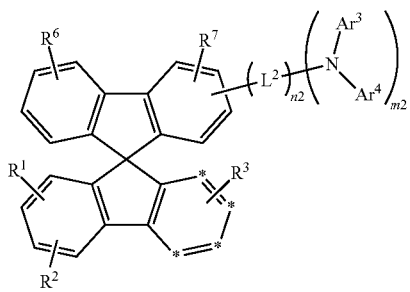

wherein, in the above Chemical Formula 3,
$Ar^3$ and $Ar^4$ are independently a substituted or unsubstituted C6 to C30 aryl group, or a substituted or unsubstituted C2 to C30 heteroaryl group,
$L^2$ is a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group,
m2 is 1,
n2 is an integer ranging from 0 to 3,
$R^1$ to $R^3$, $R^6$ and $R^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group, and
the *s of Chemical Formula 2 correspond with two adjacent *s of Chemical Formula 3 to form a fused ring.

3. The compound for an organic optoelectronic device of claim 1, wherein the compound for an organic optoelectronic device is represented by the following Chemical Formula 4:

[Chemical Formula 4]

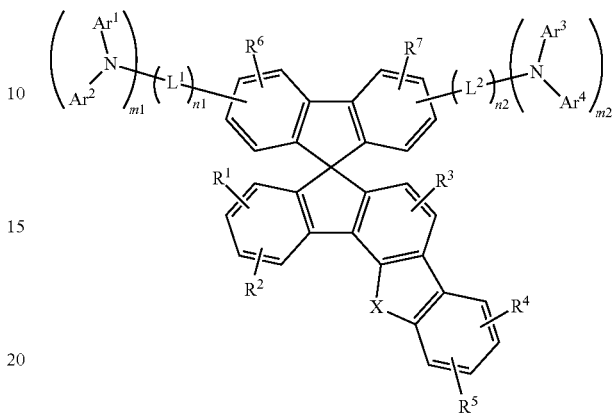

wherein, in the above Chemical Formula 4,
X is —O—, —S—, —S(O)—, or —S(O)$_2$—,
$Ar^1$ to $Ar^4$ are independently a substituted or unsubstituted C6 to C30 aryl group, or a substituted or unsubstituted C2 to C30 heteroaryl group,
$L^1$ and $L^2$ are independently a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group,
m1 and m2 are independently integers of 0 or 1, one of m1 and m2 is 1,
n1 and n2 are independently integers ranging from 0 to 3, and
$R^1$ to $R^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

4. The compound for an organic optoelectronic device of claim 1, wherein the compound for an organic optoelectronic device is represented by the following Chemical Formula 5:

[Chemical Formula 5]

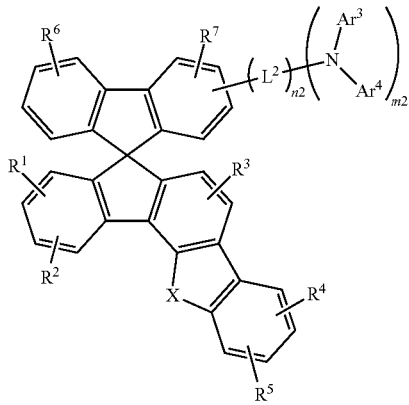

wherein, in the above Chemical Formula 5,

X is —O—, —S—, —S(O)—, or —S(O)$_2$—,

Ar$^3$ and Ar$^4$ are independently a substituted or unsubstituted C6 to C30 aryl group, or a substituted or unsubstituted C2 to C30 heteroaryl group, L$^2$ is a single bond, a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m2 is 1, n2 is an integer ranging from 0 to 3, and R$^1$ to R$^7$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

5. The compound for an organic optoelectronic device of claim 1, wherein Ar$^1$ to Ar$^4$ are each independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiopheneyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiopheneyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

6. The compound for an organic optoelectronic device of claim 1, wherein the compound for an organic optoelectronic device is represented by one of the following Chemical Formulae A-1 to A-72:

[Chemical Formula A-1]

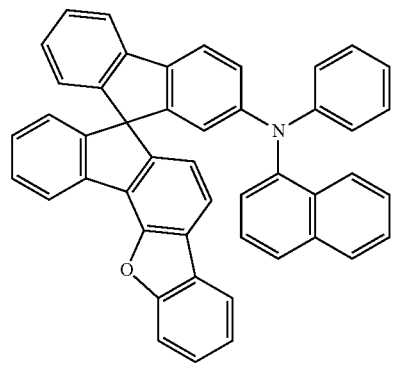

[Chemical Formula A-2]

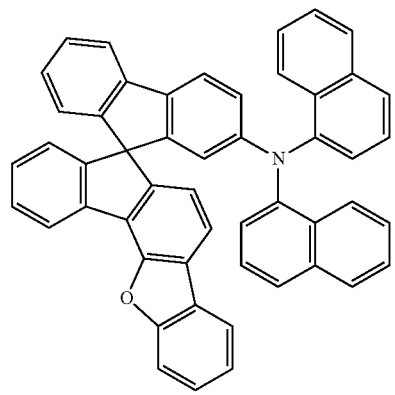

[Chemical Formula A-3]

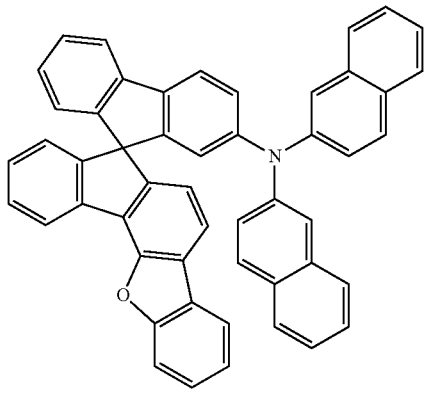

[Chemical Formula A-4]

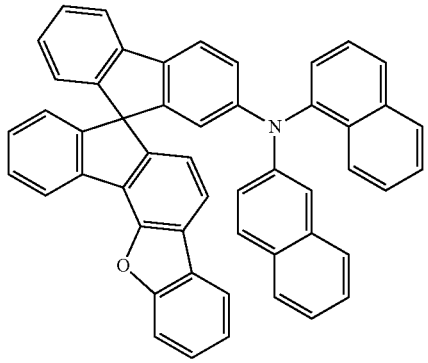

[Chemical Formula A-5]
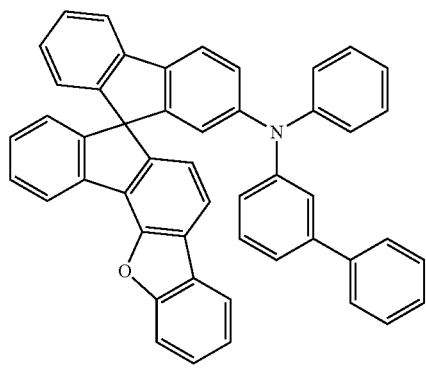
[Chemical Formula A-6]
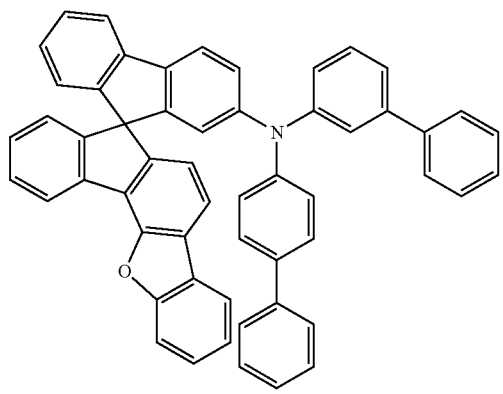
[Chemical Formula A-7]
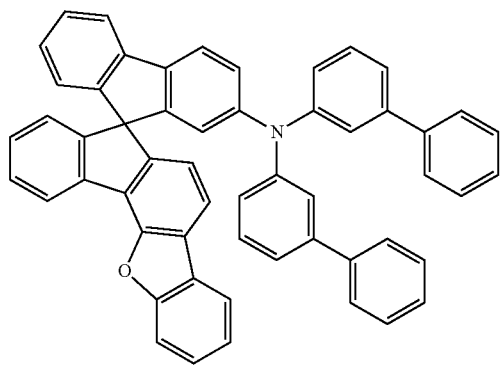
[Chemical Formula A-8]
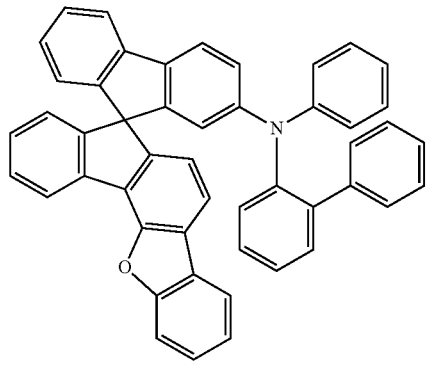
[Chemical Formula A-9]
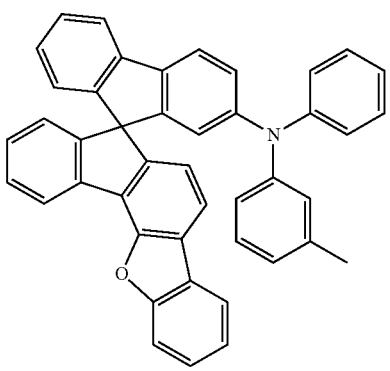
[Chemical Formula A-10]
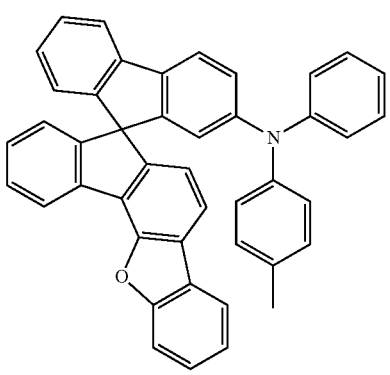
[Chemical Formula A-11]
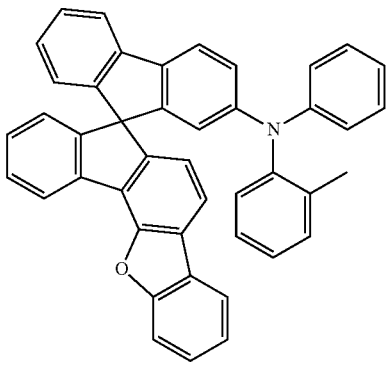
[Chemical Formula A-12]
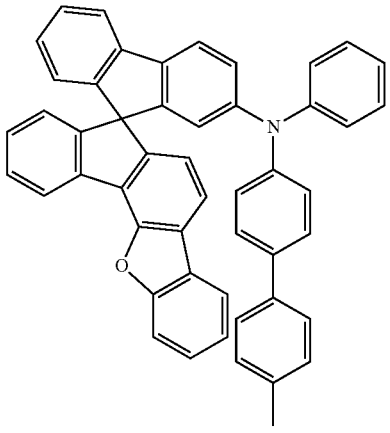

[Chemical Formula A-13]
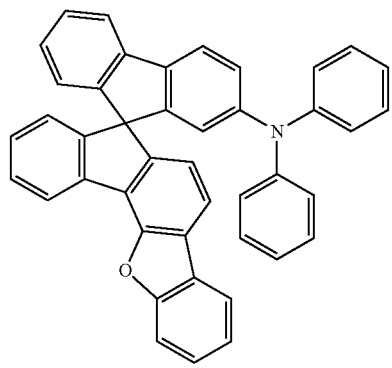
[Chemical Formula A-14]
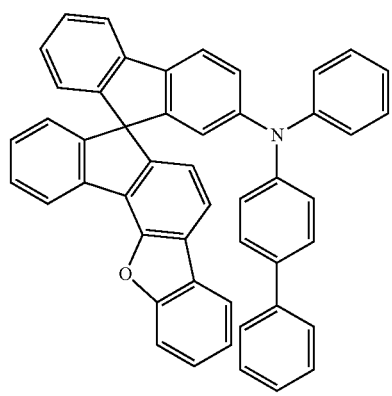
[Chemical Formula A-15]
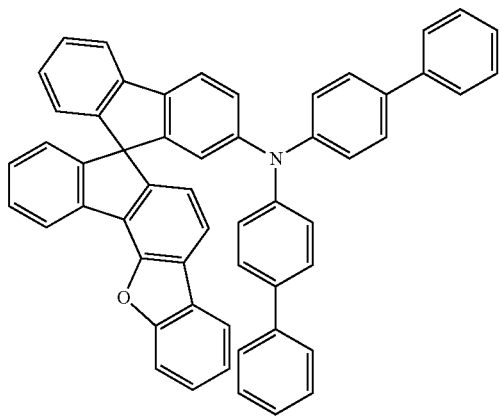
[Chemical Formula A-16]
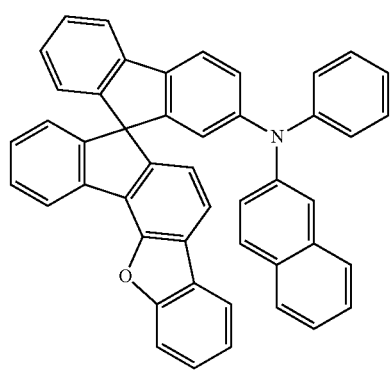
[Chemical Formula A-17]
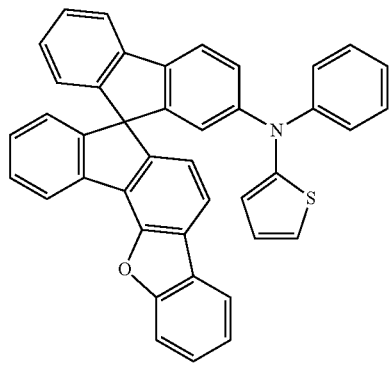
[Chemical Formula A-18]
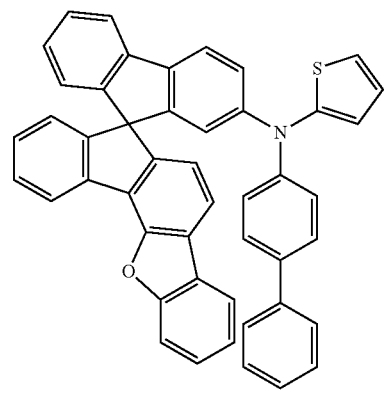
[Chemical Formula A-19]
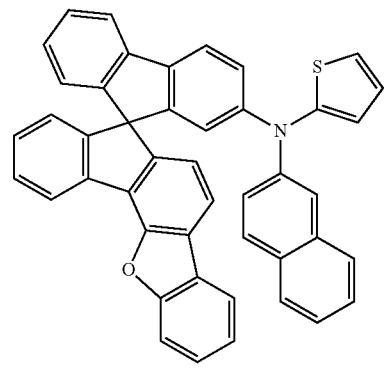
[Chemical Formula A-20]
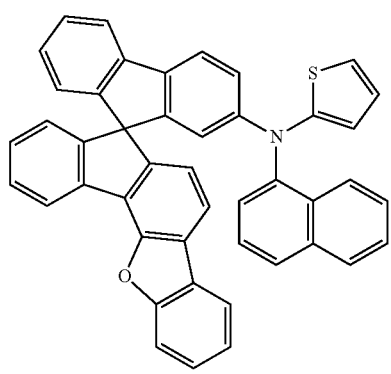

[Chemical Formula A-21]
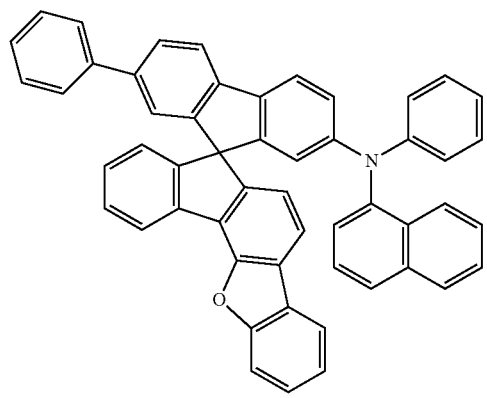
[Chemical Formula A-22]
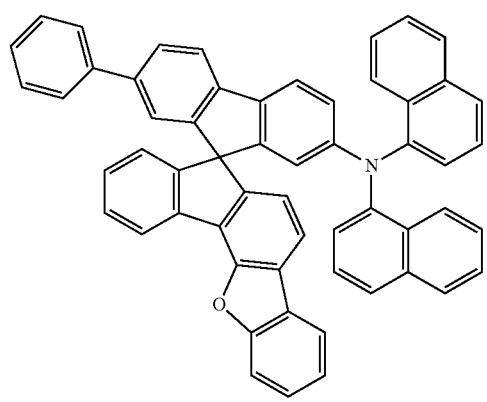
[Chemical Formula A-23]
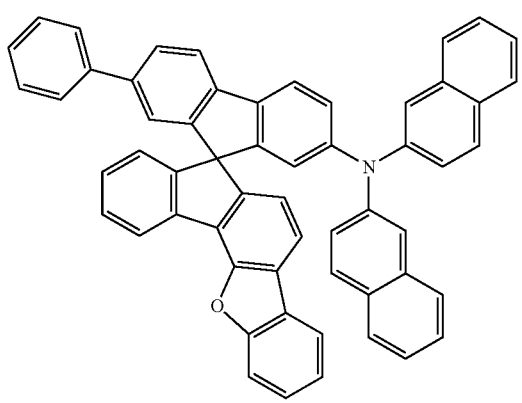
[Chemical Formula A-24]
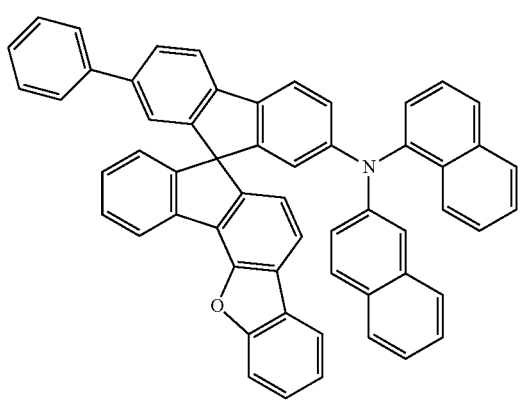
[Chemical Formula A-25]
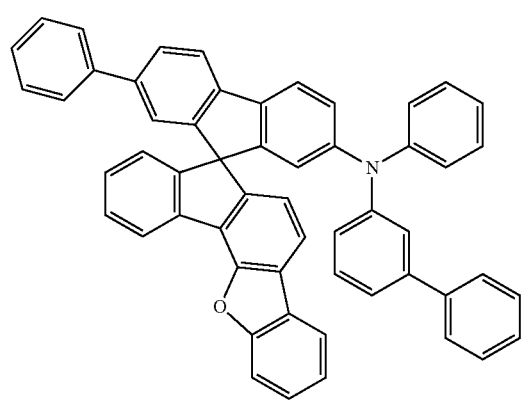
[Chemical Formula A-26]
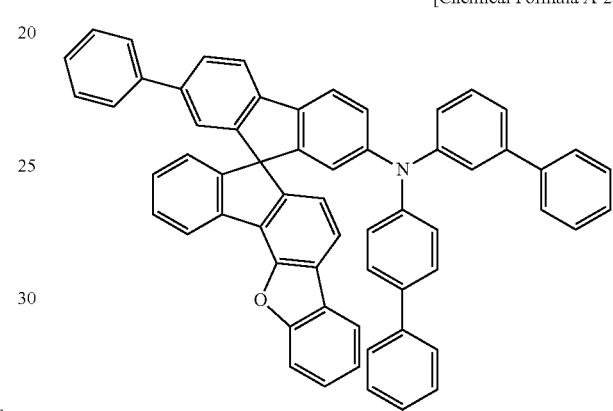
[Chemical Formula A-27]
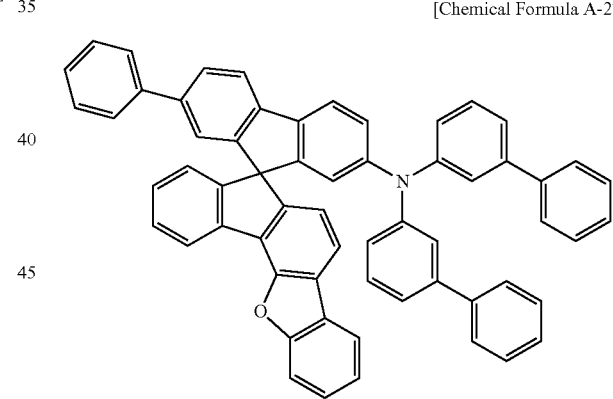
[Chemical Formula A-28]
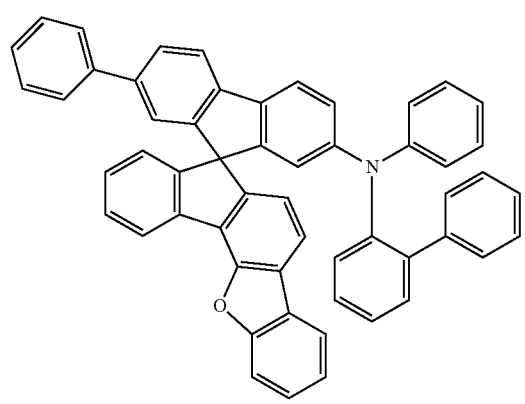

[Chemical Formula A-29]
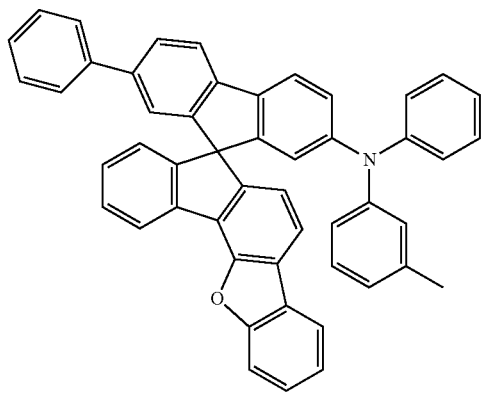
[Chemical Formula A-30]
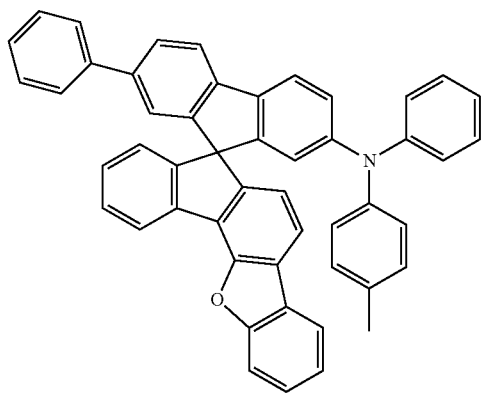
[Chemical Formula A-31]
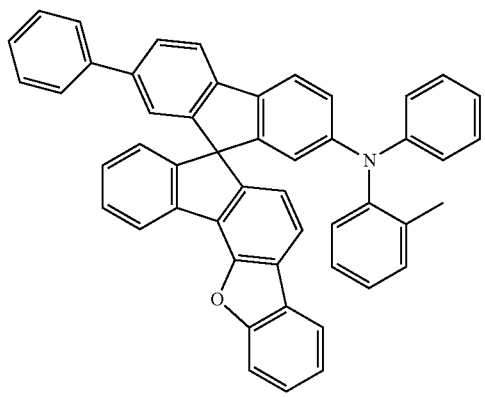
[Chemical Formula A-32]
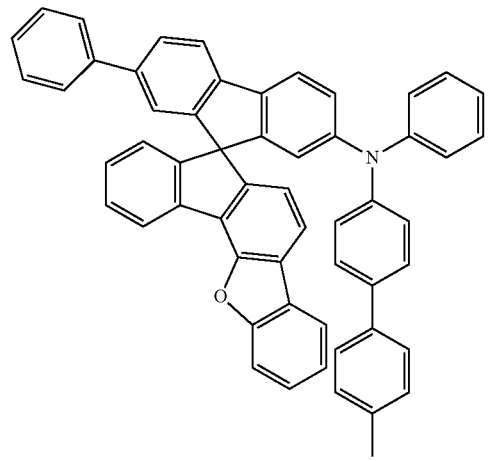
[Chemical Formula A-33]
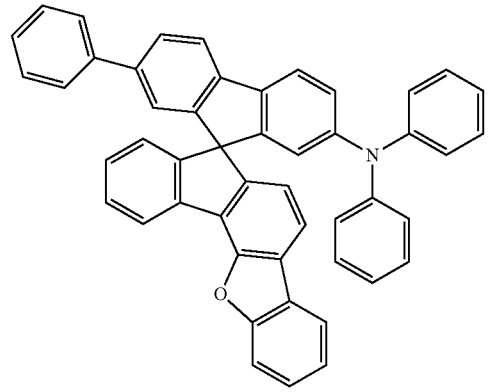
[Chemical Formula A-34]
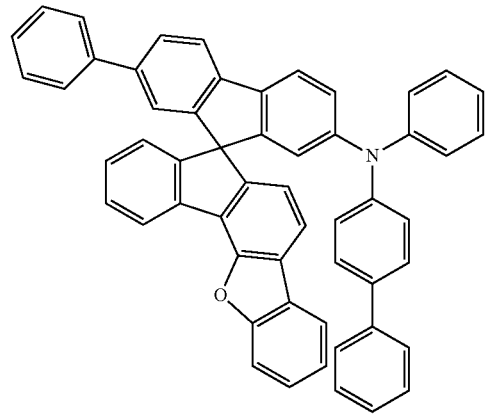

[Chemical Formula A-35]
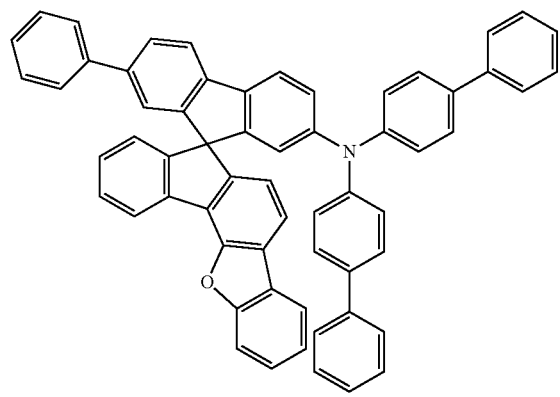
[Chemical Formula A-36]
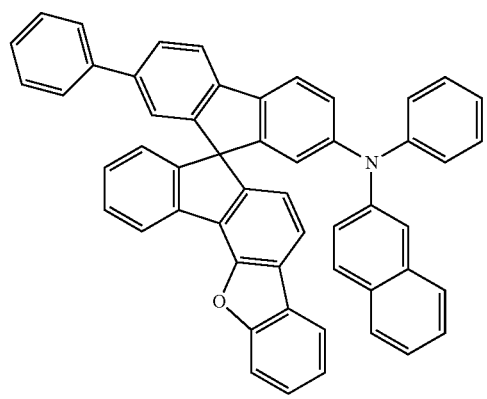
[Chemical Formula A-37]
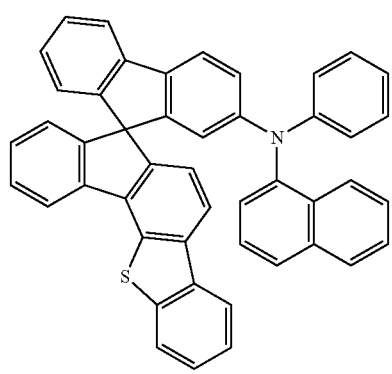
[Chemical Formula A-38]
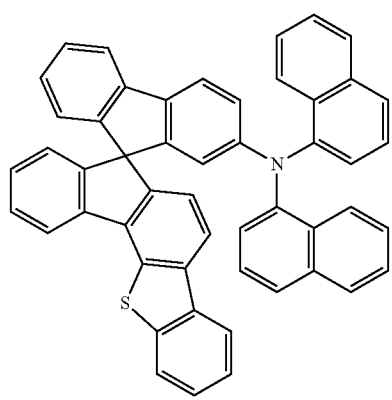
[Chemical Formula A-39]
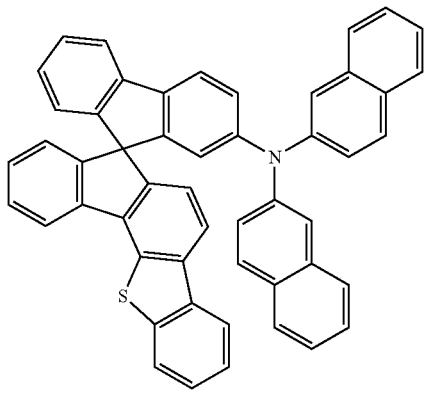
[Chemical Formula A-40]
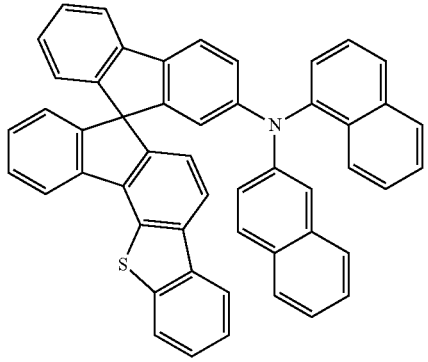
[Chemical Formula A-41]
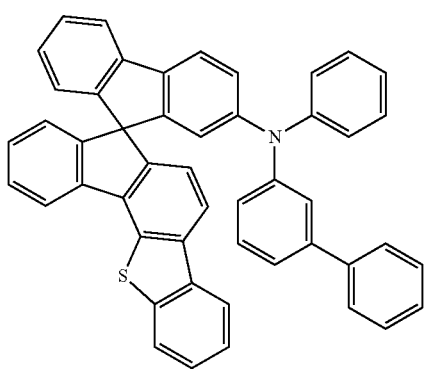
[Chemical Formula A-42]
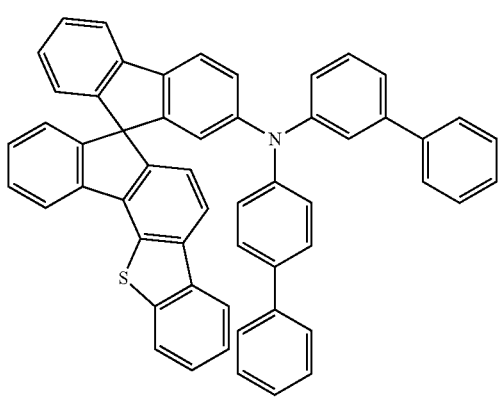

-continued
[Chemical Formula A-43]
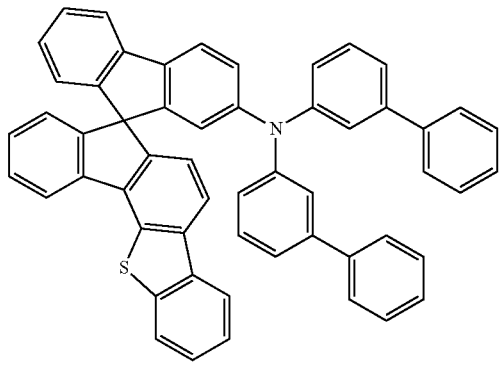
[Chemical Formula A-44]
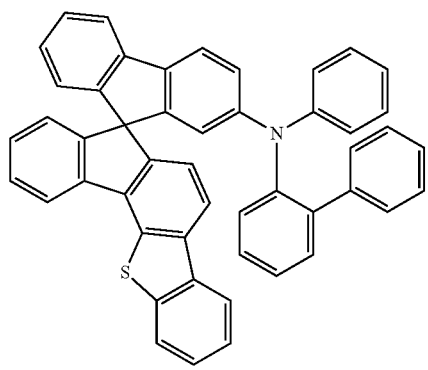
[Chemical Formula A-45]
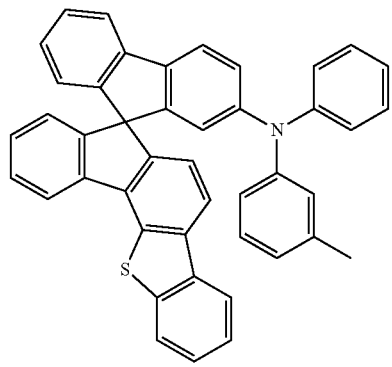
[Chemical Formula A-46]
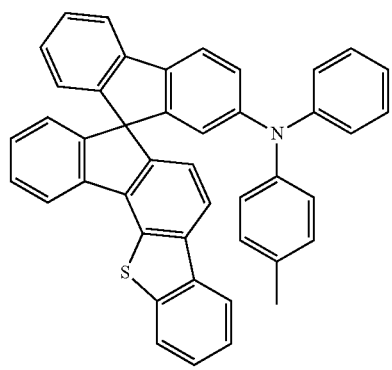
-continued
[Chemical Formula A-47]
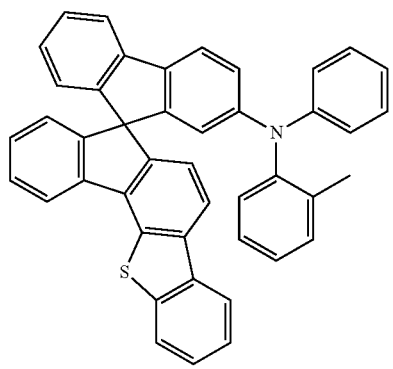
[Chemical Formula A-48]
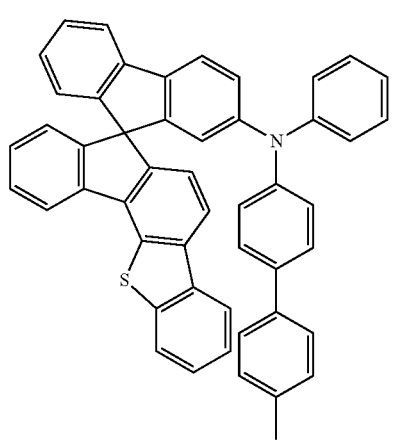
[Chemical Formula A-49]
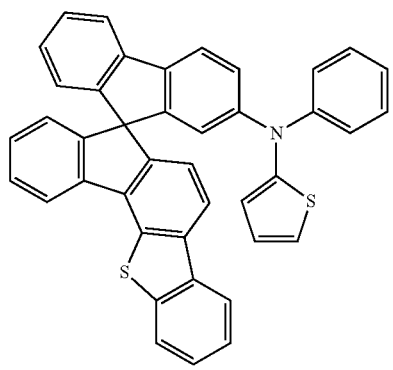
[Chemical Formula A-50]
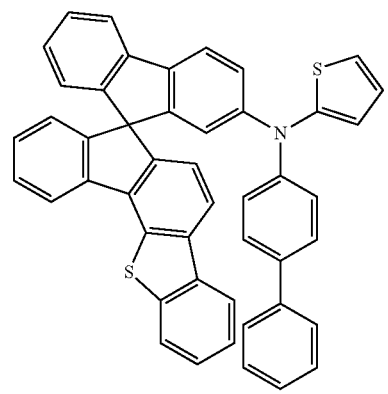

[Chemical Formula A-51]
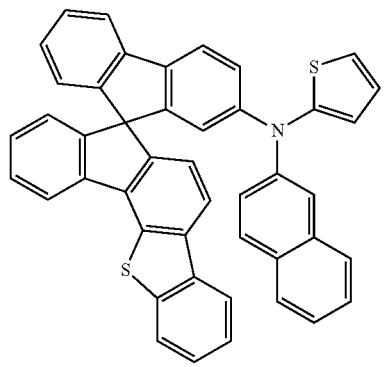
[Chemical Formula A-52]
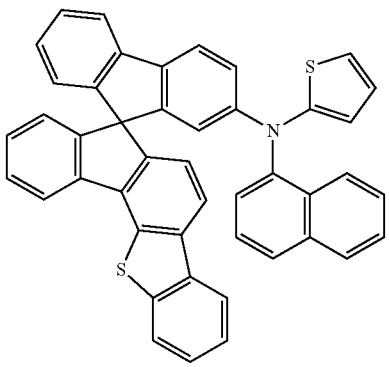
[Chemical Formula A-53]
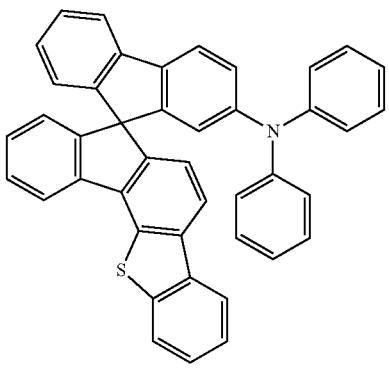
[Chemical Formula A-54]
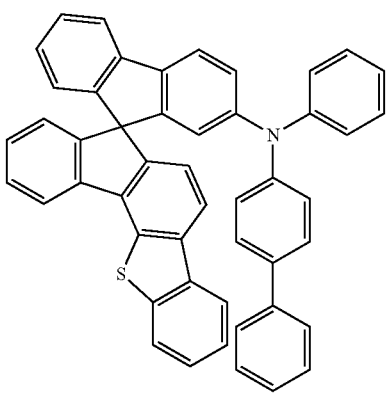
[Chemical Formula A-55]
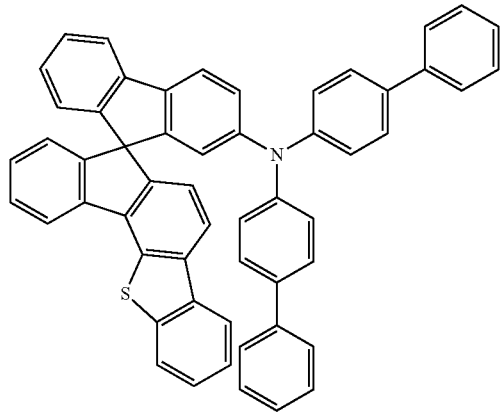
[Chemical Formula A-56]
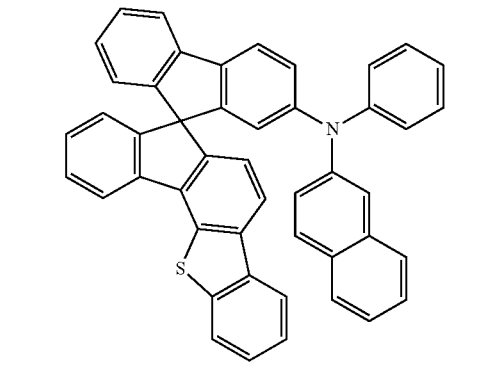
[Chemical Formula A-57]
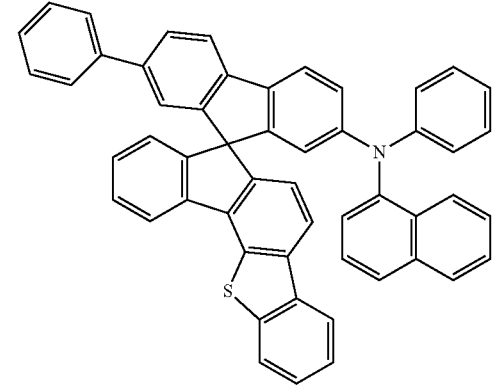
[Chemical Formula A-58]
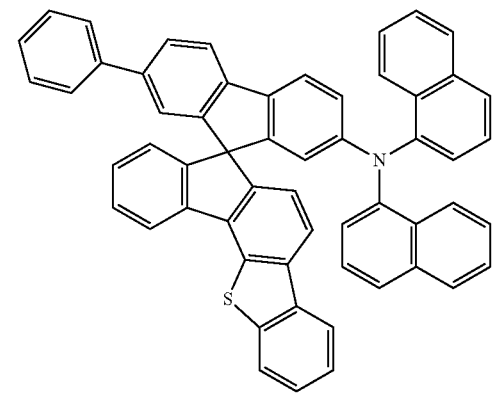

[Chemical Formula A-59]
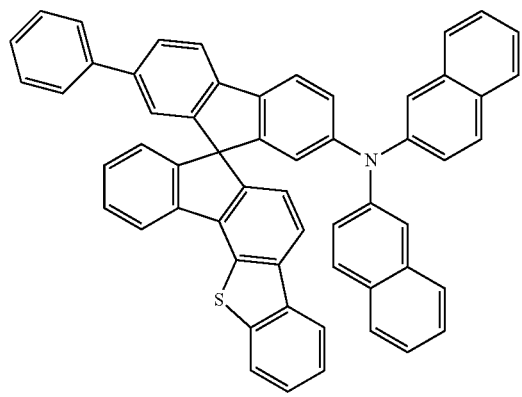
[Chemical Formula A-60]
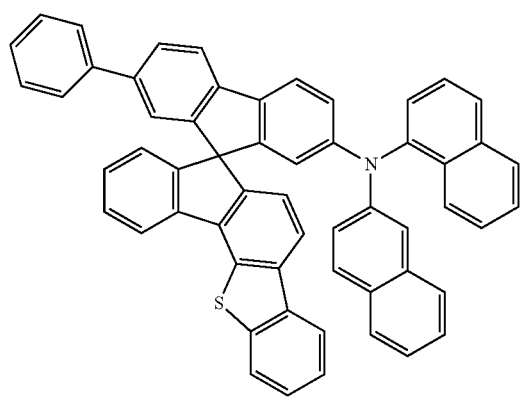
[Chemical Formula A-61]
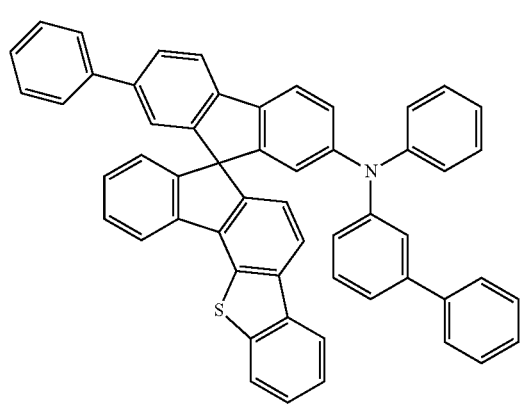
[Chemical Formula A-62]
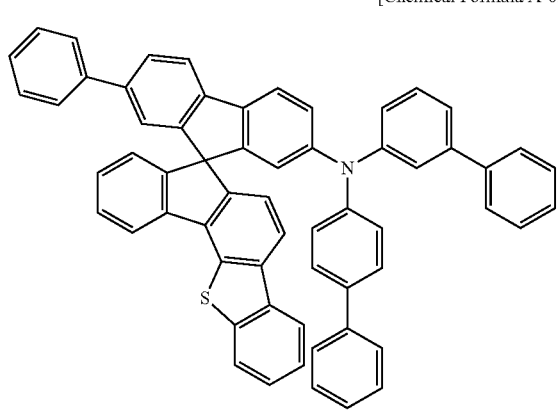
[Chemical Formula A-63]
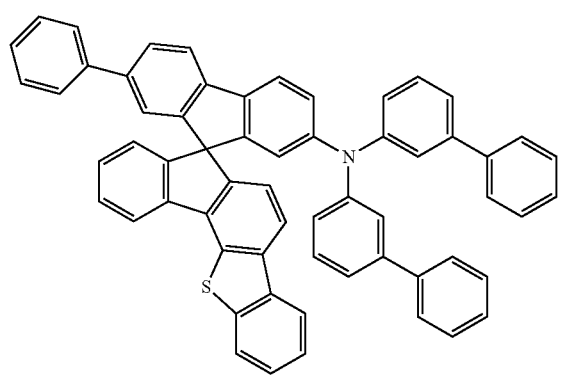
[Chemical Formula A-64]
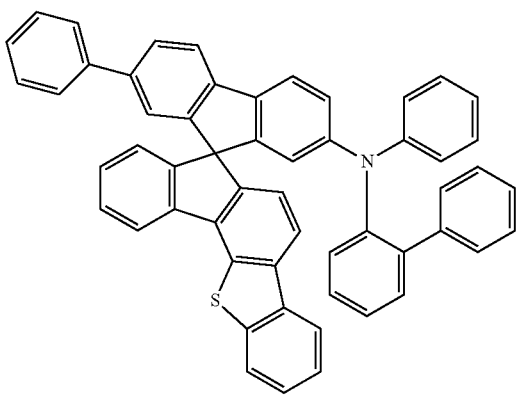
[Chemical Formula A-65]
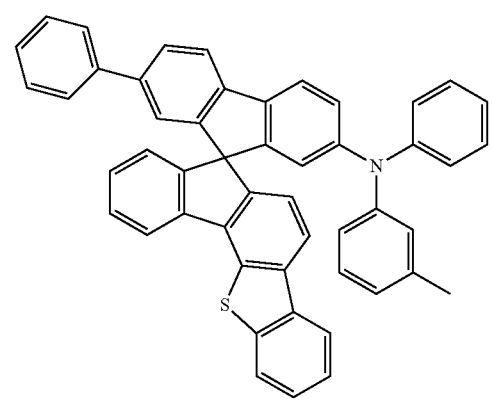
[Chemical Formula A-66]
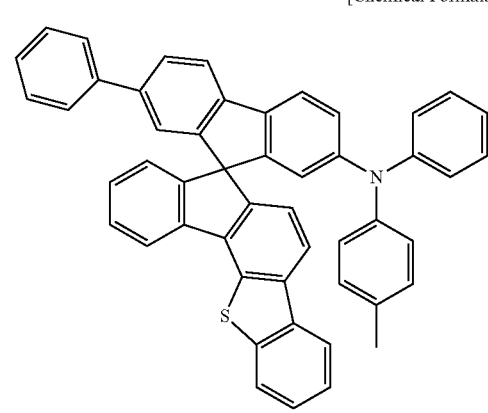

[Chemical Formula A-67]
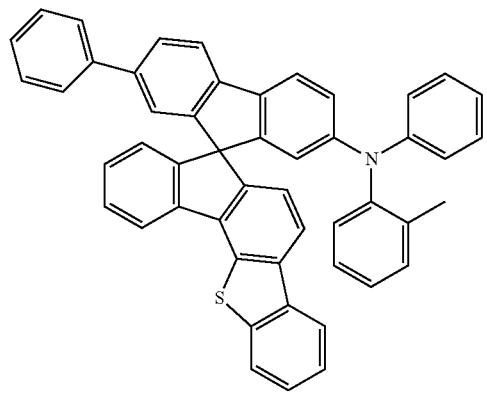
[Chemical Formula A-68]
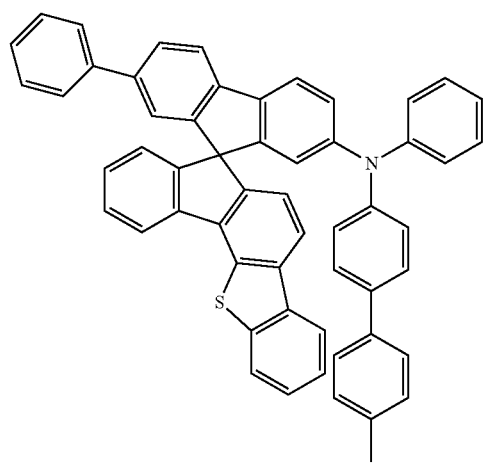
[Chemical Formula A-69]
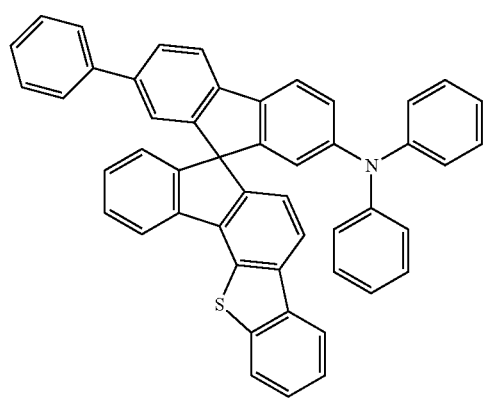
[Chemical Formula A-70]
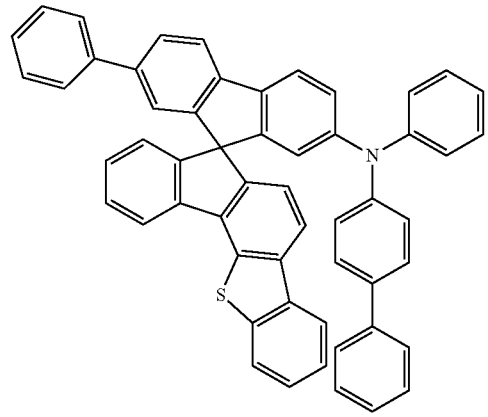
[Chemical Formula A-71]
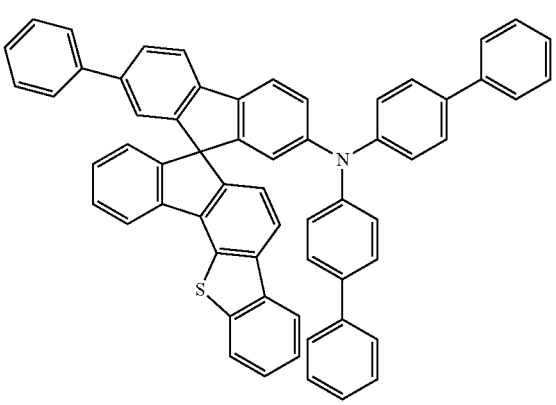
[Chemical Formula A-72]
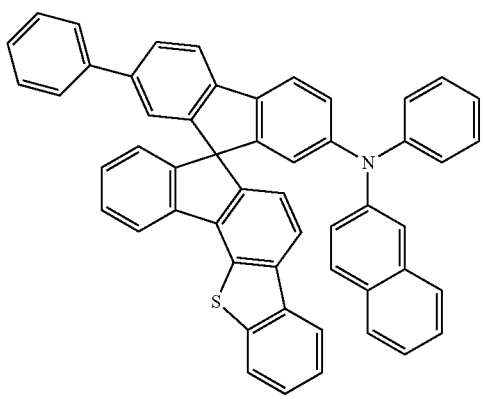
7. The compound for an organic optoelectronic device of claim 1, wherein the compound for an organic optoelectronic device is represented by one of the following Chemical Formulae B-1 to B-40:

[Chemical Formula B-1]
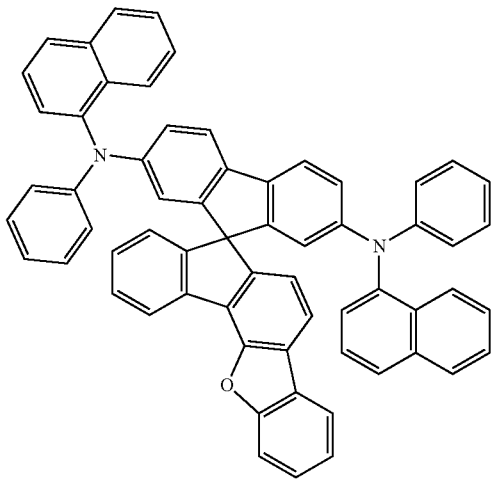
[Chemical Formula B-2]
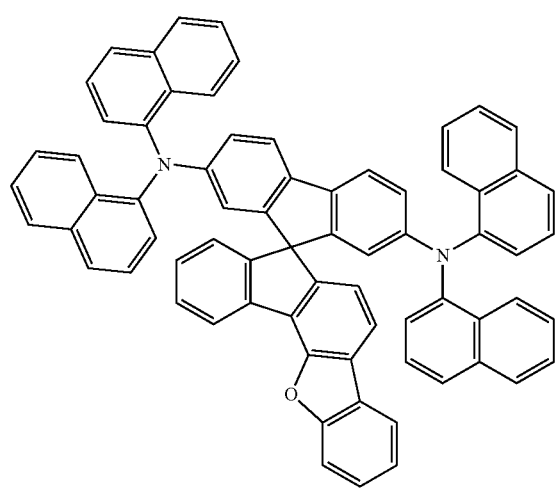
[Chemical Formula B-3]
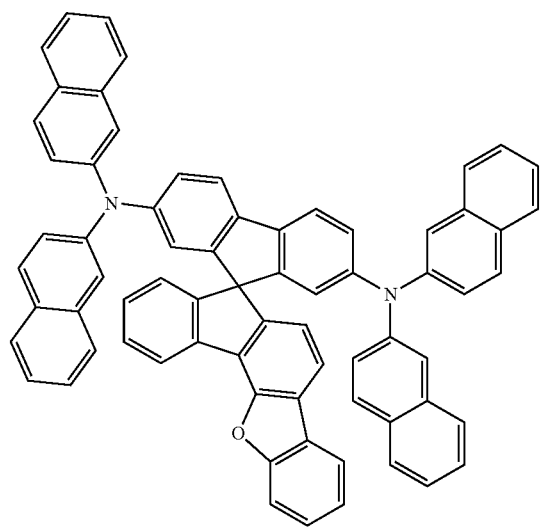
[Chemical Formula B-4]
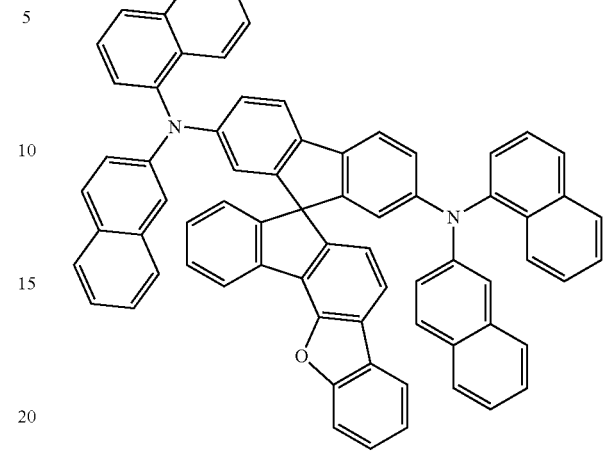
[Chemical Formula B-5]
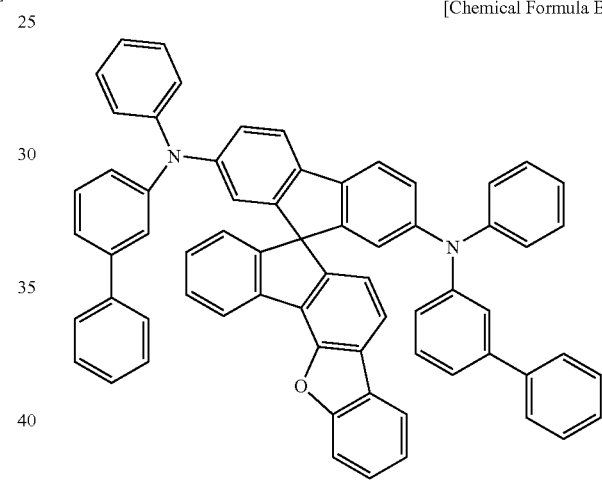
[Chemical Formula B-6]
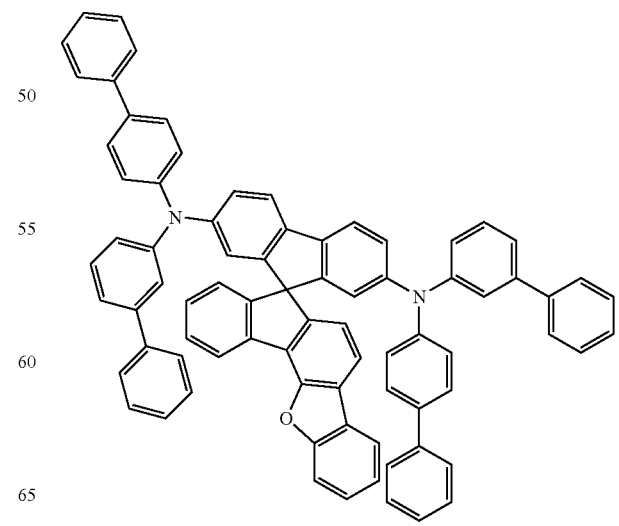

-continued
[Chemical Formula B-7]
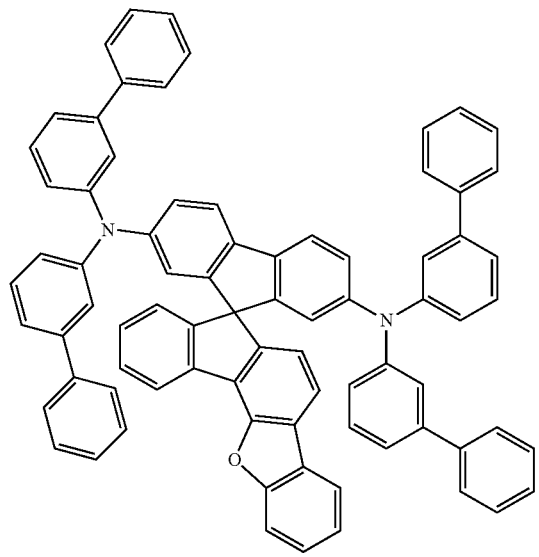
[Chemical Formula B-8]
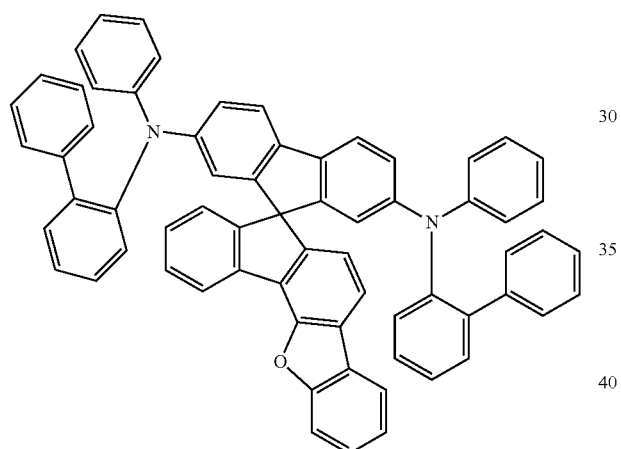
[Chemical Formula B-9]
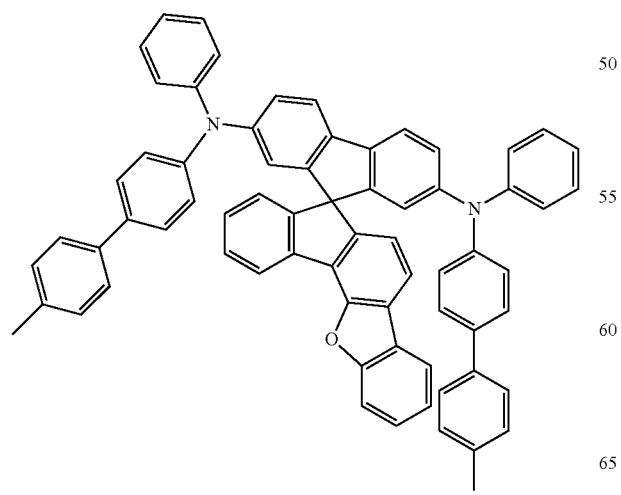
-continued
[Chemical Formula B-10]
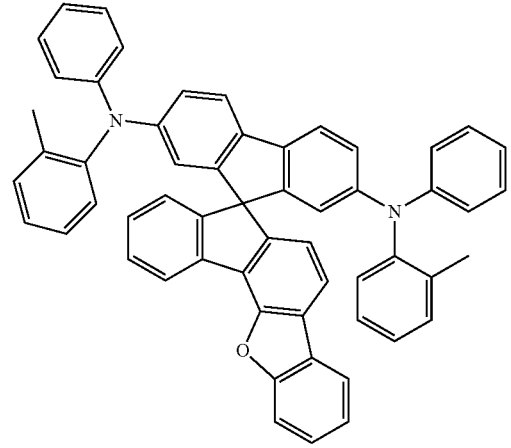
[Chemical Formula B-11]
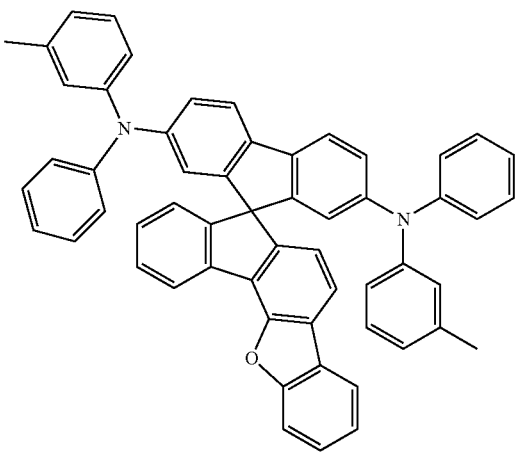
[Chemical Formula B-12]
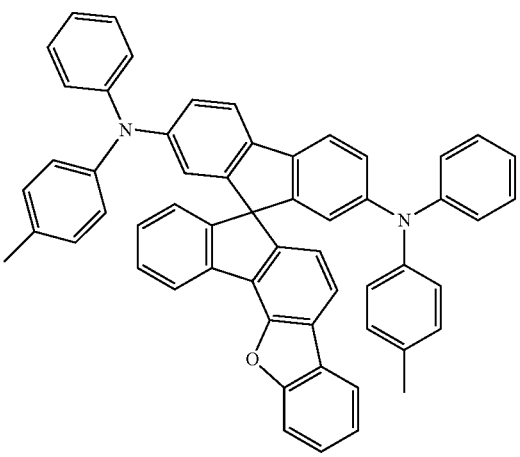

[Chemical Formula B-13]
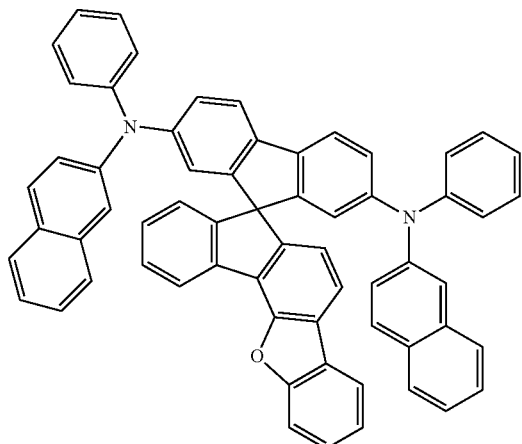
[Chemical Formula B-16]
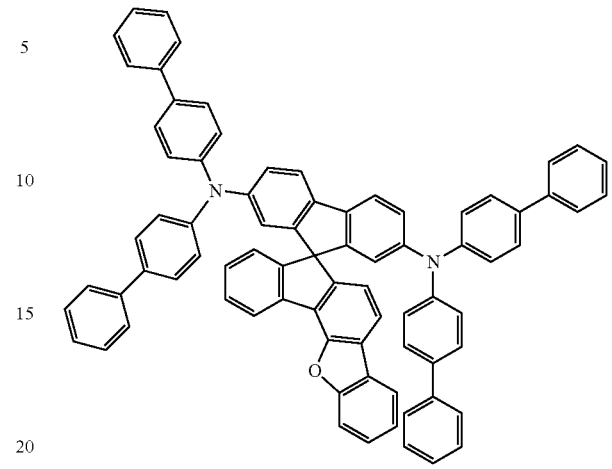
[Chemical Formula B-14]
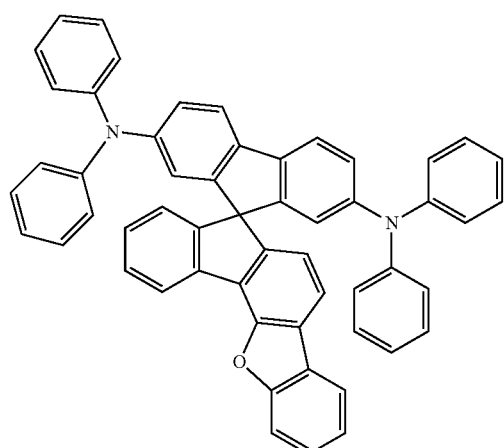
[Chemical Formula B-17]
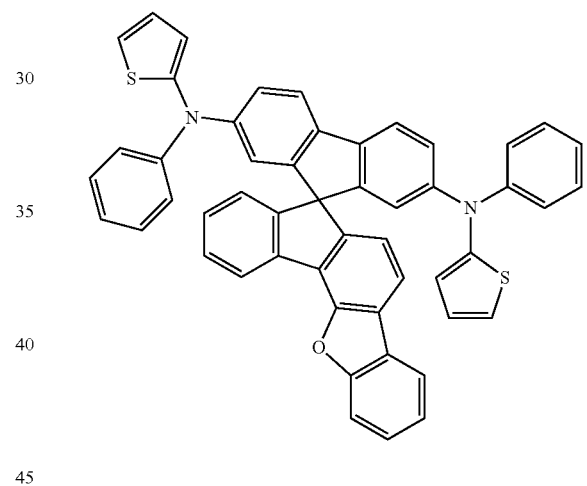
[Chemical Formula B-15]
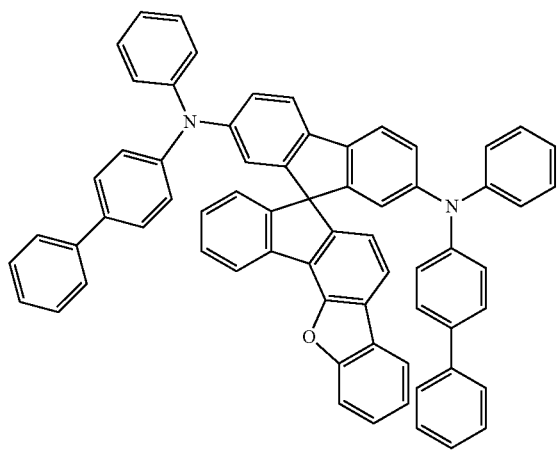
[Chemical Formula B-18]
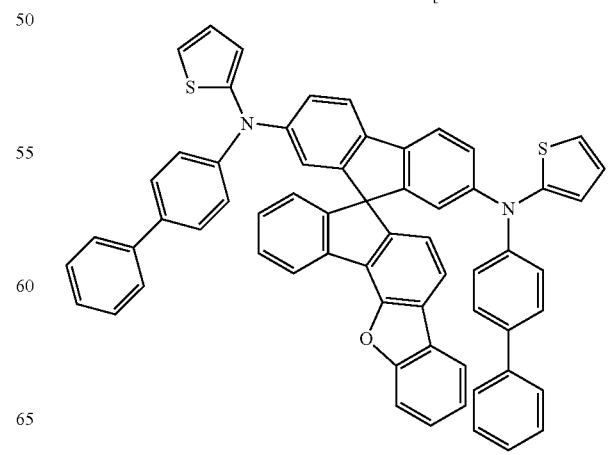

[Chemical Formula B-19]
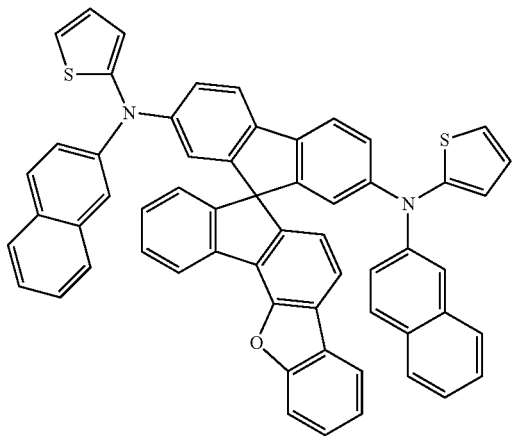
[Chemical Formula B-20]
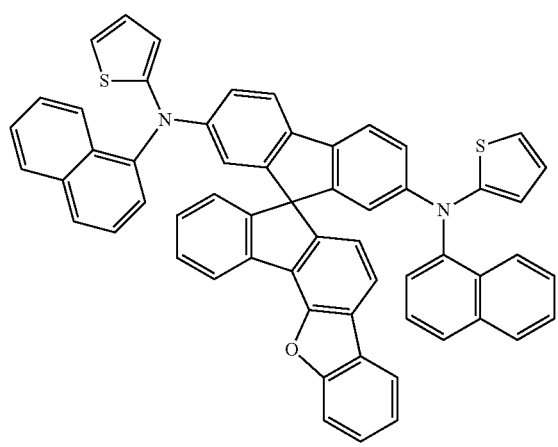
[Chemical Formula B-21]
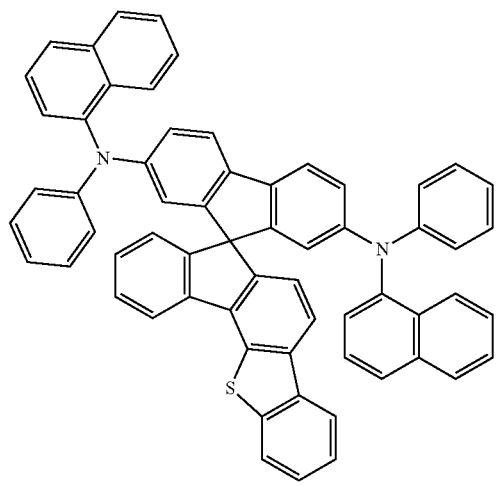
[Chemical Formula B-22]
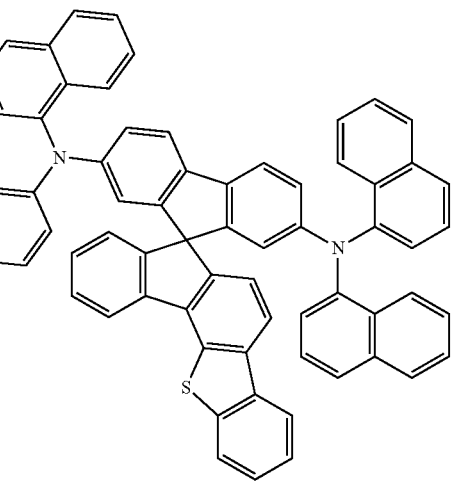
[Chemical Formula B-23]
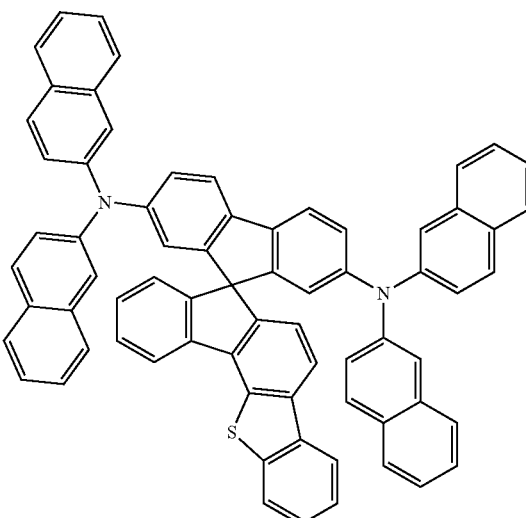
[Chemical Formula B-24]
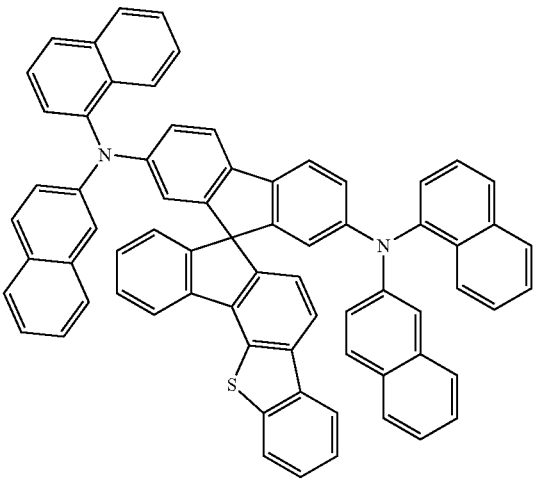

[Chemical Formula B-25]
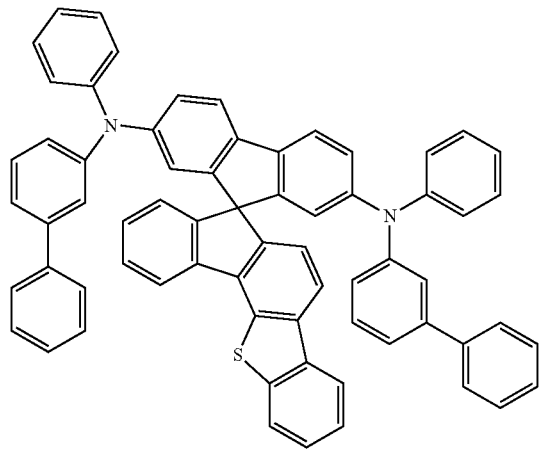
[Chemical Formula B-26]
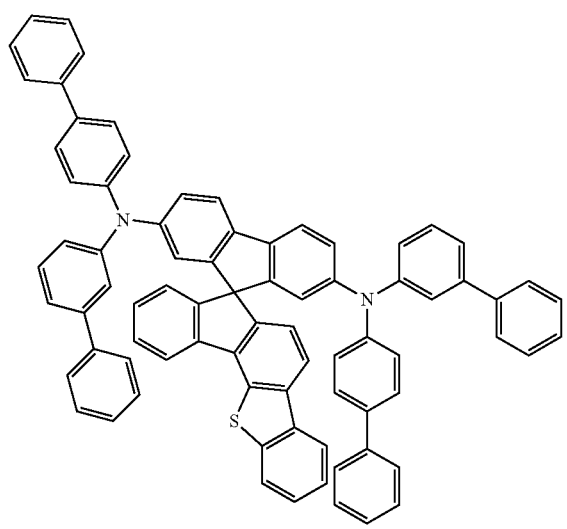
[Chemical Formula B-27]
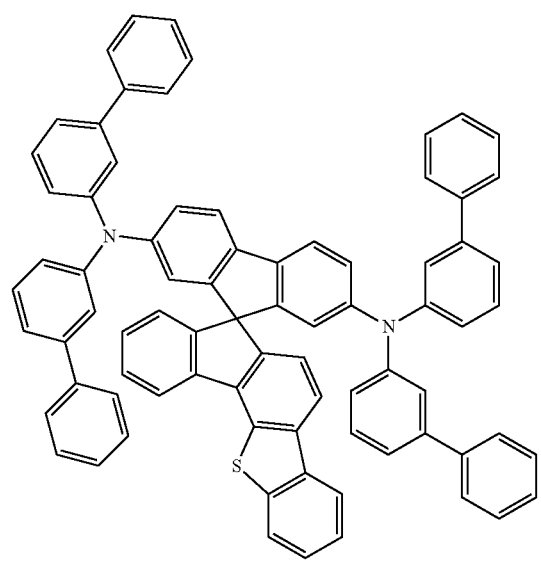
[Chemical Formula B-28]
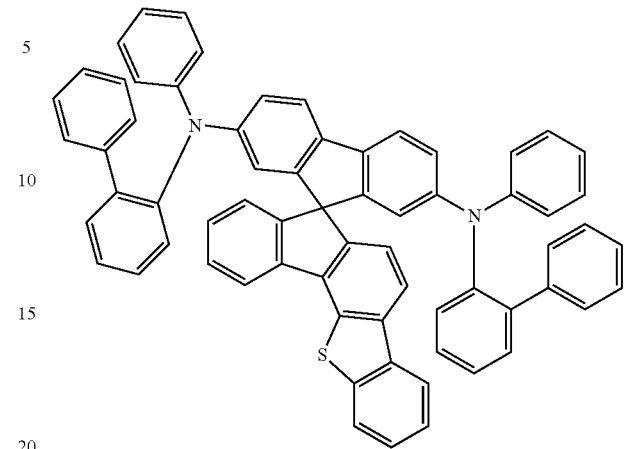
[Chemical Formula B-29]
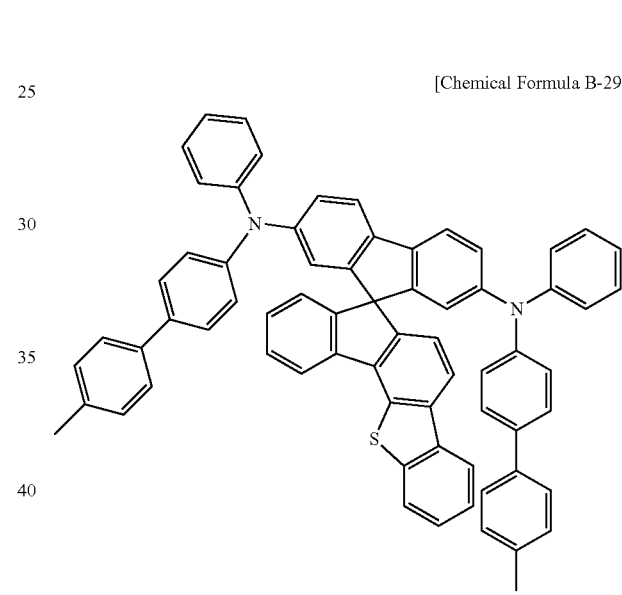
[Chemical Formula B-30]
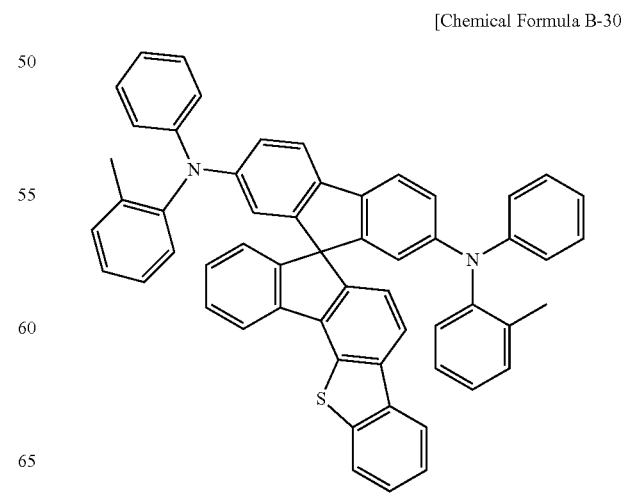

[Chemical Formula B-31]
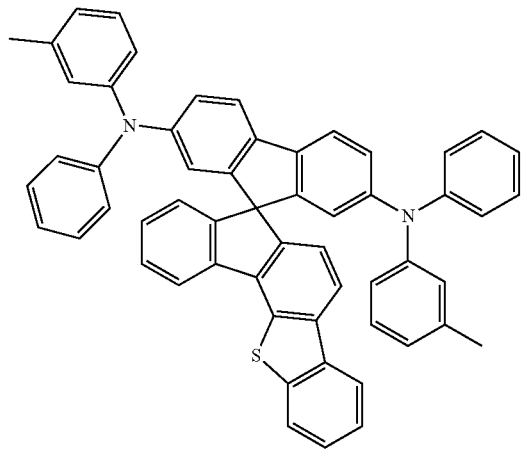
[Chemical Formula B-32]
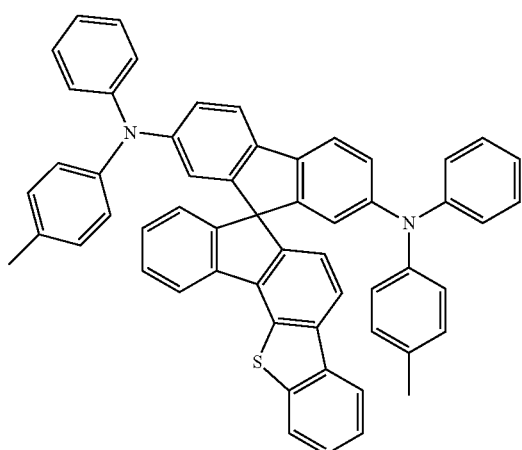
[Chemical Formula B-33]
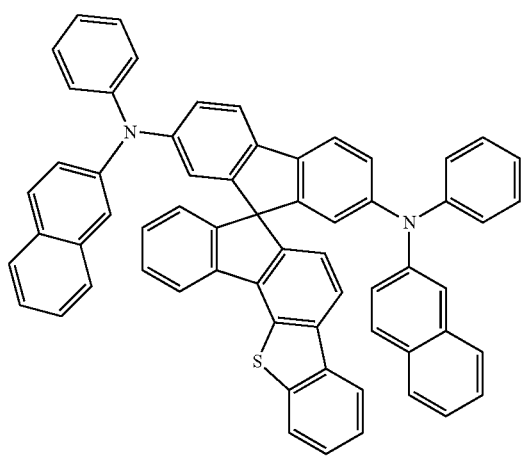
[Chemical Formula B-34]
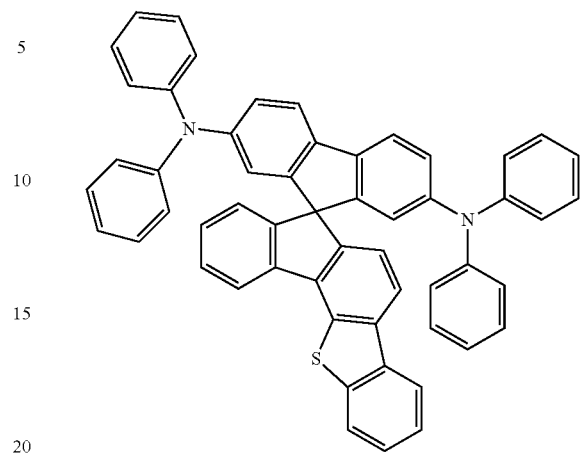
[Chemical Formula B-35]
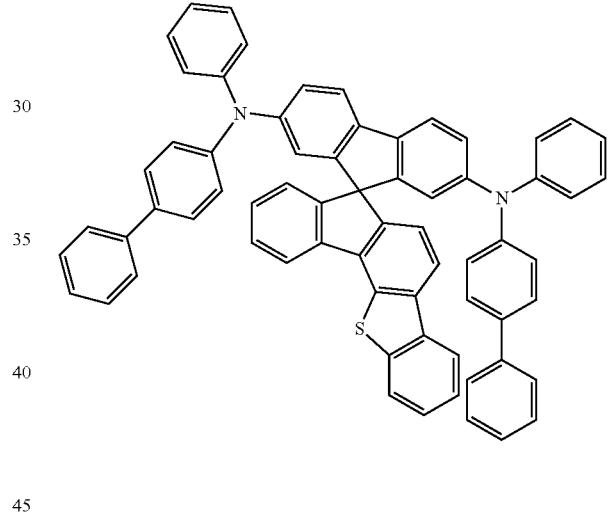
[Chemical Formula B-36]
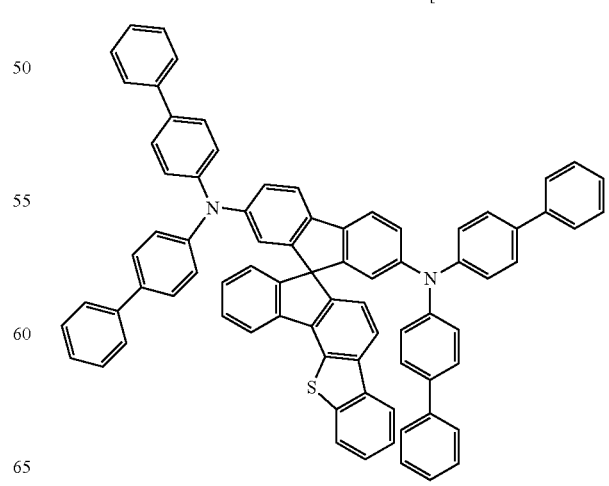

[Chemical Formula B-37]

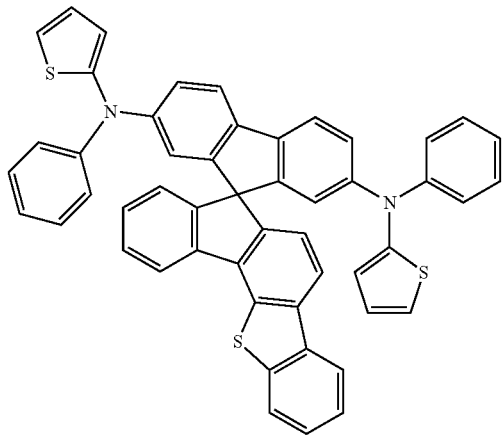

[Chemical Formula B-38]

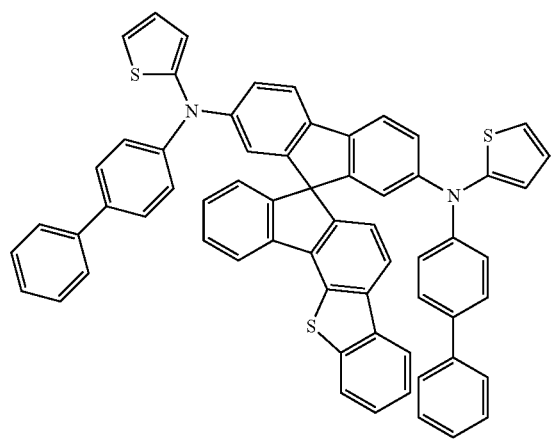

[Chemical Formula B-39]

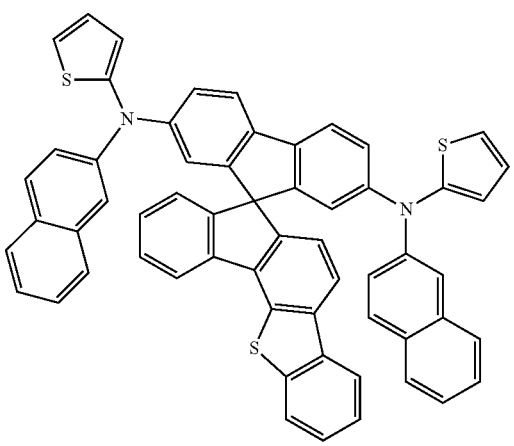

[Chemical Formula B-40]

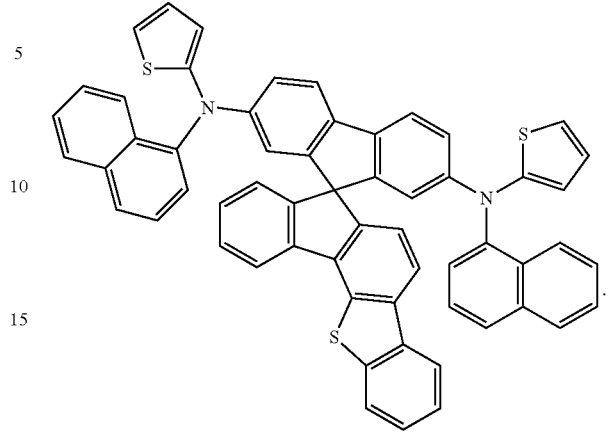

8. The compound for an organic optoelectronic device of claim 1, wherein the compound for an organic optoelectronic device has a triplet exciton energy (T1) of greater than or equal to about 2.0 eV.

9. The compound for an organic optoelectronic device of claim 1, wherein the organic optoelectronic device is selected from an organic photoelectric device, an organic light emitting diode, an organic solar cell, an organic transistor, an organic photo-conductor drum, and an organic memory device.

10. An organic light emitting diode, comprising
an anode, a cathode, and at least one organic thin layer interposed between the anode and cathode,
wherein the at least one organic thin layer comprises the compound for an organic optoelectronic device of claim 1.

11. The organic light emitting diode of claim 10, wherein the at least one organic thin layer is selected from an emission layer, a hole transport layer, a hole injection layer, an electron transport layer, an electron injection layer, a hole blocking layer, and a combination thereof.

12. The organic light emitting diode of claim 11, wherein the compound for an organic optoelectronic device is included in the hole transport layer (HTL) or the hole injection layer (HIL).

13. The organic light emitting diode of claim 11, wherein the compound for an organic optoelectronic device is included in the emission layer.

14. The organic light emitting diode of claim 13, wherein the compound for an organic optoelectronic device is used as a phosphorescent or fluorescent host material in the emission layer.

15. A display device comprising the organic light emitting diode of claim 10.

* * * * *